(12) United States Patent
Anderson et al.

(10) Patent No.: US 6,218,426 B1
(45) Date of Patent: Apr. 17, 2001

(54) NON-PEPTIDE GNRH AGENTS

(75) Inventors: Mark Brian Anderson, Orinda; Alexander Polinsky, La Jolla; Yufeng Hong, San Diego; Vlad Edward Gregor, Del Mar, all of CA (US)

(73) Assignee: Agouron Pharmaceuticals, Inc.

( * ) Notice: Subject to any disclaimer, the term of this patent is extended or adjusted under 35 U.S.C. 154(b) by 0 days.

(21) Appl. No.: 09/259,206

(22) Filed: Mar. 1, 1999

Related U.S. Application Data

(60) Provisional application No. 60/076,983, filed on May 5, 1998.

(51) Int. Cl.[7] .............................. A01N 43/06; C07C 69/34
(52) U.S. Cl. ........................ 514/448; 514/471; 514/613; 514/634; 549/72; 549/461; 549/483; 549/487; 564/161; 564/170; 564/237; 560/190
(58) Field of Search ................................. 514/255, 337, 514/323, 448, 471, 663, 634; 548/496, 495; 549/72, 461, 483, 487; 564/161, 170, 237; 560/190

(56) References Cited

U.S. PATENT DOCUMENTS

| | | | |
|---|---|---|---|
| 4,565,804 | 1/1986 | Rivier et al. | 514/15 |
| 5,506,207 | 4/1996 | Rivier et al. | 514/15 |

FOREIGN PATENT DOCUMENTS

| | | |
|---|---|---|
| 9303058 | 2/1993 | (WO) . |
| 9500474 | 1/1995 | (WO) . |
| 9721703 | 6/1997 | (WO) . |

OTHER PUBLICATIONS

Mitchinson et al., "Discrimination of Spermidine Amino Functions by a New Protecting Group Strategy; Application to the Synthesis of Guanidinylated Polyamines, Including Hirudonine," *J. Chem. Soc. Commun.*, 1994, 2613–2614.

Yorke et al., "Synthesis of Acarnidines: Guanidinated Spermidine Homologues Through Imine Intermediates," *Aust. J. Chem.*, vol. 39, 1986, 447–455.

*Primary Examiner*—Paul J. Killos

(57) ABSTRACT

Non-peptide GnRH agents capable of inhibiting the effect of gonadotropin-releasing hormone are of the following general formula, where $X_1$, $X_2$, Y, and are defined variables:

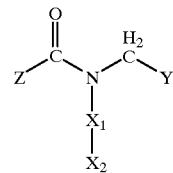

Such compounds and their pharmaceutically acceptable salts, multimers, prodrugs, and active metabolites are suitable for treating mammalian reproductive disorders and steroid hormone-dependent tumors as well as for regulating fertility, where suppression of gonadotropin release is indicated. Methods for synthesizing the compounds and intermediates useful in their preparation are also described.

16 Claims, 2 Drawing Sheets

NON-PEPTIDE GNRH AGENTS

CROSS-REFERENCE TO RELATED APPLICATION

This application is related to U.S. Provisional Application Ser. No. 60/076,983, filed May 3, 1998, in the name of Anderson et al., the disclosure of which is incorporated by reference herein.

TECHNICAL FIELD AND INDUSTRIAL APPLICABILITY OF THE INVENTION

This invention relates generally to compounds that affect the action of human gonadotropin-releasing hormone (GnRH). More particularly, it relates to non-peptide GnRH antagonists or agonists and to their preparation. These non-peptide GnRH agents have advantageous physical, chemical and biological properties, and are useful medicaments for diseases or conditions mediated by modulation of the pituitary-gonadal axis. The compounds of the invention avoid the degradation and biodistribution problems of peptide agents.

BACKGROUND OF THE INVENTION

The release of a hormone (a biochemical substance that is produced by a specific cell or tissue and causes a change or an activity in a cell or tissue located elsewhere in the organism) by the anterior lobe of the pituitary gland (which is located at the base of the brain and secretes hormones related to growth and sexual development) usually requires the prior release of another class of hormones produced by the hypothalamus (a structure in the lower part of the brain that is connected to and controls the pituitary gland). One of the hypothalamic hormones acts as a factor that triggers the release of the gonadotropic hormones, particularly LH (luteinizing hormone, which is the pituitary hormone that causes the testicles in men and ovaries in women to manufacture sex hormones) and FSH (follicle-stimulating hormone, which is the pituitary hormone that stimulates follicle growth in women and sperm formation in men). This hormone is referred to herein as "GnRH" (gonadotropin-releasing hormone) and/or "LH-RH" (luteinizing hormone-releasing hormone). GnRH is a decapeptide hormone produced by the arcuate nuclei of the hypothalamus (an arcuate nucleus is any of the cellular masses in the thalamus, hypothalamus, or medulla oblongata) that controls the pituitary gland's production and release of gonadotropins (hormones including FSH and LH that are produced by the pituitary gland that control reproductive function). GnRH (LH-RH) may be represented by the sequence pyro-Glu-His-Trp-Ser-Tyr-Gly-Leu-Arg-Pro-Gly-$NH_2$ or, in the single-letter code designation, pyro-EHWSYGLRPG-$NH_2$. GnRH acts on high-affinity pituitary receptors to stimulate LH and FSH production and release.

The pituitary response to GnRH varies greatly throughout life. GnRH and the gonadotropins first appear in the fetus at about ten weeks of gestation. The sensitivity to GnRH declines, after a brief rise during the first three months after birth, until the onset of puberty. Before puberty, the FSH response to GnRH is greater than that of LH. Once puberty begins, sensitivity to GnRH increases, and pulsatile LH secretion ensues. Later in puberty and throughout the reproductive years, pulsations occur throughout the day, with LH responsiveness being greater than that of FSH. After menopause, FSH and LH concentrations rise, and postmenopausal FSH levels are higher than those of LH.

Pulsatile GnRH release results in pulsatile LH and FSH release. However, sustained infusion of GnRH and its analogs results in inhibition of LH and FSH release. This phenomenon has been utilized in the successful treatment of gonadotropin-mediated precocious puberty by the sustained administration of LH-RH or its analogs. Conversely, in people with GnRH deficiency, the pulsatile administration of LH-RH can restore a normal menstrual cycle or normal sperm and testosterone production.

GnRH agonists, which are compounds that stimulate the pituitary gland to release or modulate FSH and LH, have been the mode of choice for treating sex-steroid-dependent pathophysiologies, owing to the limited number of suitable antagonists available for clinical evaluation. GnRH antagonists, which are compounds that suppress the pituitary gland from releasing FSH and LH, however, are now being considered.

GnRH antagonists may be useful for suppressing gonadotropin secretions and preventing ovulation in female mammals. GnRH antagonists have been investigated for contraception and for regulating conception periods, as well as for treating infertility, for controlling induction of ovulation in women with chronic anovulation, and for in vitro fertilization. GnRH antagonists may also be useful for the treatment of precocious puberty, endometriosis (including endometriosis with pain), acne, amenorrhea (e.g., secondary amenorrhea), uterine myoma, ovarian and mammary cystic diseases (including polycystic ovarian disease), and breast and gynecological cancers. GnRH antagonists may also be useful in the symptomatic relief of premenstrual syndrome (PMS). They may also be used to treat ovarian hyperandrogenism and hirsutism. Antagonists have also been found useful to regulate the secretion of gonadotropins in male mammals and may be employed to arrest spennatogenesis, e.g., as male contraceptives for treatment of male sex offenders, and for treatment of prostatic hypertrophy. More specifically, GnRH antagonists may be used to treat steroid-dependent tumors, such as prostatic and mammary tumors, and for the control of the timing of ovulation for in vitro fertilization. GnRH antagonists may also be used to treat patients having illnesses, such as AIDS, wherein stimulation of the thymus to produce T-cells would be beneficial. All such uses relate to the ability of the GnRH antagonist to block the activity of GnRH.

Heretofore, available GnRH antagonists have primarily been peptide analogs of GnRH. See, e.g., International Publication No. WO 93/03058. Peptide antagonists of peptide hormones are often quite potent; however, the use of peptide antagonists is typically associated with problems because peptides are degraded by physiological enzymes and often poorly distributed within the organism being treated. Thus, they have limited effectiveness as drugs. Consequently, there presently exists a need for non-peptide antagonists of the peptide hormone GnRH.

SUMMARY OF THE INVENTION

An object of the invention is therefore to provide non-peptide compounds that are GnRH agents (agonists or antagonists) that bind to GnRH receptors and thus modulate activity, especially those that are potent GnRH antagonists. Another object of the invention is to provide effective therapies for individuals needing therapeutic regulation of GnRH and to provide methods for treating diseases and conditions mediated by GnRH regulation.

Such objects have been achieved by the non-peptide GnRH compounds of the invention, which are useful as pharmaceuticals for indications mediated by GnRH regulation. The inventive compounds are pharmaceutically advantageous over peptide compounds since they provide better biodistribution and tolerance to degradation by physiological enzymes. The invention further provides methods of synthesizing the compounds as well as intermediate compounds useful for making the compounds. GnRH agents of the invention are of the general Formula I:

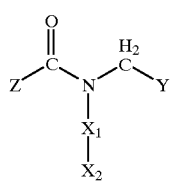

(I)

wherein:

Z is a group selected from substituted and unsubstituted alkyl, alkenyl, alkynyl, cycloalkyl, heterocycle, aryl, heteroaryl, $CH_2OR$, and $C(O)OR$, where R is substituted or unsubstituted alkyl, alkenyl, alkynyl, cycloalkyl, aryl, or heteroaryl, and where the total number of carbon atoms present in Z, not including optional substituents, ranges from 1 to 12;

Y is a lipophilic group selected from substituted and unsubstituted alkyl, alkenyl, alkynyl, cycloalkyl, aryl, and heteroaryl, where the total number of carbon atoms present in Y, not including optional substituents, ranges from 6 to 20;

$X_1$ is a structural unit, or spacer, used to connect the $CH_2NC(O)$, $X_2$, Y, and Z functional units in 3-dimensional space, that is selected from substituted and unsubstituted alkyl, alkenyl, alkynyl, cycloalkyl, aryl, and heteroaryl such that the atom count in the chain portion of the unit linking the central nitrogen (the N atom in Formula I is referred to as the "central nitrogen" to avoid confusion with any other nitrogen-bearing substituents) to $X_2$ ranges from 3 to 8, preferably from 4 to 6; and $X_2$ is a basic group having a $pK_a$ greater than about 8 that is preferably selected from substituted and unsubstituted guanidinyl, amidinyl, acylamidinyl, azetidinyl, and amino.

In addition to compounds of the Formula I, GnRH agents of the invention include pharmaceutically acceptable salts, multimeric forms, prodrugs, and active metabolites of compounds of the Formula I. Such non-peptide agents are pharmaceutically advantageous over peptide agents since they provide better biodistribution and tolerance to degradation by physiological enzymes.

The invention also relates to pharmaceutical compositions comprising a therapeutically effective amount of a GnRH agent of the invention in combination with a pharmaceutically acceptable carrier or diluent. Moreover, the invention relates to methods for regulating the secretion of gonadotropins in mammals, comprising administering therapeutically effective amounts of GnRH agents of the invention.

The invention further relates to processes for synthesizing the compounds as well as to intermediate compounds useful for making the compounds. Intermediate compounds useful for making compounds of the Formula I are those encompassed by the following Formulae II, III, and IV:

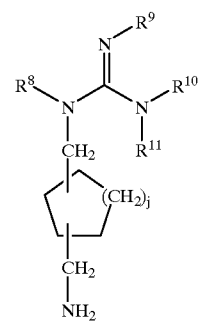

(II)

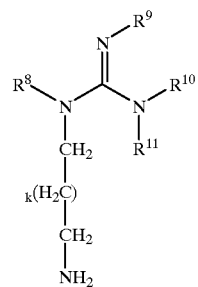

(III)

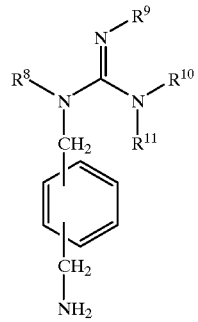

(IV)

wherein:
j is 1 or 2;
k is 1, 2, 3, 4 or 5;
$R^8$ is H or substituted or unsubstituted lower alkyl;
$R^9$ is H or substituted or unsubstituted lower alkyl, CN, $NO_2$ or $CO_2R^1$;
$R^{10}$ is H or substituted or unsubstituted lower alkyl, $CH_2OR^1$, $(CH_2)_pOR^1$, $CO_2R^1$, or $(CH_2)_pC(O)R^2$, where p is an integer from 1 to 6, and $R^2$ is H, $OR^1$, $SR^1$, $N(R^1)_2$, or $C(R^1)_3$;
$R^{11}$ is H or substituted or unsubstituted lower alkyl, $CH_2O$-phenyl, $CH_2O$-benzyl, phenyl, or benzyl;
or any two of $R^8$, $R^9$, $R^{10}$, and $R^{11}$ ($R^8$ and $R^9$, or $R^8$ and $R^{11}$, or $R^8$ and $R^{10}$, or $R^9$ and $R^{10}$, or $R^9$ and $R^{11}$, or $R^{10}$ and $R^{11}$) taken together form a 5- or 6-membered heterocycle;
and where each $R^1$ is independently selected from H and substituted or unsubstituted lower alkyl, O-lower alkyl, and S-lower alkyl.

Other features, objects, and advantages of the invention will become apparent from the following detailed description of the invention and its preferred embodiments.

Figure 1:
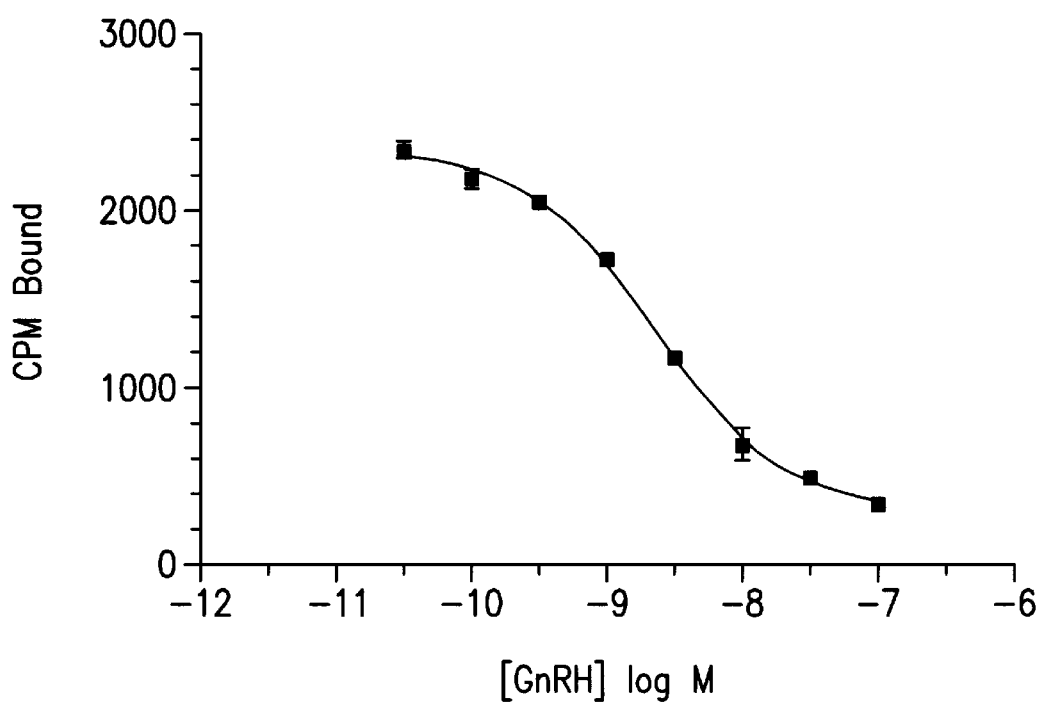
FIG. 1 is a plot of a displacement curve derived from measurements of the amount of radiolabeled GnRH bound to membranes bearing GnRH receptors versus concentration of unlabeled GnRH.

DETAILED DESCRIPTION AND PREFERRED EMBODIMENTS OF THE INVENTION GnRH Agents

Some of the compounds of the invention contain one or more centers of asymmetry, and may thus give rise to enantiomers, diastereoisomers, and other stereoisomeric forms. The invention is meant to include all such possible stereoisomers as well as their racemic and optically pure forms. When the compounds described herein contain olefinic double bonds, they are intended to encompass both E and Z geometric isomers.

The chemical formulae referred to herein may exhibit the phenomenon of tautomerism. As the structural formulae shown in this specification only depict one of the possible tautomeric forms, it should be understood that the invention nonetheless encompasses all tautomeric forms.

The term "alkyl" refers to straight- and branched-chain alkyl groups having one to twelve carbon atoms. Exemplary alkyl groups include methyl (Me), ethyl, n-propyl, isopropyl, butyl, isobutyl, sec-butyl, tert-butyl (tBu), pentyl, isopentyl, tert-pentyl, hexyl, isohexyl, and the like. The term "lower alkyl" designates an alkyl having from 1 to 8 carbon atoms (a $C_{1-8}$-alkyl). Suitable substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like.

The term "alkenyl" refers to straight- and branched-chain alkenyl groups having from 2 to 12 carbon atoms. Illustrative alkenyl groups include prop-2-enyl, but-2-enyl, but-3-enyl, 2-methylprop-2-enyl, hex-2-enyl, and the like.

The term "alkynyl" refers to straight- and branched-chain alkynyl groups having from 2 to 12 carbons atoms. Exemplary alkynyls include prop-2-ynyl, 3-methylpent-4-ynyl, hex-2-ynyl, and the like.

The term "carbocycle" refers to a monocyclic or polycyclic carbon ring structure (with no heteroatoms) having from 3 to 7 carbon atoms in each ring, which may be saturated, partially saturated, or unsaturated. Exemplary carbocycles include cycloalkyls and aryls.

The term "heterocycle" refers to a monocyclic or polycyclic ring structure with one or more heteroatoms selected from N, O, and S, and having from 3 to 7 atoms (carbon atoms plus any heteroatom(s)) in each ring, which may be saturated, partially saturated, or unsaturated. Exemplary heterocycles include tetrahydrofuranyl, tetrahydropyranyl, azetidinyl, pyrrolidinyl, piperidinyl, piperazinyl, and the like.

The term "cycloalkyls" as used herein refers to saturated carbocycles having 3 to 12 carbons, including bicyclic and tricyclic cycloalkyl structures. Suitable cycloalkyls include cyclopropyl, cyclobutyl, cyclopentyl, cyclohexyl, cycloheptyl, and the like.

The terms "aryls" and "heteroaryls" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like. Such moieties may be optionally substituted by one or more suitable substituents, for example, a substituent selected from a halogen (F, Cl, Br and I); lower alkyl; OH; $NO_2$; CN; $CO_2H$; O-lower alkyl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused ring structure or bridge, for example $OCH_2$—O.

The term "aryl-lower alkyl" means a lower alkyl bearing an aryl. Examples include benzyl, phenethyl, pyridylmethyl, naphthylmethyl, and the like. The aryl-lower alkyl may be optionally substituted.

In general, the various moieties or functional groups for $X_1$, $X_2$, Y, and Z in Formula I may be optionally substituted by one or more suitable substituents. Exemplary substituents include a halogen (F, Cl, Br, or I), lower alkyl, —OH, —$NO_2$, —CN, —$CO_2H$, —O-lower alkyl, -aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O-haloalkyl (e.g., —$OCF_3$, —$OCHF_2$), and the like.

"Protecting groups" refer to groups that protect one or more inherent functional groups from premature reaction. Suitable protecting groups may be routinely selected by those skilled in the art in light of the functionality and particular chemistry used to construct the compounds. Examples of suitable protecting groups are described, for example, in Greene and Wutz, *Protecting Groups in Organic Synthesis*, 2nd edition, John Wiley & Sons, New York, N.Y. (1991). Exemplary protecting groups useful in the practice of the invention include tert-butoxycarbonyl (Boc) and the like.

Compounds of the invention useful as GnRH agents are of the following Formula I:

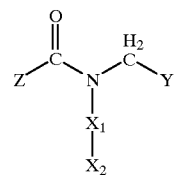

(I)

wherein:

Z is a group selected from substituted and unsubstituted alkyl, alkenyl, alkynyl, cycloalkyl, heterocycle, aryl, heteroaryl, $CH_2OR$, and $C(O)OR$, where R is substituted or unsubstituted alkyl, alkenyl, alkynyl, cycloalkyl, aryl, or heteroaryl, and where the total number of carbon atoms present in Z, not including optional substituents, ranges from 1 to 12;

Y is a lipophilic group selected from substituted and unsubstituted alkyl, alkenyl, alkynyl, cycloalkyl, aryl, and heteroaryl, where the total number of carbon atoms present in Y, not including optional substituents, ranges from 6 to 20;

$X_1$ is a structural unit, or spacer, used to connect the $CH_2NC(O)$, $X_2$, Y, and Z functional units in 3-dimensional space, that is selected from substituted and unsubstituted alkyl, alkenyl, alkynyl, cycloalkyl, aryl, and heteroaryl such that the atom count in the chain portion of the unit linking the central nitrogen (the N atom in Formula I is referred to as the "central nitrogen" to avoid confusion with any other nitrogen-bearing substituents) and $X_2$ ranges from 3 to 8, preferably from 4 to 6; and $X_2$ is a basic group having a $pK_a$ greater than about 8, preferably one selected from substituted and unsubstituted guanidinyl, amidinyl, acylamidinyl, azetidinyl, and amino; and pharmaceutically acceptable salts, prodrugs, pharmaceutically active metabolites, and mimeric forms of such compounds.

Additionally, Formula I is intended to cover, where applicable, solvated as well as unsolvated forms of the compounds. Thus, Formula I includes compounds having the indicated structure, including the hydrated as well as the non-hydrated forms.

Preferred Z groups include: substituted and unsubstituted furyls, for example, 2-furyl, 3-furyl, 5-methyl-2-furyl, and 5-nitro-2-furyl; substituted and unsubstituted pyrrolyl; substituted and unsubstituted naphthyls, for example, 1-naphthyl and 2-naphthyl; substituted and unsubstituted thienyls, e.g., 2-thienyl; substituted and unsubstituted pyridyls, for example, 2-chloropyrid-5-yl and 2-methylthiopyrid-3-yl; substituted and unsubstituted cycloalkyls, for example, cyclopropyl, cyclobutyl, cyclopentyl, and cyclohexyl; and substituted and unsubstituted lower alkyls, such as methyl, ethyl, propyl, butyl, and the like, with those substituted with fluorine, e.g., $CF_3$, being especially preferred. Especially preferred Z groups include furyls, pyrrolyls, thienyls, and $CF_3$.

Preferred Y groups include: substituted and unsubstituted phenyl, for example 4-isopropylphenyl, 4-N,N-dimethylaminopropyloxyphenyl, 2,4,5-triethoxyphenyl, 2,3-dibenzyloxyphenyl, and 2-(4'-chlorophenyloxy)phenyl; substituted and unsubstituted naphthyl and its partially or fully saturated derivatives, for example, 1,2,3,4-tetrahydro-1,1,4,4,6-pentamethylnaphthalene; substituted and unsubstituted dibenzylfuryl and its saturated and partially saturated derivatives; substituted and unsubstituted quinolinyl, isoquinolinyl, quinoxalinyl, and the like, for example, 3-quinolinyl; and substituted and unsubstituted cycloalkyls and fused polycyclic alkyls. Lipophilic groups that are bulky are particularly preferred Y groups, especially one of the following groups:

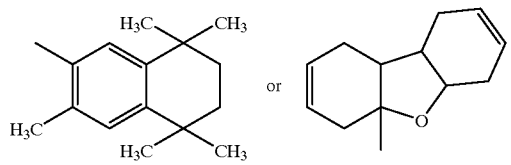

Preferred $X_1$ groups include alkylene, alkylene-cycloalkyl-alkylene, and alkylene-aryl-alkylene chains, where the term "alkylene" refers to $(CH_2)_n$, where n is an integer ranging from 1 to 6. Especially preferred $X_1$ groups include the following:

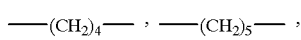

-continued

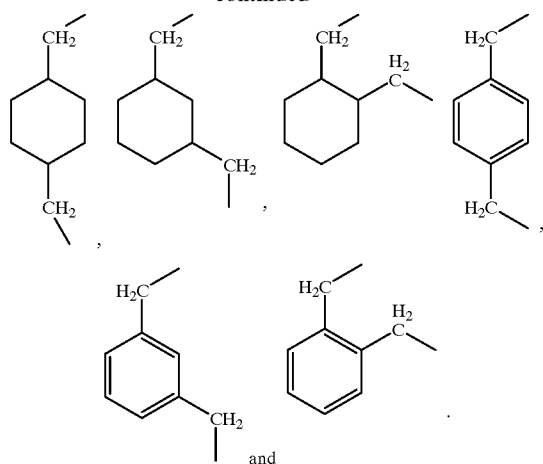

Preferred $X_2$ groups are highly basic, e.g., having a $pK_a$ greater than about 9, more preferably greater than about 10. Exemplary $X_2$ groups include guanidinyl, amidinyl, and amino, which may be unsubstituted or substituted with one or more lower alkyls. Especially preferred for $X_2$ is guanidinyl.

Preferred compounds include those encompassed by the following subgeneric Formulae I' and I" (where Y and Z are as defined above):

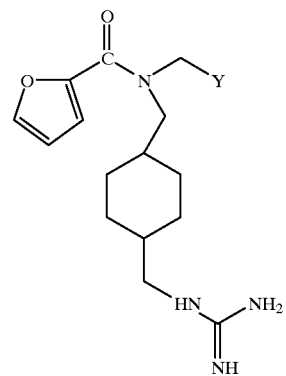

(I')

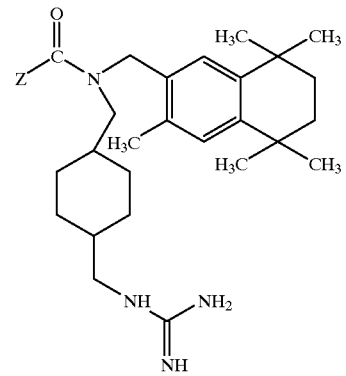

(I")

Preferred specific embodiments of compounds of the Formula I include the following Compound Nos. 1–120 (in the depictions below, alkyl and alkylene substituents are shown using a shorthand convention, e.g., "|" for a methyl group):

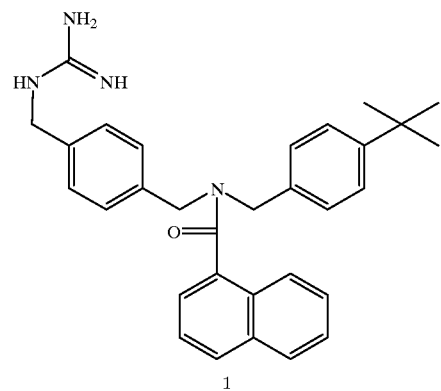
1
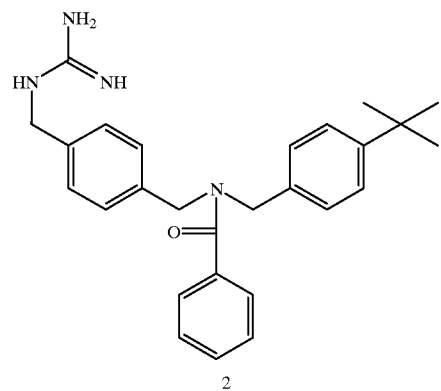
2
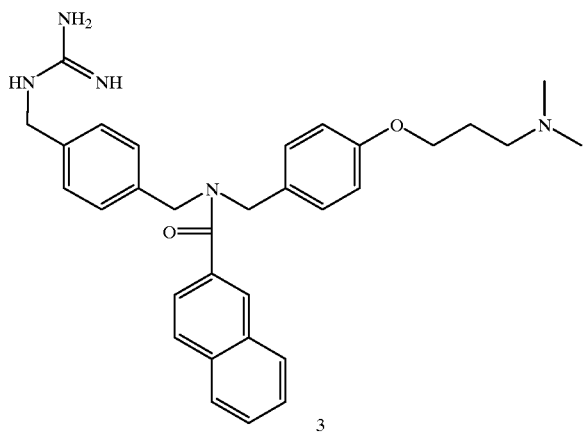
3
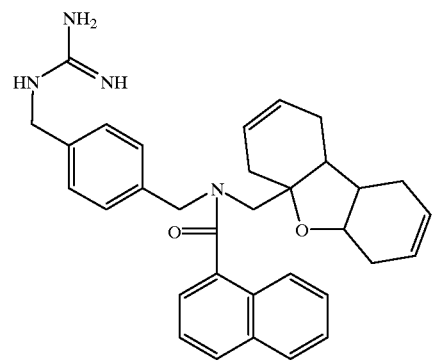
4
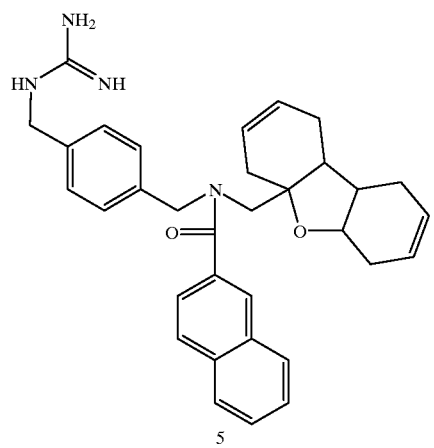
5
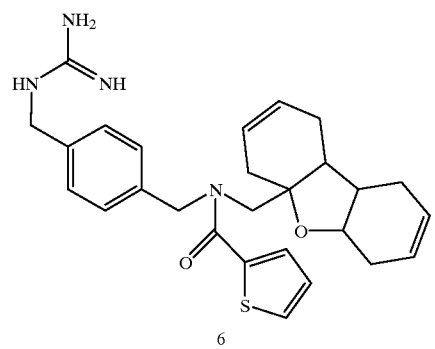
6
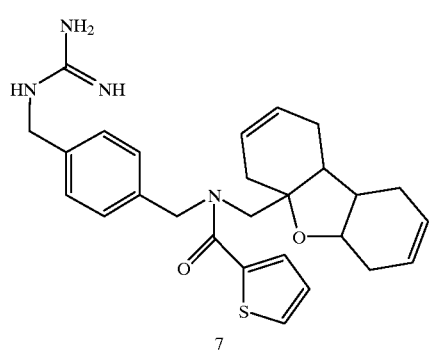
7
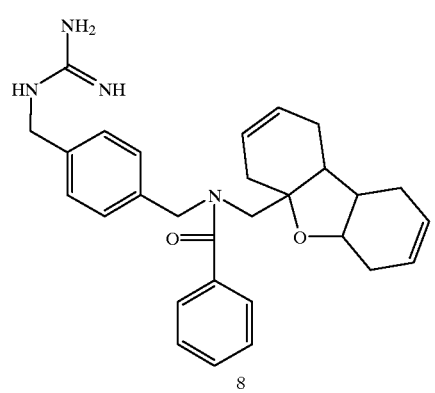
8

-continued
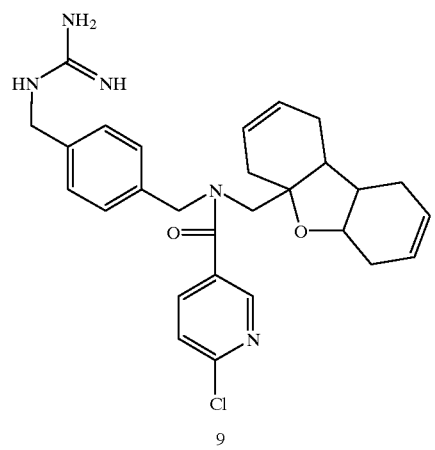
9
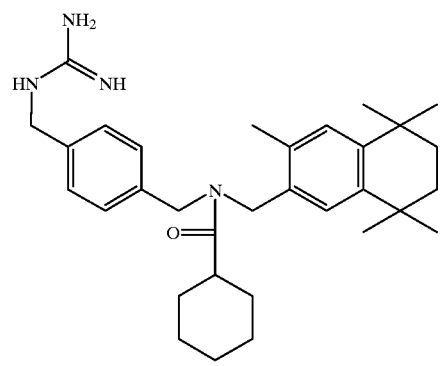
10
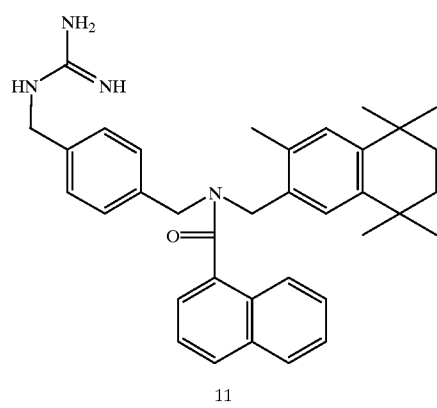
11
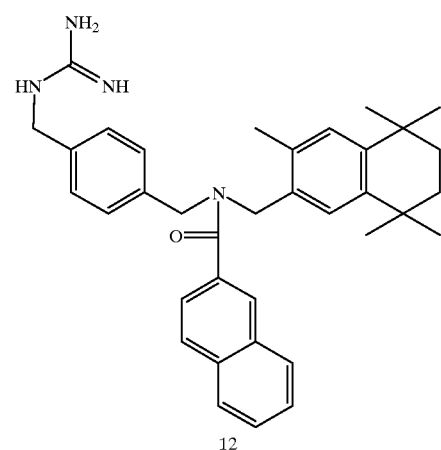
12
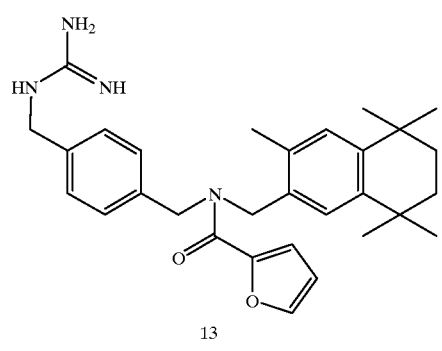
13
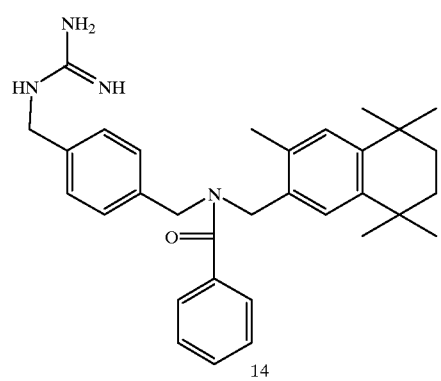
14
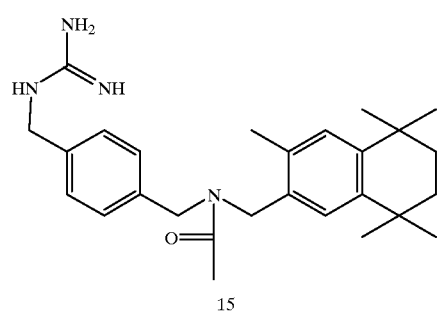
15
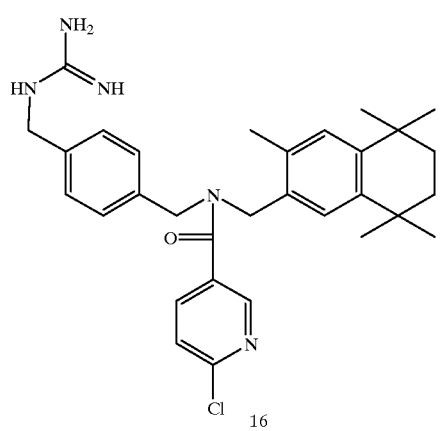
16

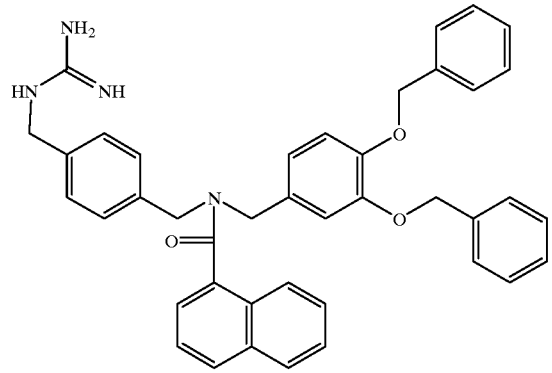
17
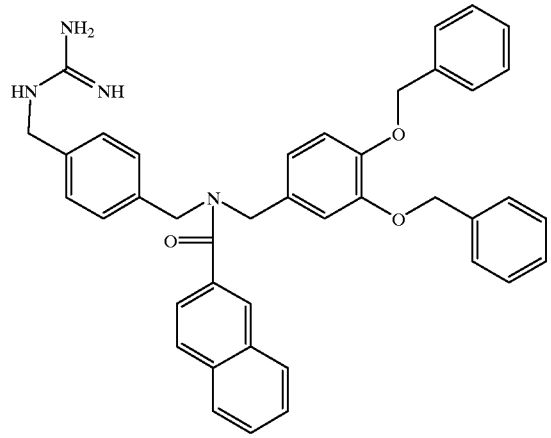
18
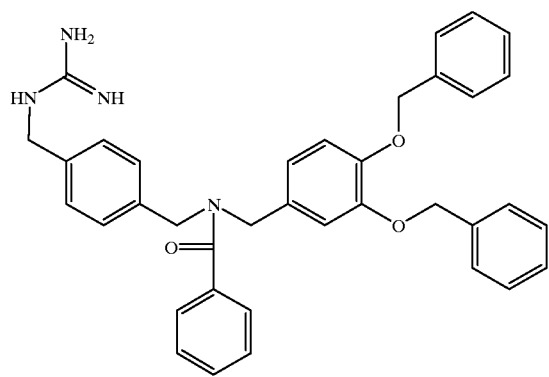
19
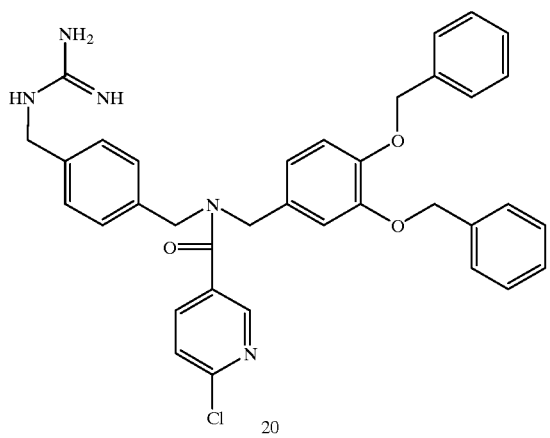
20
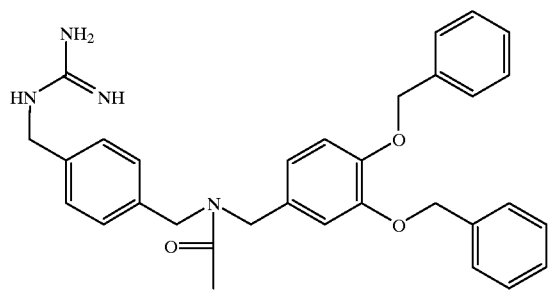
21
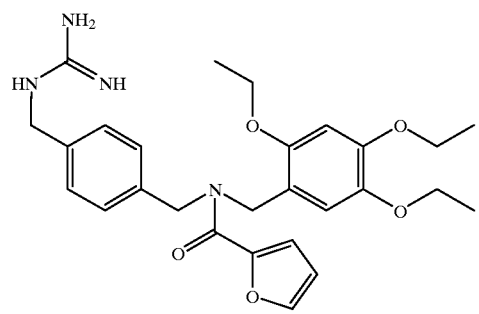
22
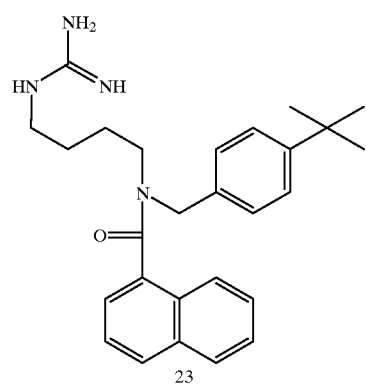
23
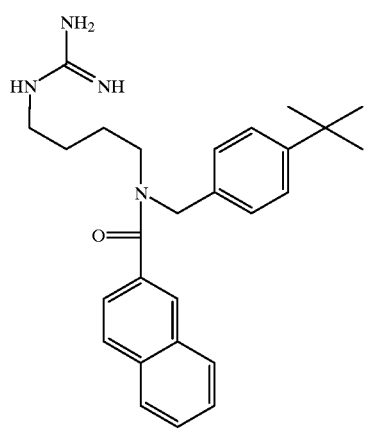
24

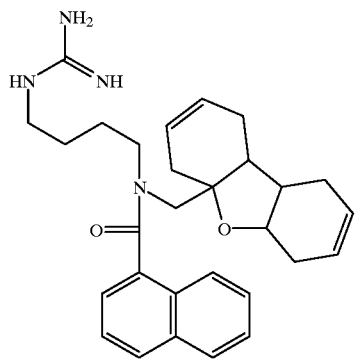
25
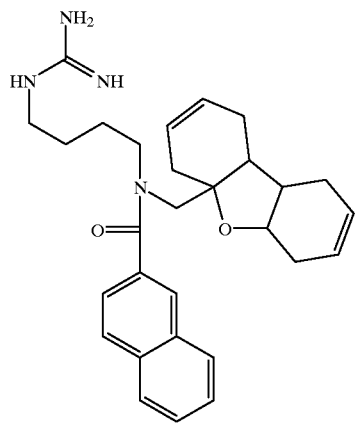
26
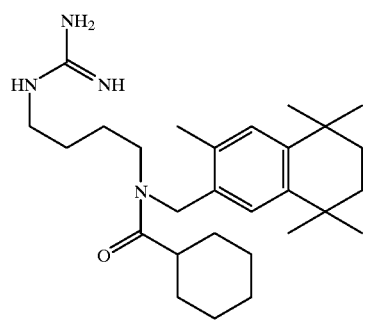
27
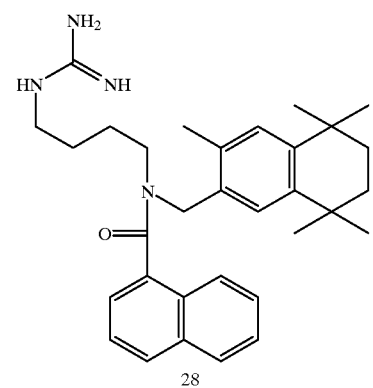
28
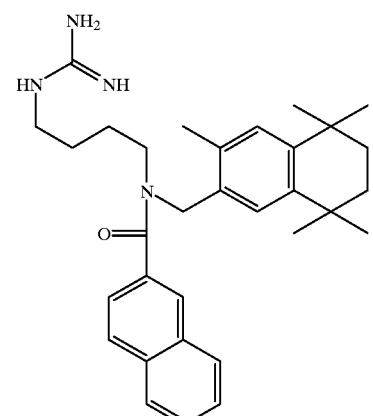
29
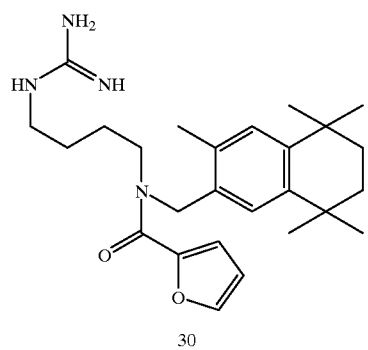
30
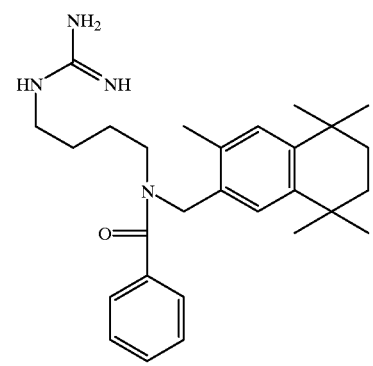
31
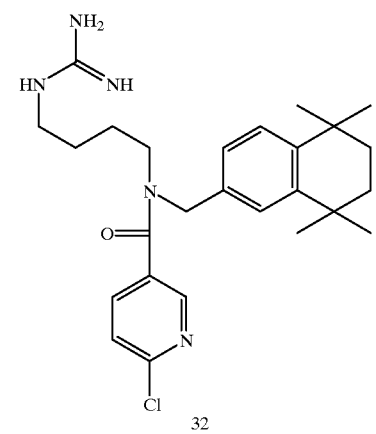
32
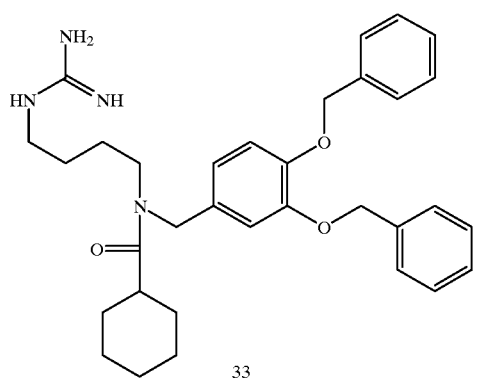
33
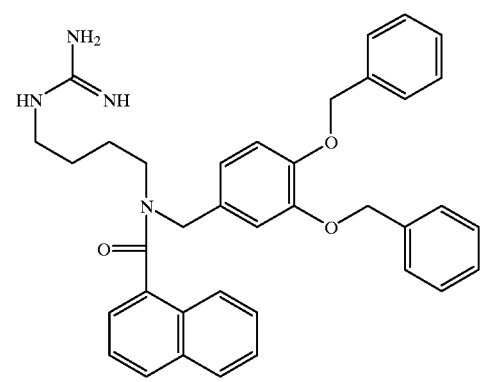
34

-continued
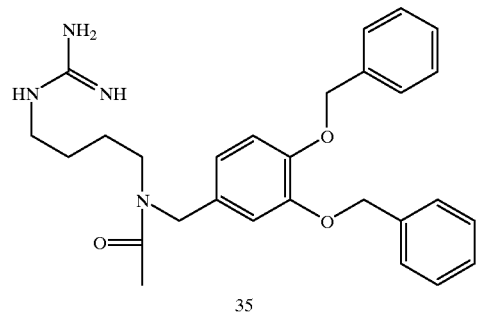
35
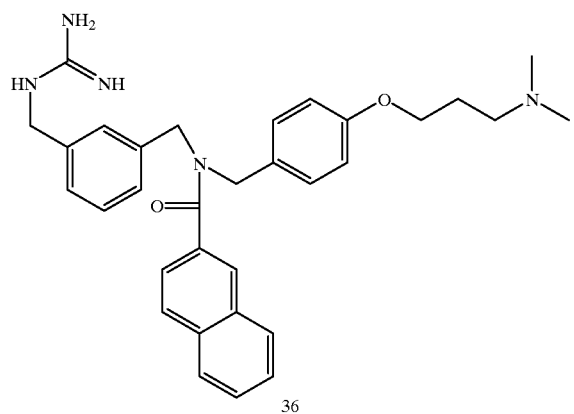
36
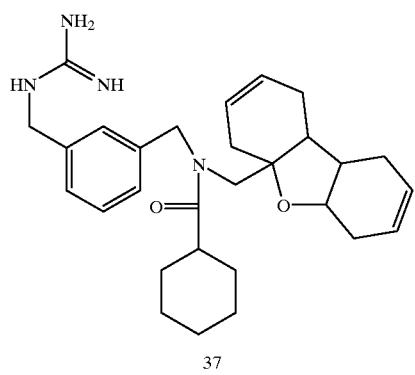
37
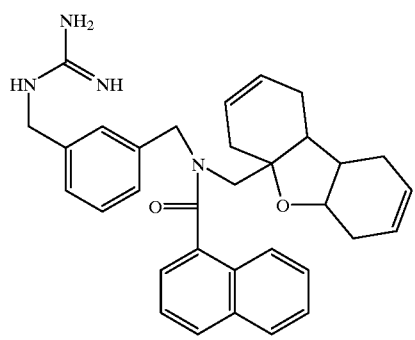
38
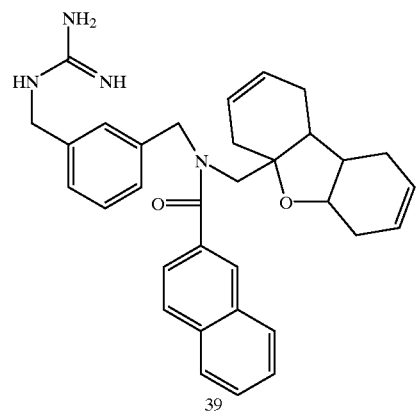
39
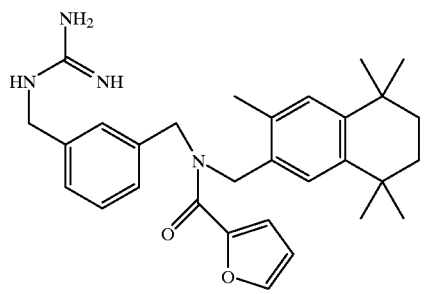
40
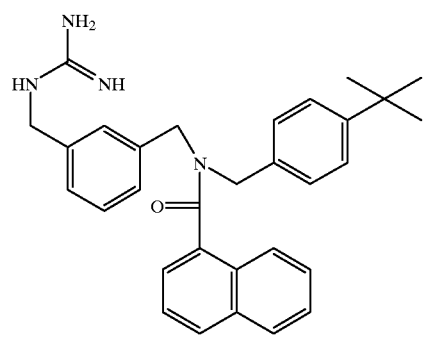
41
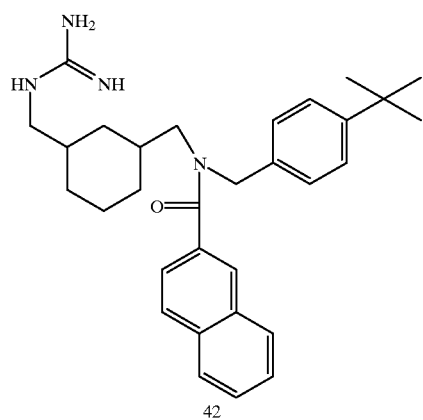
42

-continued
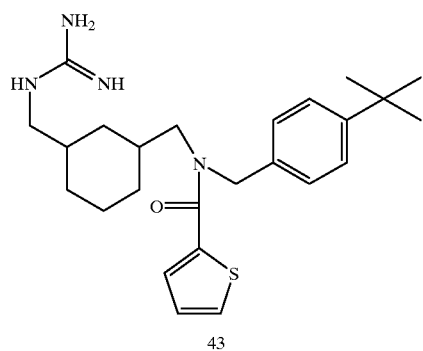
43
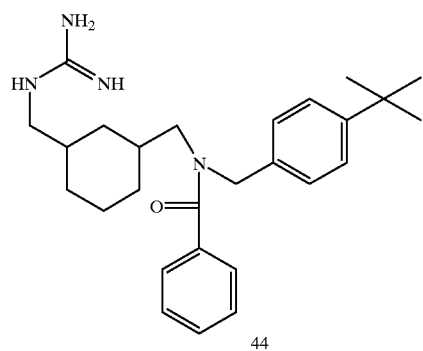
44
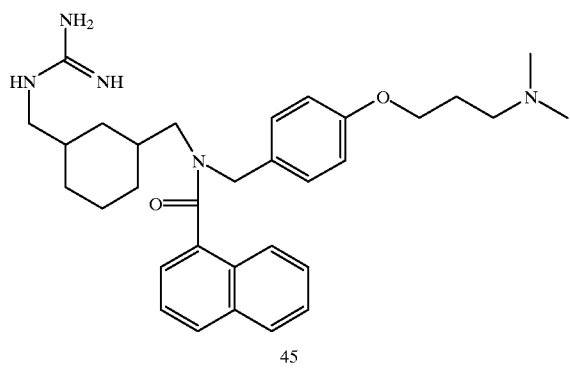
45
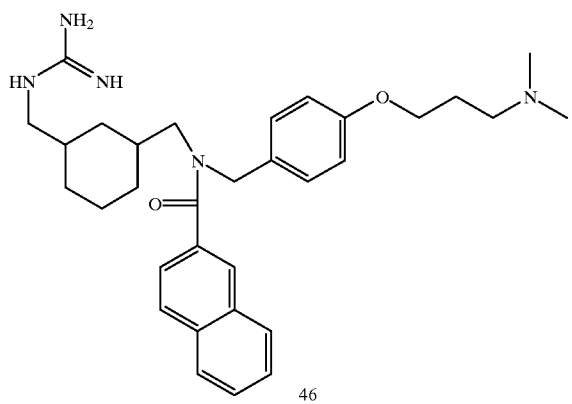
46
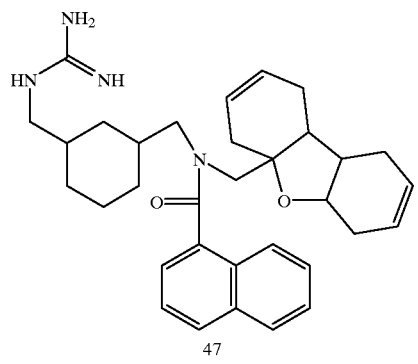
47
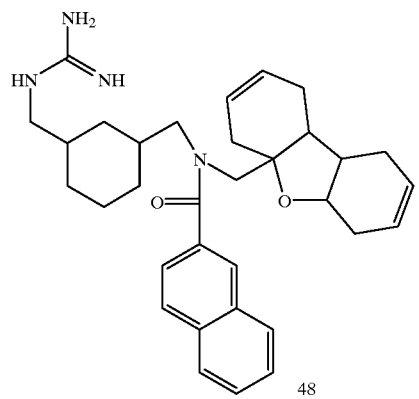
48
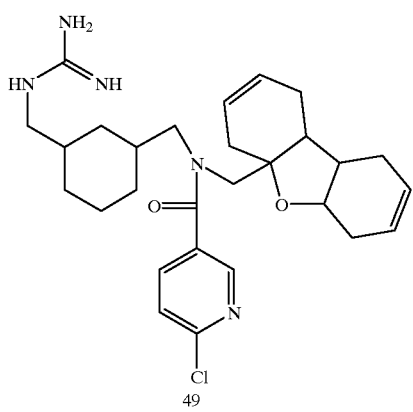
49
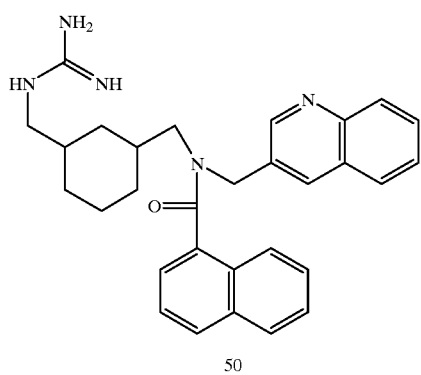
50

-continued
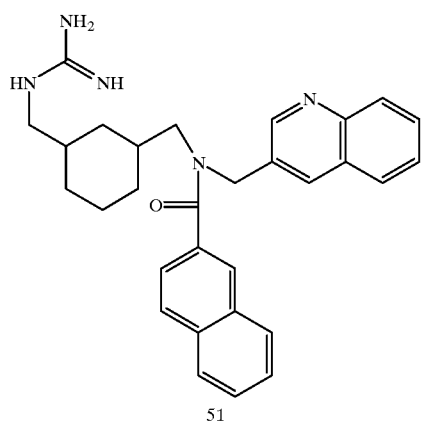
51
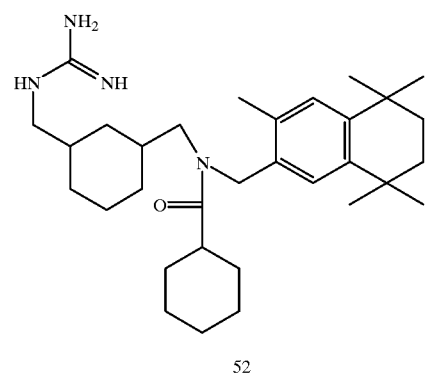
52
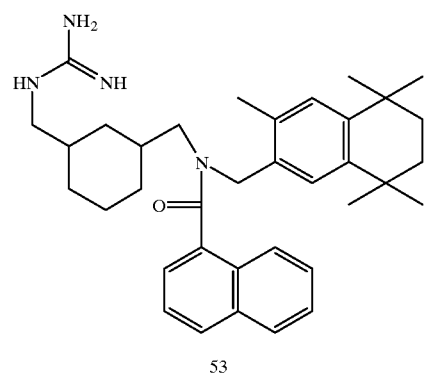
53
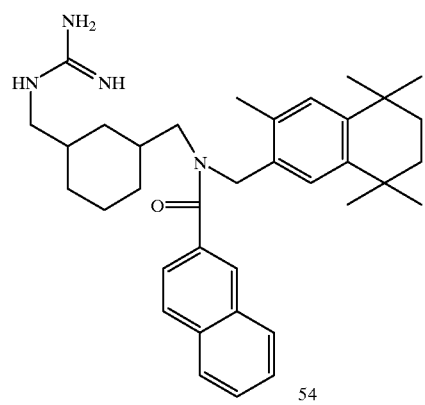
54
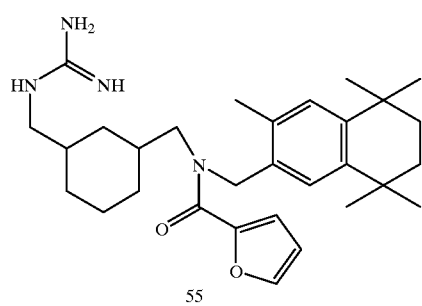
55
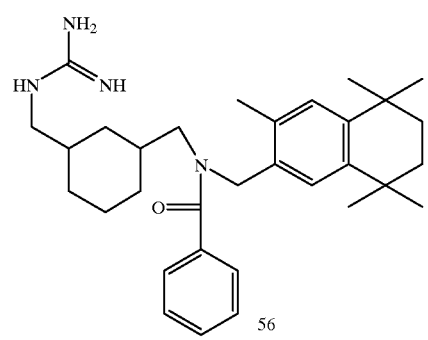
56
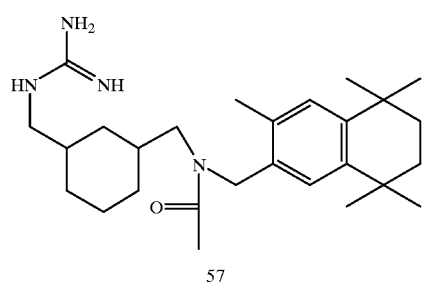
57
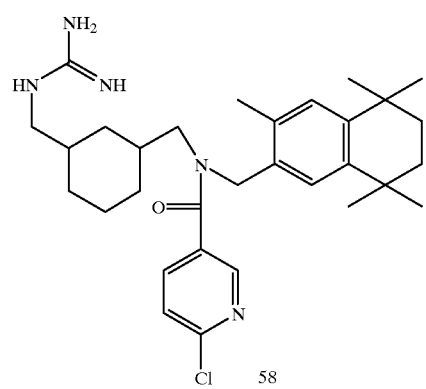
58

-continued
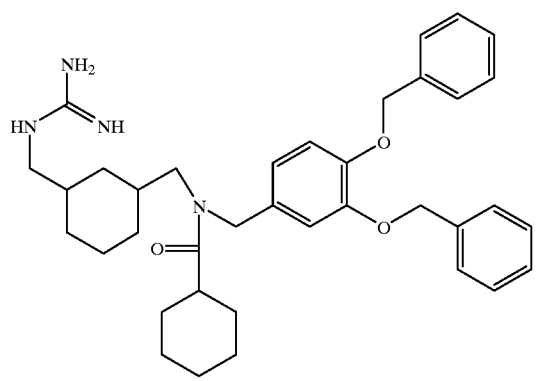
59
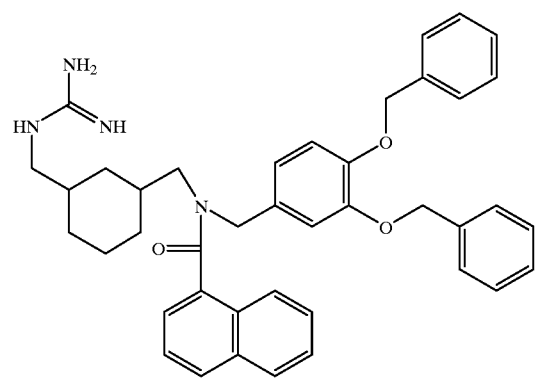
60
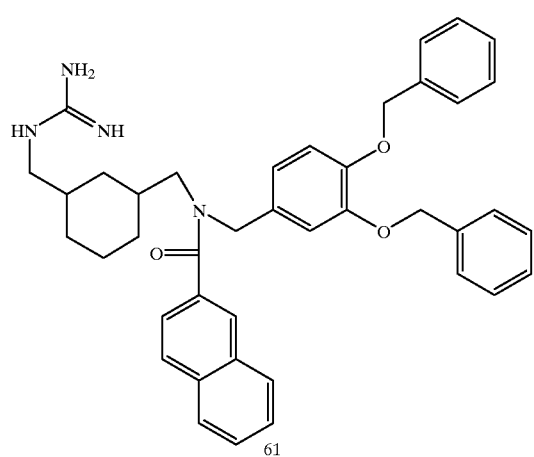
61
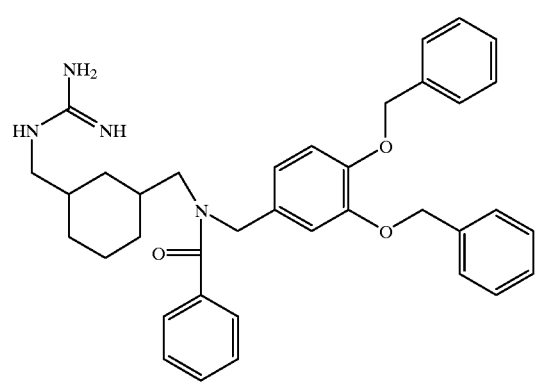
62
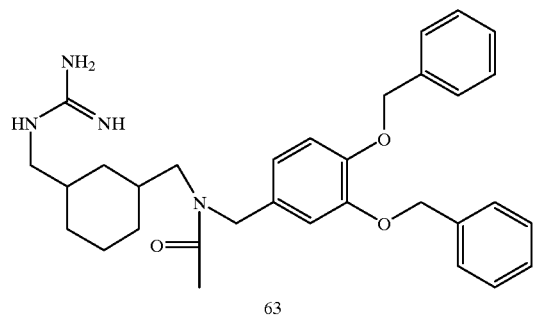
63
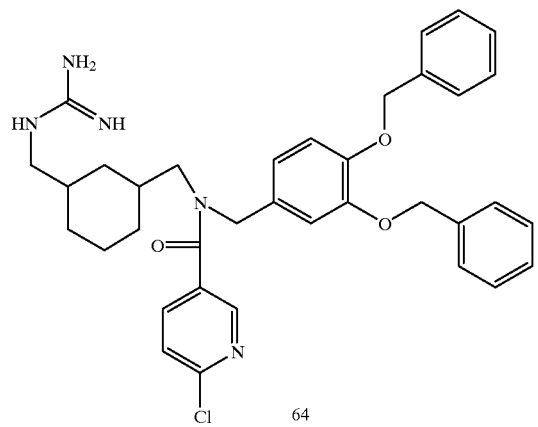
64
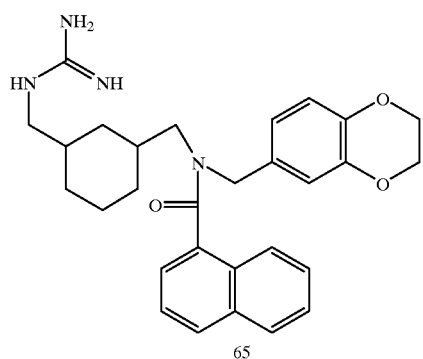
65
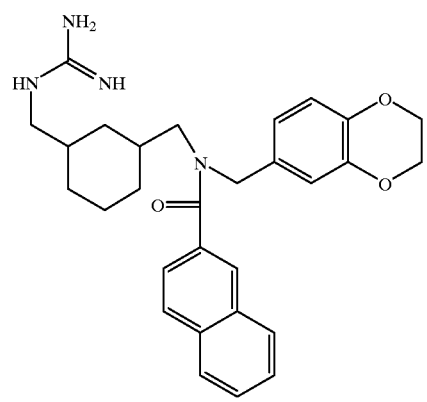
66

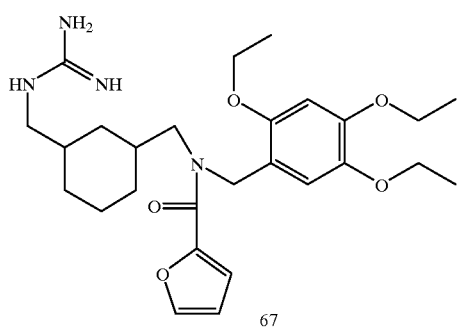
67
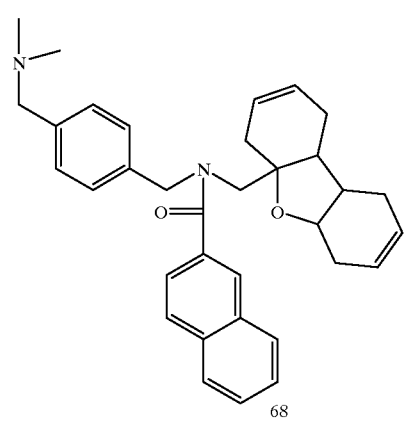
68
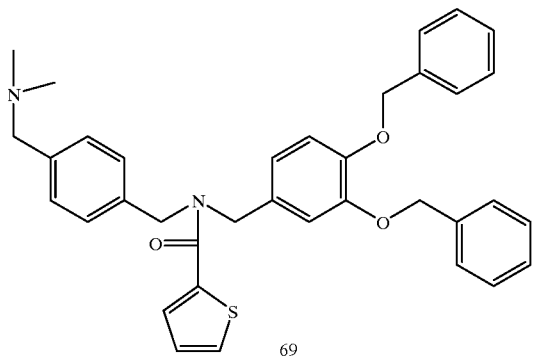
69
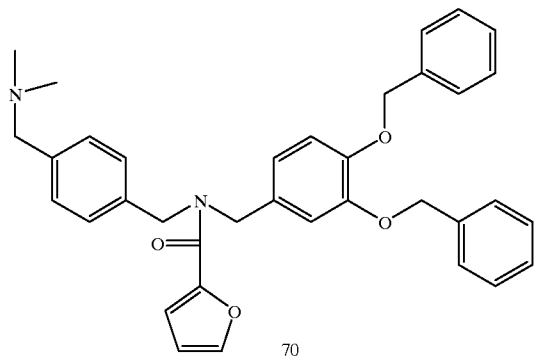
70
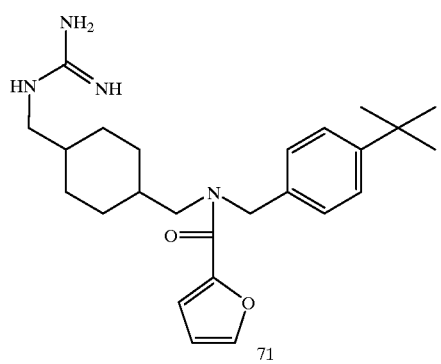
71
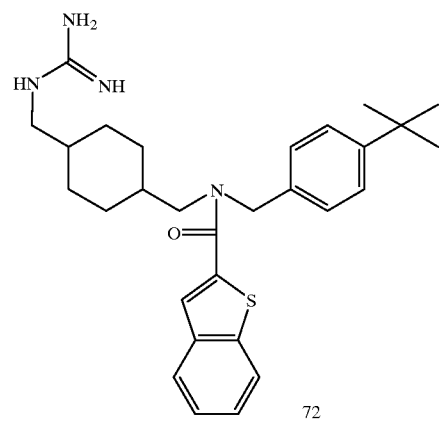
72
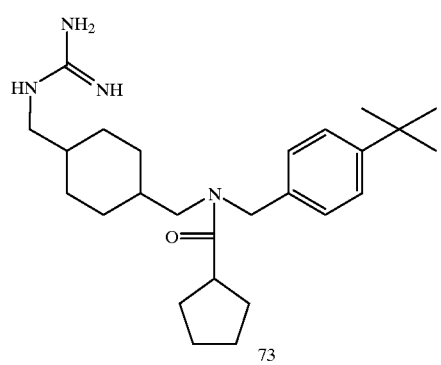
73
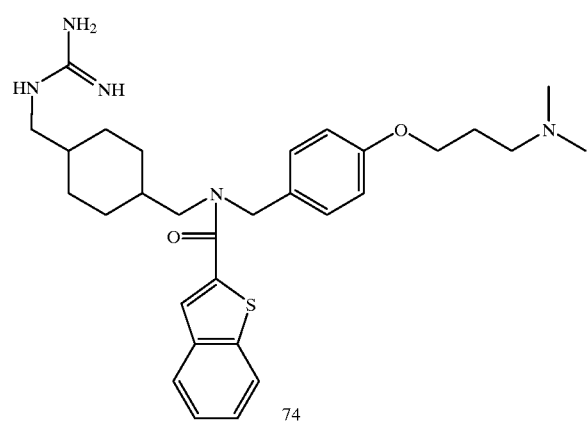
74

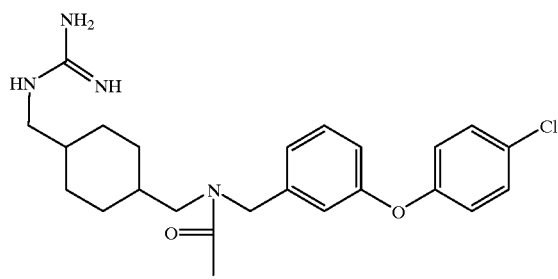
75
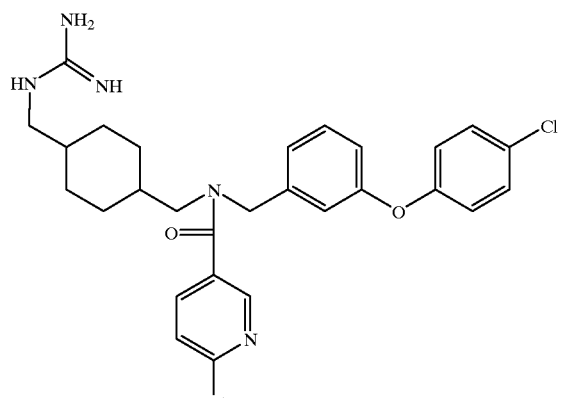
76
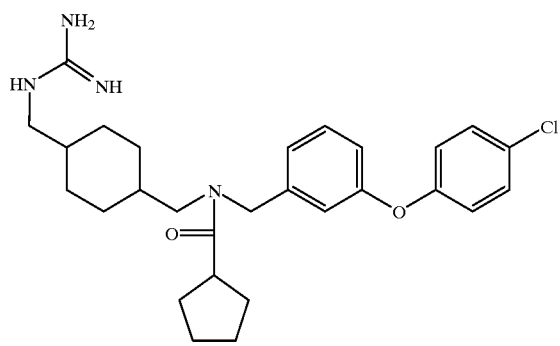
77
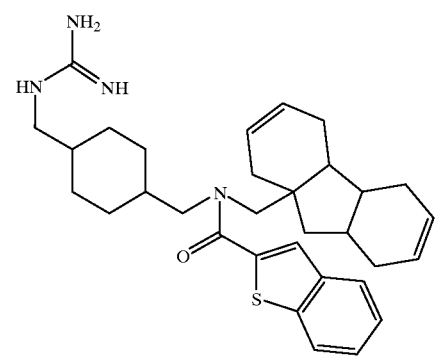
78
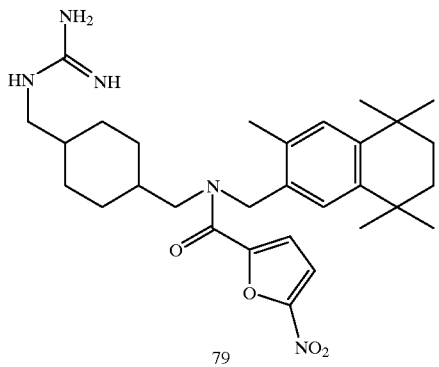
79
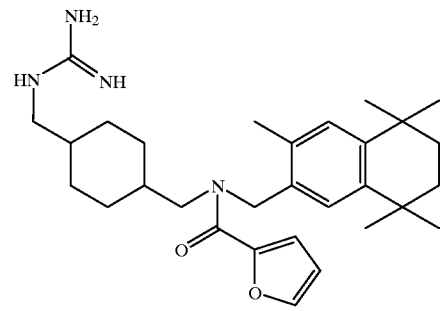
80
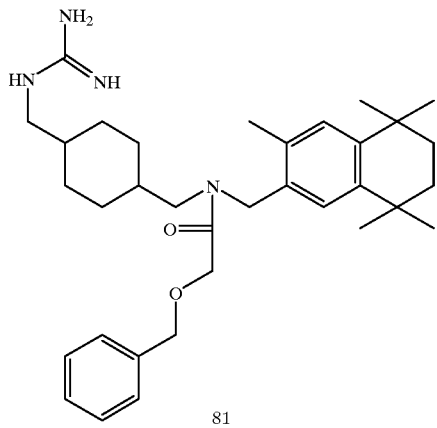
81
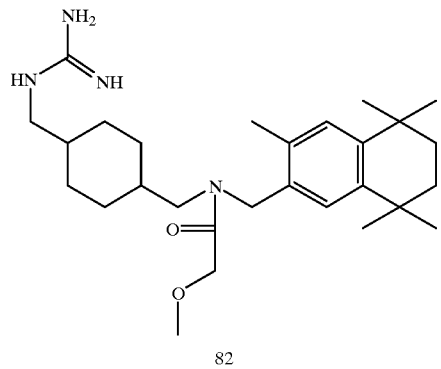
82

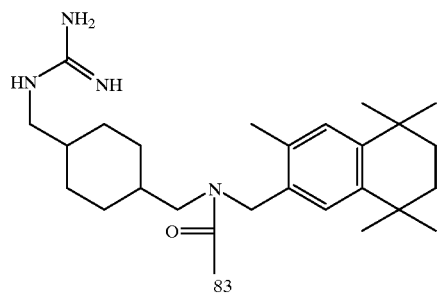
83
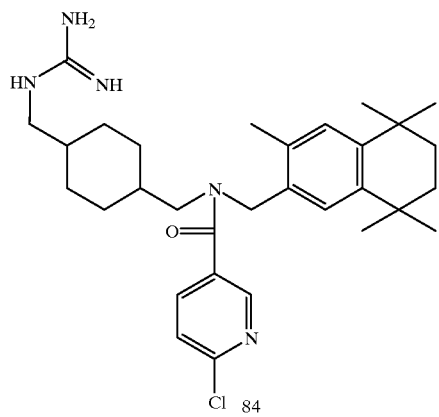
84
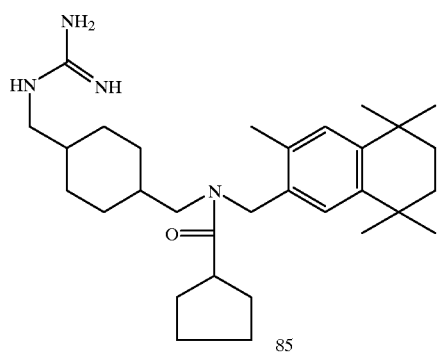
85
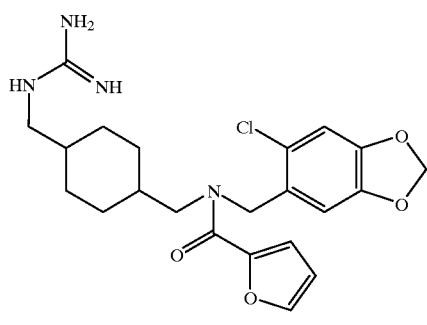
86
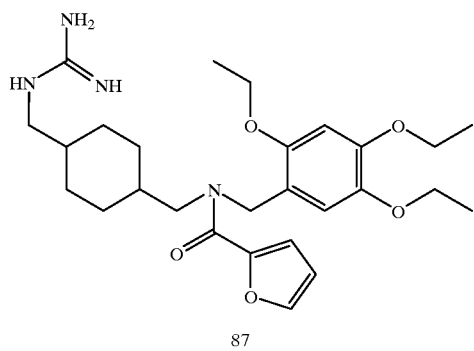
87
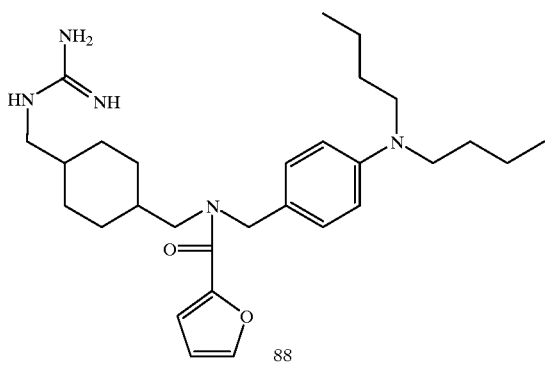
88
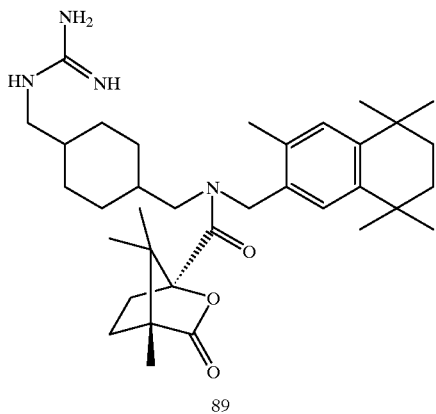
89
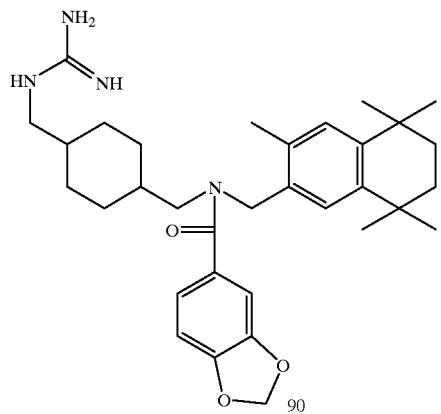
90

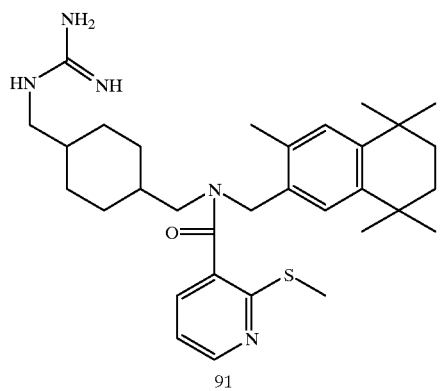
91
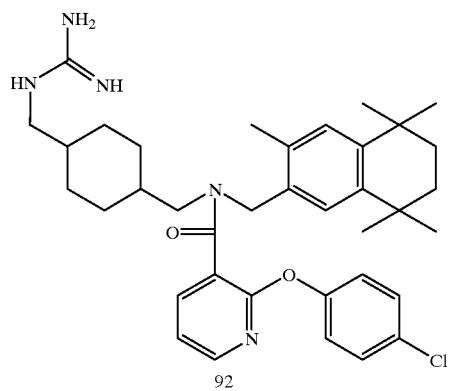
92
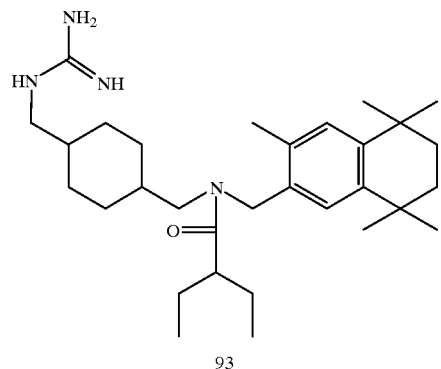
93
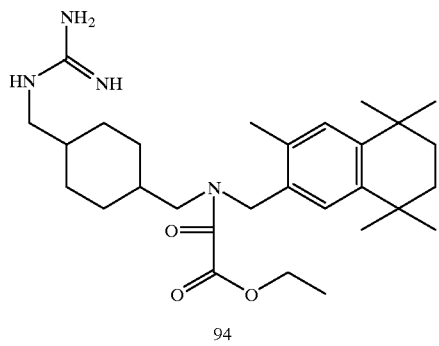
94
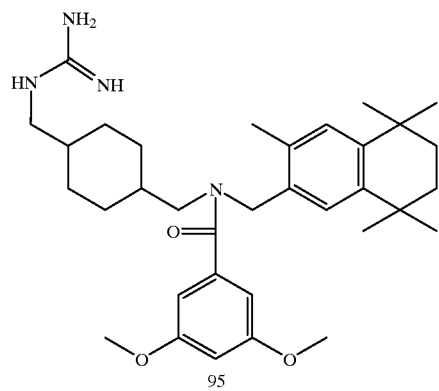
95
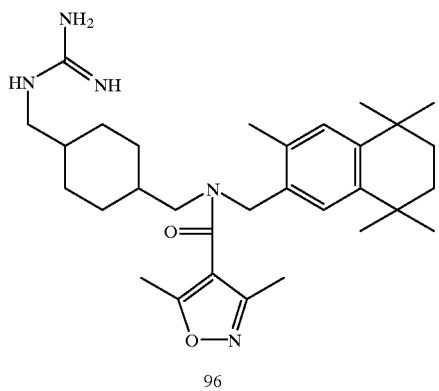
96
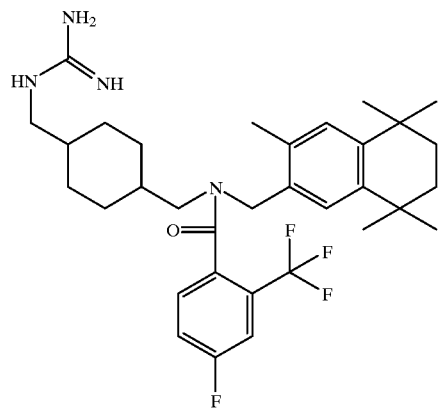
97
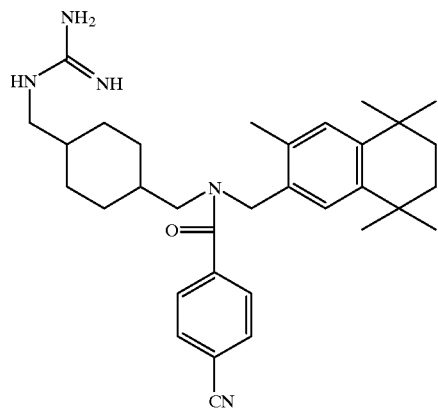
98

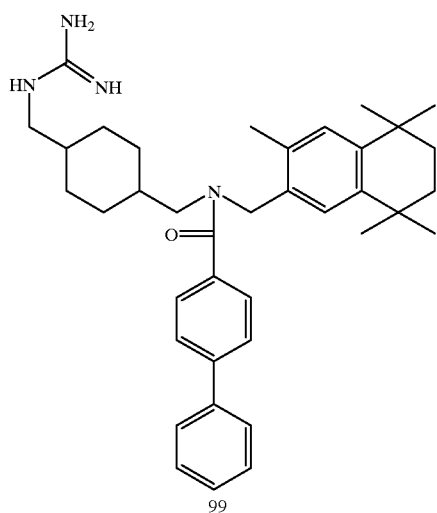
99
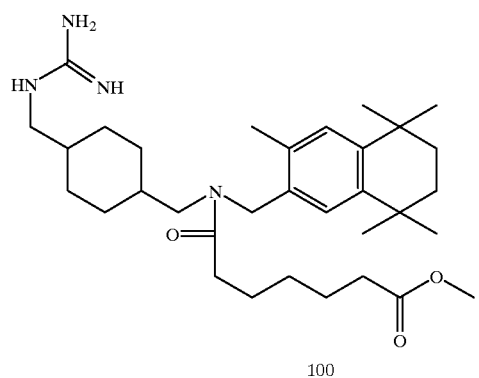
100
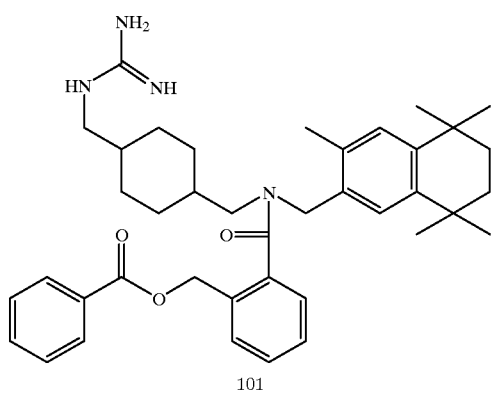
101
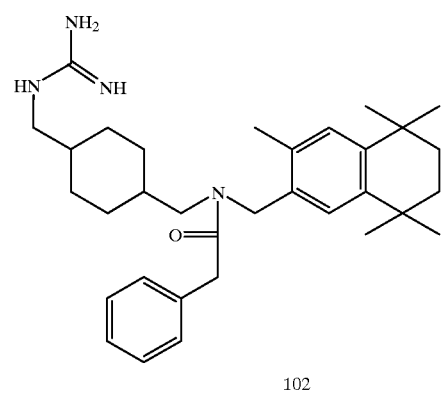
102
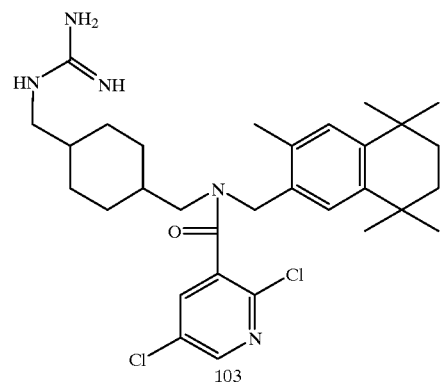
103
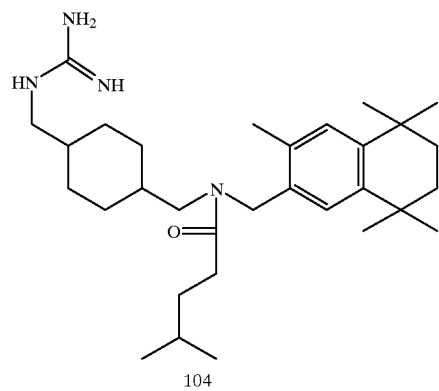
104
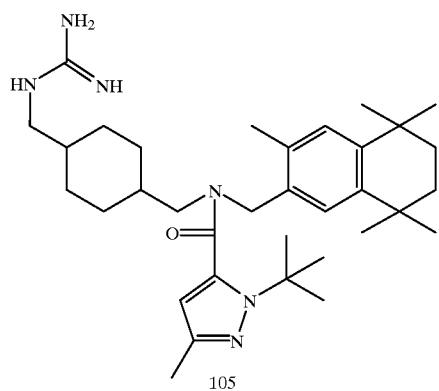
105
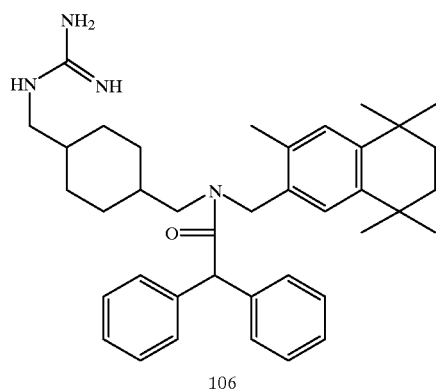
106

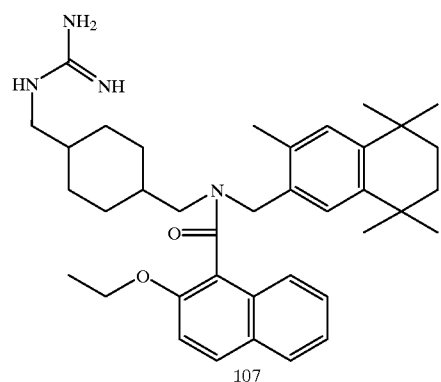
107
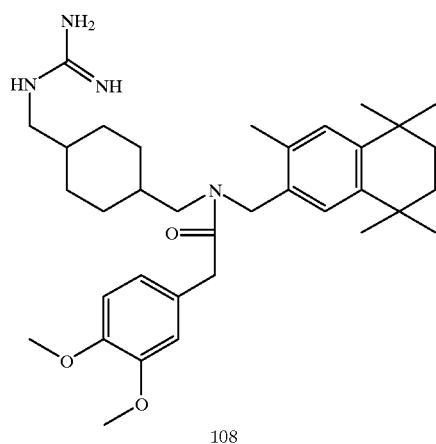
108
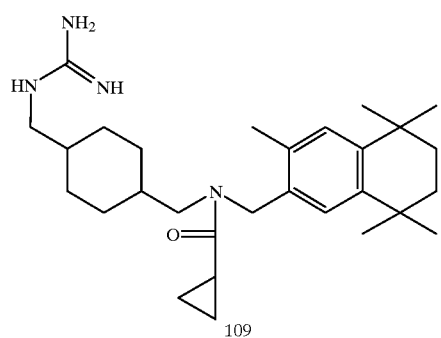
109
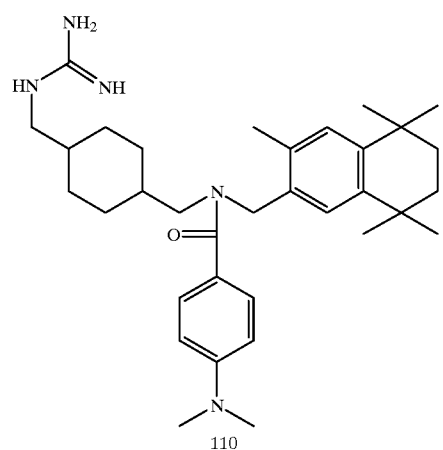
110
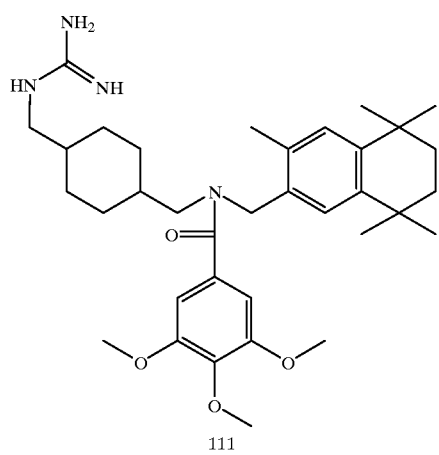
111
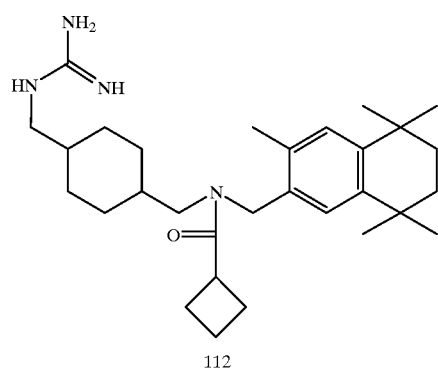
112

-continued
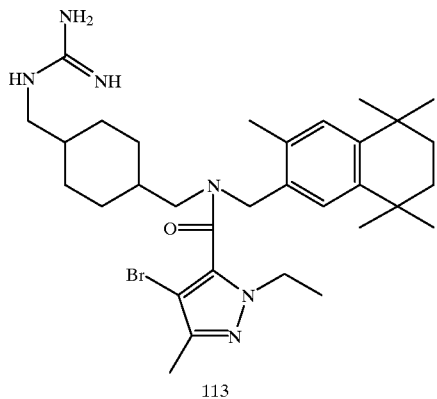
113
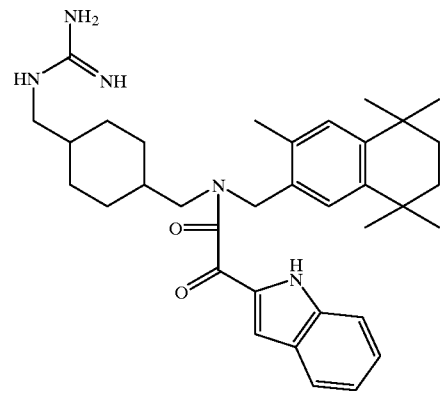
114
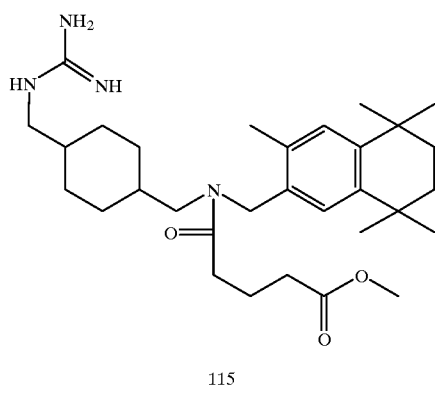
115
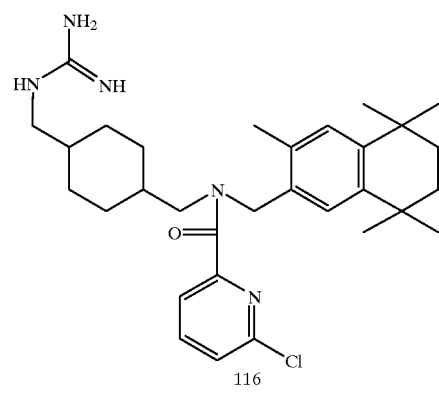
116
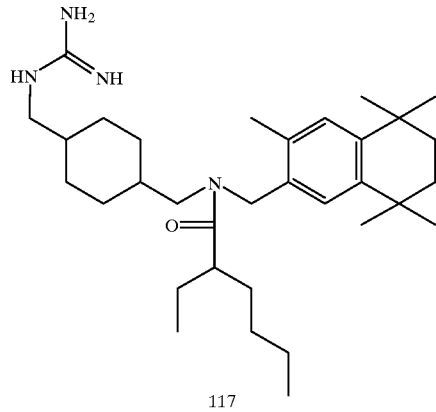
117
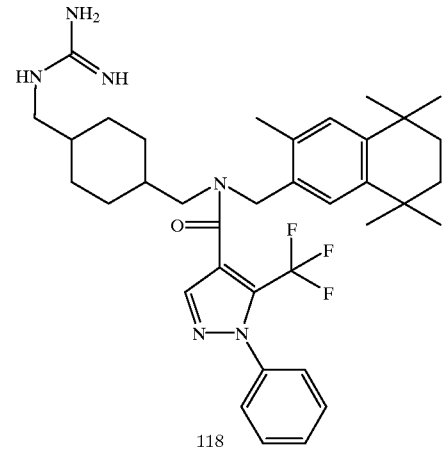
118
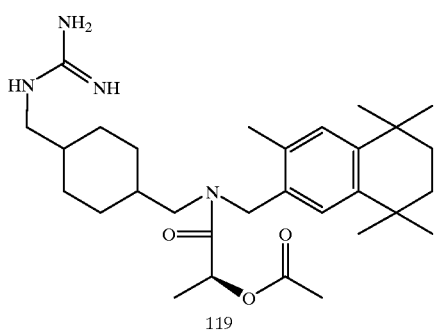
119
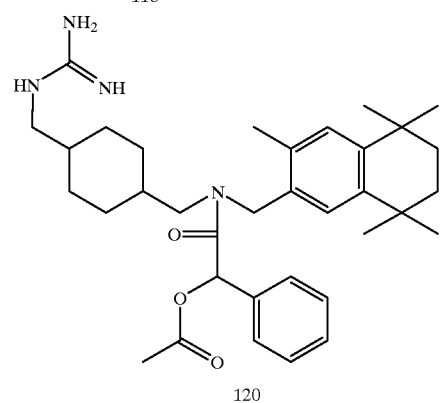
120

Of the specific compounds identified above, Compound Nos. 4, 5, 13, 25, 26, 30, 40, 47, 48, 55, and 80 are especially preferred. Other especially preferred GnRH agents of the Formula I include the following Compound Nos. 121–124:

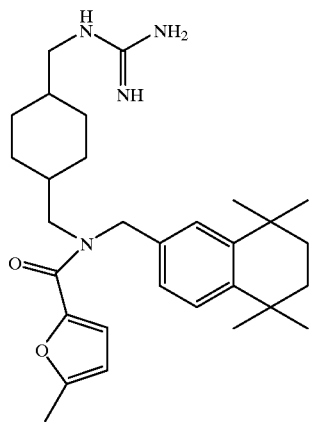

121

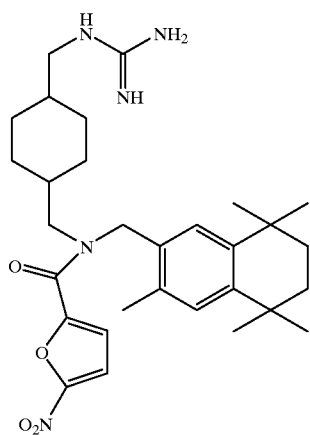

122

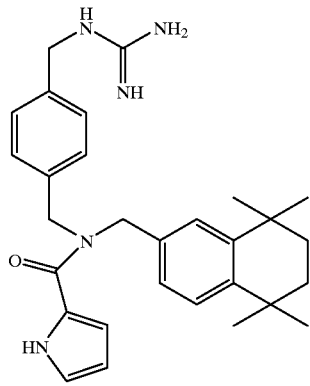

123

-continued

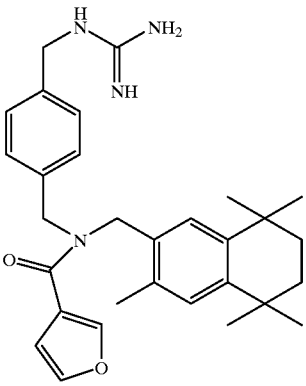

124

As indicated above, GnRH agents in accordance with the invention also include active tautomeric and stereoisomeric forms of the compounds of the Formula I, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

GnRH agents further include multivalent or multimeric forms of active forms of the compounds of the Formula I. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding (see, for example, Lee et al., *Biochem.*, 1984, 23:4255). The artisan may control the multivalency and spacing by selection of a suitable carrier moiety or linker units. Useful moieties include molecular supports containing a multiplicity of functional groups that can be reacted with functional groups associated with the active compounds of the invention. A variety of carrier moieties may be used to build highly active multimers, including proteins such as BSA (bovine serum albumin) or HAS, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

Additionally, GnRH agents of the invention include pharmaceutically acceptable salts of compounds of the Formula I. The term "pharmaceutically acceptable" refers to salt forms that are pharmacologically acceptable and substantially non-toxic to the subject being administered the GnRH agent. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

The term "prodrug" refers to a metabolic precursor of a compound of the Formula I (or a salt thereof) that is pharmaceutically acceptable. A prodrug may be inactive when administered to a subject but is converted in vivo to an active compound of the Formula I. The term "active metabolite" refers to a metabolic product of a compound of the Formula I that is pharmaceutically acceptable and effective. Prodrugs and active metabolites of compounds of the Formula I may be determined using techniques known in the art.

A variety of known assays and techniques may be employed to determine the level of activity of various forms of the compounds in the GnRH system. Ligand-binding assays are used to determine interaction with the receptor of interest. Where binding is of interest, a labeled receptor may be used, where the label is a fluorescer, enzyme, radioisotope, or the like, which registers a quantifiable change upon the binding of the receptor. Alternatively, the artisan may provide for an antibody to the receptor, where the antibody is labeled, which may allow for amplification of the signal. Binding may also be determined by competitive displacement of a ligand bound to the receptor, where the ligand is labeled with a detectable label. Where agonist and/or antagonist activity is of interest, an intact organism or cell may be studied, and the change in an organismic or cellular function in response to the binding of the compound of interest may be measured. Various devices are available for detecting cellular response, such as a microphysiometer available from Molecular-Devices, Redwood City, Calif. In vitro and in vivo assays useful in measuring GnRH antagonist activity are known in the art. See, e.g., Bowers et al., "LH suppression in cultured rat pituitary cells treated with 1 ng of LHRH," *Endocrinology*, 1980, 106:675–683 (in vitro,) and Corbin et al., "Antiovulatory activity (AOA) in rats," *Endocr. Res. Commun.* 1975, 2:1–23 (in vivo). Particular test protocols that may be used are described below.

Figure 2:
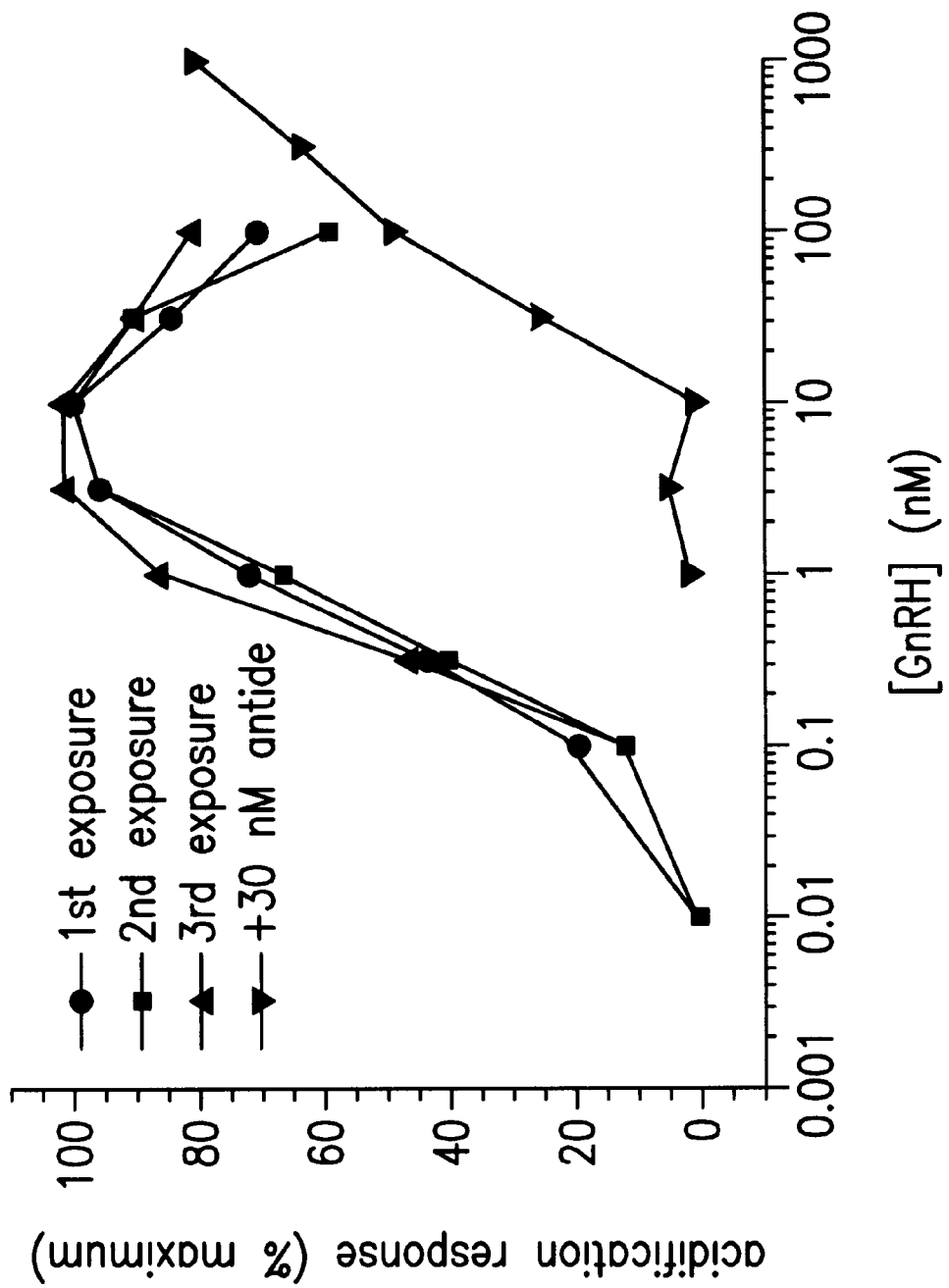
FIG. 2 is a plot of the percent acidification in cells expressing human GnRH receptors in response to increasing concentration of GnRH in the absence and presence of a GnRH antagonist.

For example, GnRH-receptor antagonists may be functionally assessed by measurement of change in extracellular acidification rates as follows. The ability of compounds to block the extracellular rate of acidification mediated by GnRH in HEK 293 cells expressing human GnRH receptors is determined as a measure of the compound's antagonist activity in vitro. Approximately 100,000 cells/chamber are immobilized in agarose suspension medium (Molecular Devices) and perfused with unbuffered MEM media utilizing the Cytosensor® Microphysiometer (Molecular Devices). Cells are allowed to equilibrate until the basal acidification rate remains stable (approximately one hour). Control dose-response curves are performed to GnRH ($10^{-11}$M to $10^{-7}$M). Compounds are allowed to incubate 15 minutes prior to stimulation with GnRH, and are assessed for antagonist activity. After incubation with test compounds, repeat dose-response curves to GnRH in the presence or absence of various concentrations of the test compounds are obtained. Schild regression analysis is performed on compounds to determine whether compounds antagonize GnRH-mediated increases in extracellular acidification rates through a competitive interaction with the GnRH receptor. See, e.g., the acidification response using the antagonist peptide Antide (CAS No. 11258-12-4) shown in FIG. 2 (Antide was purchased from Sigma, Product No. A8802 (acetyl-B-(2-Napthyl)-D-Ala-D-p-Chloro-Phe-B-(3-Pyridyl)-D-Ala-Ser-Ne-(Nicotinoyl)-Lys-Ne-(Nicotinoyl)-D-Lys-Leu-Ne-(Isopropyl)-Lys-Pro-D-Ala-$NH_2$)). Acidification response of the cells to GnRH is shown in the curves in FIG. 2, where curve A is for the first exposure, curve B is for the second exposure, and curve C is for the third exposure. Cell response to GnRH in the presence of 30 nM Antide is shown in curve D of FIG. 2.

In another test, accumulation of total inositol phosphates may be measured by formic acid extraction from cells, followed by separation of the phosphates on Dowex columns. Cells are split using trypsin into two 12-well plates and pre-labeled with $^3$H-myoinositol (0.5 Ci–2 mCi per mL) for 16–18 hours in inositol-free medium. The medium is then aspirated and the cells rinsed with either 1× HBSS, 20 mM HEPES (pH 7.5), or serum-free DMEM, 1× HBSS, 20 mM HEPES (pH 7.5) containing agonist, and 20 mM LiCl is then added and the cells are incubated for the desired time. The medium is aspirated and the reaction stopped by addition of ice-cold 10 mM formic acid, which also serves to extract cellular lipids. Inositol phosphates are separated by ion-exchange chromatography on Dowex columns, which are then washed with 5 mL of 10 mM myoinositol and 10 mM formic acid. The columns are then washed with 10 mL of 60 mM sodium formate and 5 mM borax, and total inositol phosphates are eluted with 4.5 mL 1M ammonium formate, 0.1 M formic acid.

Preferred GnRH agents of the invention include those having a $K_i$ value of about 10 µM or less. Especially preferred GnRH agents are those having a $K_i$ value in the nanomolar range.

Pharmaceutical Compositions

Pharmaceutical compositions according to the invention comprise an effective GnRH-suppressing amount of at least one GnRH agent according to the invention and an inert or pharmaceutically acceptable carrier or diluent. These compositions may be prepared in a unit-dosage form appropriate for the desired mode of administration, e.g., parenteral or oral.

To treat diseases or conditions mediated by GnRH agonism or antagonism, a pharmaceutical composition of the invention is administered in a suitable formulation prepared by combining a therapeutically effective amount (i.e., a GnRH-modulating amount effective to achieve therapeutic efficacy) of at least one GnRH agent of the invention (as an active ingredient) with one or more pharmaceutically suitable carriers or diluents. Such formulations may be prepared according to conventional procedures, e.g., by appropriately mixing, granulating, and compressing or dissolving the ingredients in known manners. Optionally, one or more different active ingredients, such as different GnRH antagonists, may be employed in a pharmaceutical composition.

The pharmaceutical carrier may be either a solid or liquid. Exemplary solid carriers include lactose, sucrose, talc, gelatin, agar, pectin, acacia, magnesium stearate, stearic acid, and the like. Illustrative of liquid carriers are synip, peanut oil, olive oil, water, and the like. Similarly, the carrier or diluent may include time-delay or time-release materials known in the art, such as glyceryl monostearate or glyceryl distearate, alone or in combination with a wax, ethylcellulose, hydroxypropylmethylcellulose, methylmethacrylate, or the like.

A variety of pharmaceutical forms can be employed. For example, if a solid carrier is used, the preparation may be in the form of a tablet, hard-gelatin capsule, powder, pellet, troche, or lozenge. The amount of solid carrier may vary widely, with an exemplary amount ranging from about 25 mg to about 1 g. If a liquid carrier is used, the preparation may be in the form of a syrup, emulsion, soft-gelatin capsule, sterile injectable solution, suspension in an ampoule or vial, or non-aqueous liquid suspension.

To obtain a stable, water-soluble dosage form, a pharmaceutically acceptable salt of a compound of Formula I may be dissolved in an aqueous solution of an organic or inorganic acid, such as 0.3M solution of succinic acid or, more preferably, citric acid. If a soluble salt form is not available, the agent may be dissolved in one or more suitable cosolvents. Examples of suitable cosolvents include alcohol, propylene glycol, polyethylene glycol 300, polysorbate 80, gylcerin, and the like in concentrations ranging from 0% to 60% of the total volume. In an exemplary embodiment, a compound of Formula I is dissolved in DMSO and diluted with water. The composition may also be in the form of a solution of a salt form of a compound of the Formula I in an appropriate aqueous vehicle, such as water, or isotonic saline or dextrose solutions.

The pharmaceutical compositions of the present invention may be manufactured using conventional techniques, e.g., mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients or auxiliaries selected to facilitate processing of the active compounds into pharmaceutical preparations. An appropriate formulation is selected in view of the route of administration chosen.

For preparing injectable preparations, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation and may be selected from those known in the art.

For oral administration, the agents may be formulated readily by combining the active ingredient(s) with pharmaceutically acceptable carriers known in the art. Such carriers enable the compounds of the invention to be formulated as tablets, pills, dragees, capsules, liquids, gels, syrups, slurries, suspensions, and the like, for oral ingestion by a patient to be treated. Pharmaceutical preparations for oral use can be obtained by combining one or more agents with a solid excipient, optionally grinding the resulting mixture into granules, and processing the mixture of granules after adding suitable auxiliaries, if desired, to obtain tablets or dragee cores. Suitable excipients include fillers such as sugars (e.g., lactose, sucrose, mannitol, or sorbitol) and cellulose preparations (e.g., maize starch, wheat starch, rice starch, potato starch, gelatin, gum, methyl cellulose, hydroxypropylmethylcellulose, sodium carboxymethylcellulose, and/or polyvinylpyrrolidone (PVP)). If desired, disintegrating agents may be added, such as cross-linked PVP, agar, or alginic acid or a salt thereof such as sodium alginate.

Dragee cores are provided with suitable coatings. For this purpose, concentrated sugar solutions may be used, which may optionally contain gum arabic, PVP, Carbopol™ gel, polyethylene glycol, titanium dioxide, lacquer solutions, and/or one or more suitable organic solvents. Dyestuffs or pigments may be added to the tablets or dragee coatings for identification or to characterize different combinations of active compound doses.

Pharmaceutical forms that are suitable for oral administration include pushfit capsules made of gelatin, as well as soft, sealed capsules made of gelatin and a plasticizer, such as glycerol or sorbitol. The push-fit capsules may contain the active ingredient(s) in admixture with one or more fillers such as lactose, binders such as starches, and/or lubricants such as talc or magnesium stearate, and, optionally, stabilizers. In soft capsules, the active compound may be dissolved or suspended in a suitable liquid, such as fatty oil, liquid paraffin, or liquid polyethylene glycol. In addition, stabilizers may be added. For buccal administration, the compositions may take the form of tablets or lozenges formulated in a conventional manner.

For administration by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or another suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the agent and a suitable powder base such as lactose or starch.

The agents may be formulated for parenteral administration by injection, e.g., by bolus injection or continuous infusion. Formulations for injection may be prepared in unit-dosage form, e.g., in ampoules, or in multi-dose containers, with an added preservative. The compositions may take such forms as suspensions, solutions, or emulsions in oily or aqueous vehicles, and may contain formulatory agents such as suspending, stabilizing, and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters such as ethyl oleate or triglycerides, or liposomes. Aqueous injectable suspensions may contain substances increasing the viscosity of the suspension, such as sodium carboxymethyl cellulose, sorbitol, or dextran. Optionally, the suspension may also contain suitable stabilizers or agents increasing the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated as rectal compositions, such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system (VPD is a solution of 3% w/v benzyl alcohol, 8% w/v of the nonpolar surfactant polysorbate 80, and 65% w/v polyethylene glycol 300, made up to volume in absolute ethanol). The VPD co-solvent system (VPD:5W) is comprised of VPD diluted 1:1 with a 5% dextrose-in-water solution. This co-solvent system dissolves hydrophobic compounds well, and the resulting formulation produces low toxicity upon systemic administration. As will be apparent, the proportions of a suitable co-solvent system may be varied in light of the solubility and toxicity characteristics. Furthermore, the identity of the co-solvent components may be varied: for example, other low-toxicity nonpolar surfactants may be used instead of polysorbate 80; the fraction size of polyethylene glycol may be varied; one or more other biocompatible polymers (e.g., PVP) may be added or replace polyethylene glycol; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs and may be used to formulate suitable preparations. Certain organic solvents such as dimethylsulfoxide also may be employed, although this may cause an increase in toxicity. Additionally, delivery may be achieved using a sustained-release system, such as semipermeable matrices of solid hydrophobic polymers containing the therapeutic agent. Various sustained-release materials are available and known to those skilled in the art. Sustained-release capsules may, depending on their chemical nature, release the compounds for a period lasting from a few weeks or up to over 100 days. Depending on the chemical nature and the biological stability of the therapeutic agent, additional techniques for protein stabilization may be readily employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter-ions. Pharmaceutically acceptable salts may be formed with many acids, including hydrochloric, sulfuric, acetic, lactic, tartaric, malic, succinic, and like acids. Salts tend to be more soluble in aqueous or other protonic solvents than are the corresponding free-base forms.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given compound. For oral administration, an exemplary daily dose generally employed will be from about 0.001 to about 1000 mg/kg of body weight, with courses of treatment repeated at appropriate intervals. Administration of prodrugs may be dosed at weight levels that are chemically equivalent to the weight levels of the fully active compounds.

Examples of specific pharmaceutical preparations in accordance with the invention are provided below.

Parenteral Composition: To prepare a pharmaceutical composition of this invention suitable for administration by injection, 100 mg of a pharmaceutically acceptable water-soluble salt of a compound of Formula I is dissolved in DMSO and then mixed with 10 mL of 0.9% sterile saline. The resulting mixture is incorporated into a unit-dosage form suitable for administration by injection.

Oral Composition: To prepare an orally administerable pharmaceutical composition, 100 mg of a compound of Formula I is mixed with 750 mg of lactose. The resulting mixture is incorporated into a unit-dosage form suitable for oral administration, such as a hard-gelatin capsule.

Synthesis of GnRH Agents

Intermediates.

Compounds of the Formula I may be advantageously made using intermediate compounds in accordance with the invention. In particular, intermediate compounds of the invention are of the following Formulae II, III, and IV:

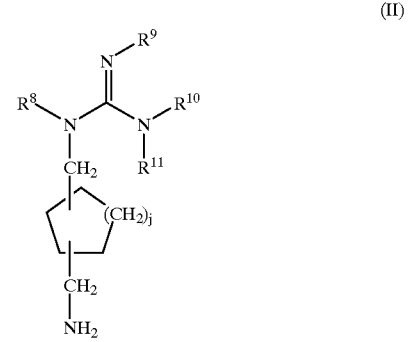

(II)

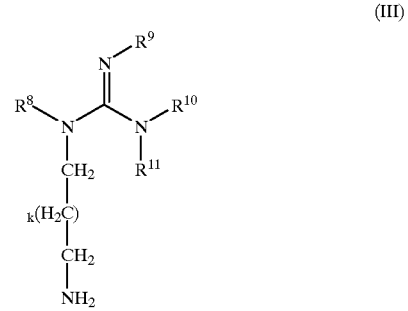

(III)

-continued

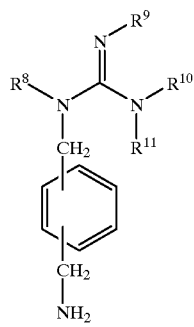
(IV)

wherein:

j is 1 or 2;

k is 1, 2, 3, 4 or 5;

$R^8$ is H or substituted or unsubstituted lower alkyl;

$R^9$ is H or substituted or unsubstituted lower alkyl, CN, $NO_2$ or $CO_2R^1$;

$R^{10}$ is H or substituted or unsubstituted lower alkyl; $CH_2OR^1$; $(CH_2)_pOR^1$; $CO_2R^1$; or $(CH_2)_pC(O)R^2$, where p is an integer from 1 to 6, and $R^2$ is H, $OR^1$, $SR^1$, $N(R^1)_2$, or $C(R^1)_3$;

$R^{11}$ is H or substituted or unsubstituted lower alkyl, $CH_2O$-phenyl, $CH_2O$-benzyl, phenyl or benzyl;

or any two of $R^8$, $R^9$, $R^{10}$, and $R^{11}$ together form a 5- or 6-membered heterocycle;

and each $R^1$ is independently selected from H and substituted or unsubstituted lower alkyl, O-lower alkyl, and S-lower alkyl, with tBu being a preferred $R^1$ group.

Preferred intermediates include:

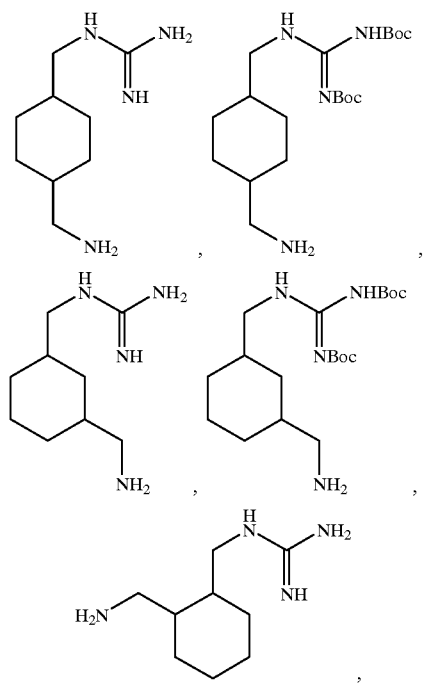

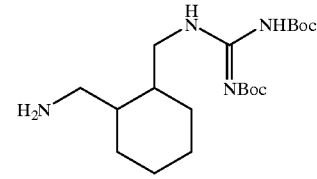

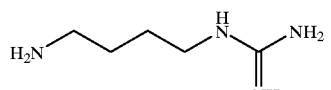

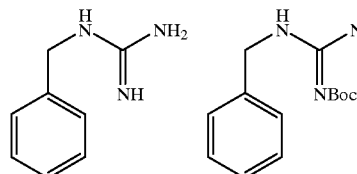

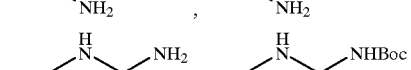

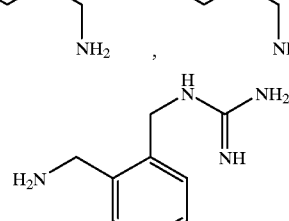

, and

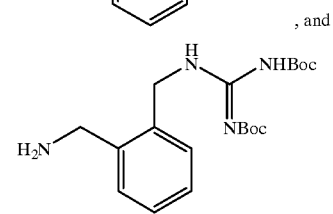

Such intermediate compounds have utility in forming the $X_1$-$X_2$ portion of the compounds of the present invention, by reaction of the amine group with an aldehyde to form a secondary amine, which may then be acylated to form compounds of the general Formula I.

Reaction Scheme.

Compounds of the Formula I may be prepared according to the following general reaction scheme, where the spherical symbol represents the $(CH_2)_j$, cyclopentyl, cyclohexyl, or benzyl moiety of Formula II, III, or IV:

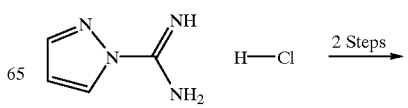

-continued

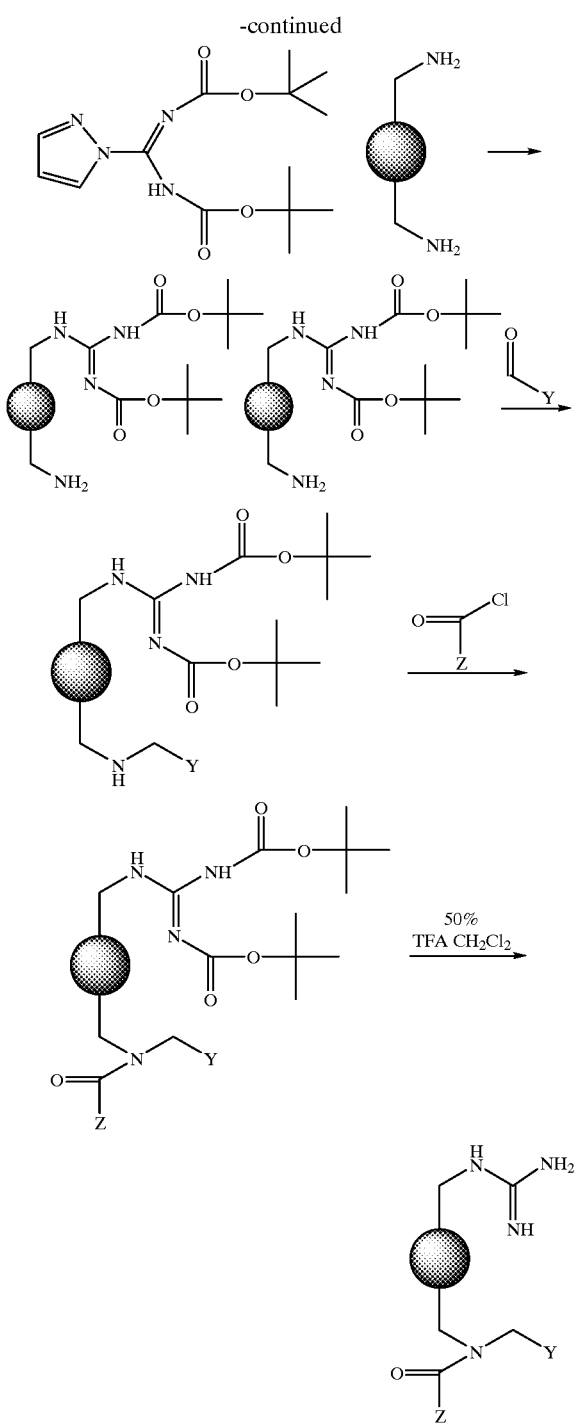

To illustrate, the synthesis depicted in the reaction scheme below employs intermediates of the Formula II for preparing compounds of the Formula I where the $X_1$-$X_2$ unit is 1-guanidinomethyl-4-aminomethylcyclohexyl. As described in more detail below, step 1 involves protection of the basic group, using tert-butoxycarbonyl (Boc) as a protecting group. In the illustrated scheme the basic group is guanidinyl, but, as will be readily apparent to artisans, this reaction is applicable to other basic groups such as amines and amidines as well. Step 2 involves forming a secondary amine by reaction with the aldehyde ZCHO, where Z is as defined above. Step 3 involves acylation of the secondary amine with YCOCl, where Y is as defined above. Step 4 involves deprotection of the basic group by acid hydrolysis. The product may be isolated as the corresponding salt.

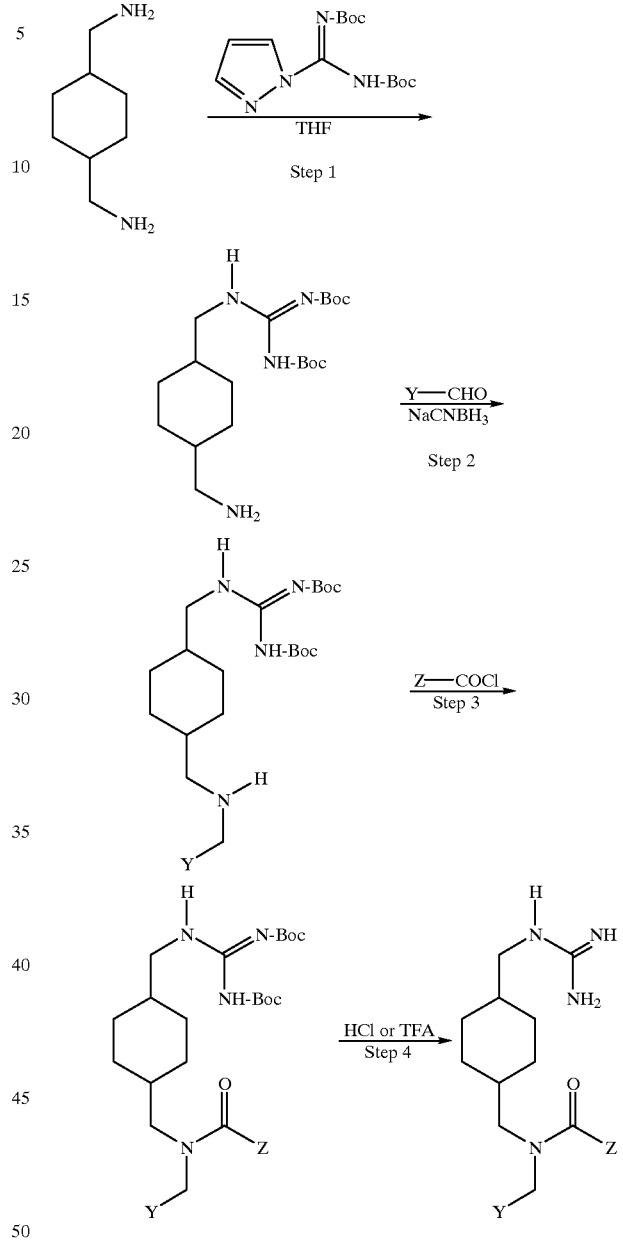

Step 1
Preparation of Protected Compound by 1-(N,N'-diBoc)-guanidinomethylation:
Alternative Steps 1(A) and 1(B) below provide two general 1-(N,N'-diBoc)-guanidinomethylation procedures.
Step 1(A):
To a solution of diamine (2.00 mmol equiv.) in THF (0.7M) is added a solution of 1-H-pyrazole-1-(N,N-bis(tert-butoxycarbonyl)carboxamidine) (1.00 mmol equiv.) in THF (0.7M). The solution is stirred at room temperature for 3 hours (h), or until no further transformation can be observed by TLC (thin-layer chromatography). The solvent is removed under reduced pressure to give a syrupy residue, which is taken up in ethyl acetate (~1.5 times the volume amount of THF used in the reaction or the volume of solvent needed to dissolve the amount of residue obtained) and washed with water until neutral pH. The organic layer is washed with brine, dried over MgSO$_4$, and concentrated. The product is purified by column chromatography on silica gel and eluted with an appropriate elution solvent (which may be readily determined, e.g., using 5% MeOH in dichloromethane as a starting point). The solvents are removed in vacuo to afford the 1-(N,N'-diBoc)-guanidinomethyl-linked-amine. In addition other reagents can be used to place a protected N,N'-diBoc-guanidine unit on diamines, such as 1,3-bis(tert-butoxycarbonyl)-2-methyl-2-thiopseudourea (CAS No. 107819-90-0). Alternatively, the 1-H-pyrazole-1-(N,N-bis(tert-butoxycarbonyl)carboxamidine) can be added directly as a solid, rather than as a solution as described above.

Step 1(B):

To a solution of diamine (1.00 mmol equiv.) in THF (0.07M) is added portionwise as a solid (over a 10-minute time period) 1-H-pyrazole-1-(N,N-bis(tert-butoxy-carbonyl)carboxamidine) (1.00 mmol equiv.). The solution is stirred at room temperature for 0.5 hour. The solvent is removed under reduced pressure to give a syrupy residue, which is taken up in ethyl acetate (0.5 times the volume amount of THF used in the reaction, or the volume of solvent needed to dissolve the amount of residue obtained) and washed twice with water. The layers are separated, and the product is purified by column chromatography on silica gel and eluted with 100% ethyl acetate to remove any non-polar impurities and then with 100% isopropyl alcohol to give the pure product. The solvents are removed in vacuo to afford the desired product. Typical TLC conditions are 15:85:0.1 methanol/chloroform/acetic acid. Typical yields range from 40% to 44% of the desired protected compound.

Step 2

Reductive Amination:

Reductive amination may be accomplished in a suitable manner. For reductive amination of aldehydes and ketones with sodium triacetoxyborohydride, see generally: Abdel-Magid et al., *J. Org. Chem.*, 1996, 61:3849. Two alternate reductive-aminations procedures are described below.

Step 2(A):

3,5,5,8,8-Pentamethyl-5,6,7,8-tetrahydro-2-naphthaldehyde (1.00 mmol equiv.) and 1-(N,N'-diBoc)-guanidinomethyl-linked-amine (1.00 mmol equiv.) are dissolved in methanol (0.09M). Then, 1% glacial acetic acid in methanol solution (10% of the volume of methanol used) is added followed by NaCNBH$_3$ (1.00 mmol equiv.), and the reaction contents are stirred overnight. The reaction is assayed by TLC to reveal three components (aldehyde, desired product, and starting guanidine derivative). The reaction is terminated by adding water (50% of the volume of methanol used), extracted with dichloromethane (10 times the volume of methanol used), and washed with saturated sodium bicarbonate. The organic layer is dried over magnesium sulfate, filtered, and concentrated. The product is purified by column chromatography on silica gel and eluted with an appropriate elution solvent (e.g., 3:1 ethyl acetate in hexanes to remove the unreacted aldehyde, followed by elution with 1:1 ethyl acetate in hexanes), obtaining the desired reductive amination product. In some cases, warming to reflux for 2 hours will facilitate the imine formation reaction. See also, Abdel-Magid et al., *J. Org. Chem.*, 1996, 61:3849, which describes the reductive amination of aldehydes and ketones with sodium triacetoxyborohydride.

Step 2(B):

3,5,5,8,8-Pentamethyl-5,6,7,8-tetrahydro-2-naphthaldehyde (1.00 mmol equiv.) and 1-(N,N'-diBoc)-guanidinomethyl-linked-amine (1.00 mmol equiv.) are dissolved in methanol (0.09M). Then, NaBH$_4$ (1.00 mmol equiv.) is added (in ethanol via the additional small-scale procedures given below, or carefully as a solid) and the reaction contents are stirred overnight. The reaction is assayed by TLC to reveal three components (aldehyde, desired product and starting guanidine derivative). The reaction is terminated by the addition of water (50% of the volume of methanol used), extracted with dichloromethane (10 times the volume of methanol used), and washed with saturated sodium bicarbonate. The organic layer is dried over magnesium sulfate, filtered, and concentrated. The product is purified by column chromatography on silica gel and eluted with an appropriate elution solvent (as can be readily determined by the skilled artisan or, for example, with 3:1 ethyl acetate in hexanes to remove the unreacted aldehyde followed by elution with 1:1 ethyl acetate in hexanes) to obtain the desired reductive-amination product. In some cases, warming to reflux for 2 hours should facilitate the imine-formation reaction.

Step 3

Acylation:

The products from the reductive amination (1.00 mmol equiv.) are dissolved in dichloromethane (~0.2 to 0.05M, depending on solubilities of the substrates), followed by the addition of triethylamine (2.00 mmol equiv.) and 2-furoyl chloride (1.00 mmol equiv.). The reaction contents are stirred overnight at room temperature (RT). The reaction mixture is diluted with dichloromethane (5 times the amount of dichloromethane used) and washed with saturated sodium bicarbonate. The organic layer is dried over magnesium sulfate and filtered. The product is purified by column chromatography on silica gel and eluted with an appropriate elution solvent (e.g., 3:1 hexanes:ethyl acetate). The solvents are removed in vacuo to yield the acylated product.

Step 4

Basic Group Deprotection:

The product from the acylation step (1.00 mmol equiv.) is dissolved in a solution of 25–50% TFA in dichloromethane (0.02M), and the reaction contents are stirred at room temperature (15–20 minutes; solution becomes slight reddish-orange). The reaction contents are stirred for an additional 1 hour and 20 minutes or until the BOC deprotection is complete. The reaction is terminated by concentration in vacuo, followed by the addition of water/acetonitrile (0.006M) and lyophilization overnight. The final compound is purified by high-performance liquid chromatography (HPLC) methodology. The solvents are removed in vacuo (yields range from 30% to 50%) to give the product.

An alternate procedure for removing of N,N'-bis-BOC guanidines using tin tetrachloride, which can give the corresponding guanidinium chloride salts, is described in Miel et al., *Tetrahedron Letters*, 1997, 38:7865–7866.

Preparation of Reagents:

Reagents useful for synthesizing compounds may be obtained or prepared according to techniques known in the art. For example, the preparation of free amines from common salt forms and stock reagent solutions can be useful for small-scale reactions. See also Abdel-Magid et al., "Reductive amination of aldehydes and ketones with sodium triacetoxyborohydride," *J. Org. Chem.*, 1996, 61:3849.

Methanolic solutions of the free bases can be prepared from hydrochloride, dihydrochloride, hydrobromide, or other salts when the free base is soluble in methanol. In this procedure, once the sodium methoxide is added, care should be taken to prevent exposure to air, since amine free bases, particularly primary amines, absorb carbon dioxide from the air to form salts. A 10-mL quantity of a 0.1M solution of a free base in methanol may be prepared as follows. Weigh 1.0 mmol of a monohydrochloride salt into a tared Erlenmeyer flask containing a stirring bar, and add 7 mL of methanol. To the stirred slurry, add 229 mL (1.0 mmol, 1 equiv.) of sodium methoxide in methanol (25 wt %, 4.37M), stopper the flask, and stir the mixture vigorously for 2 hours. The slurry will sometimes change in appearance as a finer, milky precipitate of sodium chloride is formed. Filter the slurry through a 15-mL medium fritted glass funnel, wash the filter case with 1–2 mL methanol, transfer the filtrate to a 20-mL vial, and dilute to 10 mL with methanol. The theoretical yield of sodium chloride is nearly 59 mg, but the recovery is usually not quantitative, owing to a slight solubility in methanol. For a dihydrochloride salt, a second equivalent of sodium methoxide is required (458 mL).

A 0.5M solution of sodium borohydride in ethanol may be prepared as follows. Sodium borohydride (520 mg, 13.8 mmol) is stirred in pure (non-denatured) anhydrous ethanol (25 mL) for 2–3 minutes. The suspension is filtered through a medium fritted glass funnel to remove a small amount of undissolved solid (typically about 5% of the total mass of borohydride, or 25 mg). The filtrate should appears as a colorless solution that evolves only a little hydrogen. This solution should be used immediately, as it decomposes significantly over a period of a few hours, resulting in the formation of a gelatinous precipitate. Sodium borohydride is hygroscopic, so avoid exposure to air by making the solution at once after weighing the solid. Sodium borohydride has a solubility of about 4% in ethanol at room temperature. This corresponds to a little over 0.8M. However, sometimes a small percentage of the solid remains undissolved regardless of the concentration being prepared, even after stirring for ≧5 minutes.

To perform small-scale synthesis of compounds of the Formula I, the reactions described below may be performed to prepare various reactants useful in the reaction scheme described above. As with the rest of the specification, all temperatures in the following description are in degrees Celsius and all parts and percentages are by weight, unless indicated otherwise.

Starting materials and other reagents used in the following examples may be purchased from commercial suppliers, such as Aldrich Chemical Company or Lancaster Synthesis Ltd., and used without further purification, unless otherwise indicated. Tetrahydrofuran (THF) and N,N-dimethylformamide (DMF) are purchased from Aldrich in SureSeal® bottles and used as received. All solvents are purified by using standard methods in the art, unless otherwise indicated.

The reactions set forth below are performed under a positive pressure of nitrogen or with a drying tube, at ambient temperature (unless otherwise stated), in anhydrous solvents, and the reaction flasks are fitted with rubber septa for the introduction of substrates and reagents via syringe. Glassware is oven-dried and/or heat-dried. Analytical thin-layer chromatography (TLC) is performed on glass-backed silica gel 60° F. 254 plates (Analtech (0.25 mm)) and eluted with the appropriate solvent ratios (v/v). The reactions are assayed by TLC and terminated as judged by the consumption of starting material.

The tip plates are visualized with a p-anisaldehyde spray reagent or phosphomolybdic acid reagent (Aldrich Chemical, 20 wt % in ethanol) and activated with heat. Work-ups are typically done by doubling the reaction volume with the reaction solvent or extraction solvent and then washing with the indicated aqueous solutions using 25% by volume of the extraction volume (unless otherwise indicated). Product solutions are dried over anhydrous $NASO_4$ prior to filtration, and evaporation of the solvents is under reduced pressure on a rotary evaporator and noted as solvents removed in vacuo. Flash column chromatography (Still et al., A.J Org. Chem., 1978, 43:2923) is conducted using Baker-grade flash silica gel (47–61 mm) and a silica gel:crude material ratio of about 20:1 to 50:1, unless otherwise stated. Hydrogenolysis is done at the pressure indicated or at ambient pressure.

$^1$H-NMR spectra are recorded on a Bruker instrument operating at 300 MHz, and $^{13}$C-NMR spectra are recorded operating at 75 MHz. NMR spectra are obtained as $CDCl_3$ solutions (reported in ppm), using chloroform as the reference standard (7.25 ppm and 77.00 ppm) or $CD_3OD$ (3.4 and 4.8 ppm and 49.3 ppm), or an internal tetramethylsilane standard (0.00 ppm) when appropriate. Other NMR solvents are used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra are recorded on a Perkin-Elmer FT-IR Spectrometer as neat oils, as KBr pellets, or as $CDCl_3$ solutions, and when reported are in wave numbers ($cm^{-1}$). The mass spectra are obtained using LSIMS or electrospray. All melting points are uncorrected.

Preparation of the Building Block 1-H-pyrazole-1-carboxamidine:

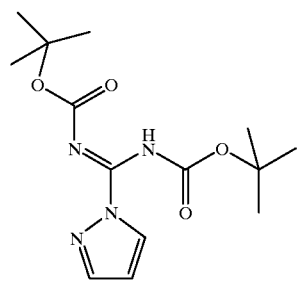

1-H-pyrazole-1-carboxamidine is prepared according to Bernatowicz et at, J. Org Chem., 1992, 57:2497–2502 (and references therein), and protected with di-tert-butyldicarbonate to give 1-H-pyrazole-1-(N,N-bis(tert-butoxycarbonyl)carboxamidine) according to Drake et al., Synth., 1994, 579–582.

Preparation of 1-(N,N'-diBoc)-guanidinomethyl-4-aminomethylcyclohexane:

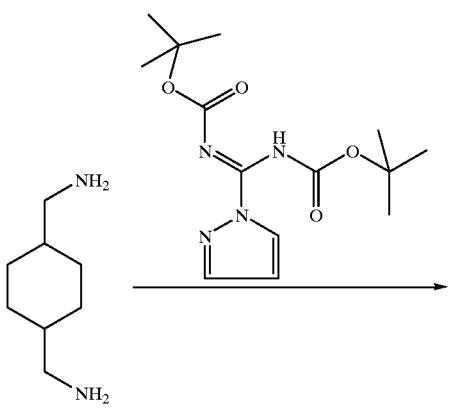

To a solution of 1,4-bis-aminomethyl-cyclohexane (20 g, 0.14 mol) in THF (200 mL) is added a solution of 1-H-pyrazole-1-(N,N-bis(tert-butoxycarbonyl)carboxamidine) (22.0 g, 0.07 mol) in THF (100 mL). (Note that 1-H-pyrazole-1-(N,N-bis(tert-butoxycarbonyl)carboxamidine) does not need to be dissolved in THF; rather it may be added neat as a solid to the process.) The solution is stirred at room temperature for 3 hours. The solvent is removed under reduced pressure to give a syrupy residue, which is taken up in ethyl acetate (500 mL) and washed with water until neutral pH. The organic layer is washed with brine, dried over MgSO$_4$, and concentrated. The product is purified by column chromatography on silica gel and eluted with 5% MeOH in dichloromethane. The solvents are removed in vacuo to afford 11.6 g (43% yield) of 1-(N,N'-diBoc)-guanidinomethyl-4-aminomethyl cyclohexane (Compound (a)). $^1$H NMR (CDCl$_3$) δ 11.5 (br s, 1H), 8.35 (br s, 1H), 3.26 (dt, 2H), 2.52 (dd, 2H), 1.82–0.97 (m, 28H, with singlet at 1.5).

An alternate preparation of 1-(N,N'-diBoc)-guanidinomethyl-3-aminomethylcyclohexane is as follows. To a solution of cis/trans 1,4-bis-aminomethyl-cyclohexane (9.0 g, 63.3 mmol) in THF (903 mL, 0.07M) is added portionwise as a solid (over a 10-minute period) 1-H-Pyrazole-1-(N,N-bis(tert-butoxycarbonyl)carboxamidine) (19.6 g, 63.3 mmol). The solution is stirred at room temperature for 0.5 hour. The solvent is removed under reduced pressure to give a syrupy residue, which is taken up in ethyl acetate (500 mL) and washed twice with water. The layers are separated and the product is purified by column chromatography on silica gel and eluted with 100% ethyl acetate to remove any non-polar impurities, followed by elution with 100% isopropyl alcohol, to give the pure product. The solvents are removed in vacuo to afford 10.2 g (42% yield) of 1-(N,N'-diBoc)-guanidinomethyl-4-aminomethylcyclohexane. $^1$H NMR (CDCl$_3$) δ 11.5 (br s, 1H), 8.35 (br s, 1H), 3.26 (dt, 2H), 2.52 (dd, 2H), 1.82–0.97 (m, 28H, with singlet at 1.5).

Reductive Amination

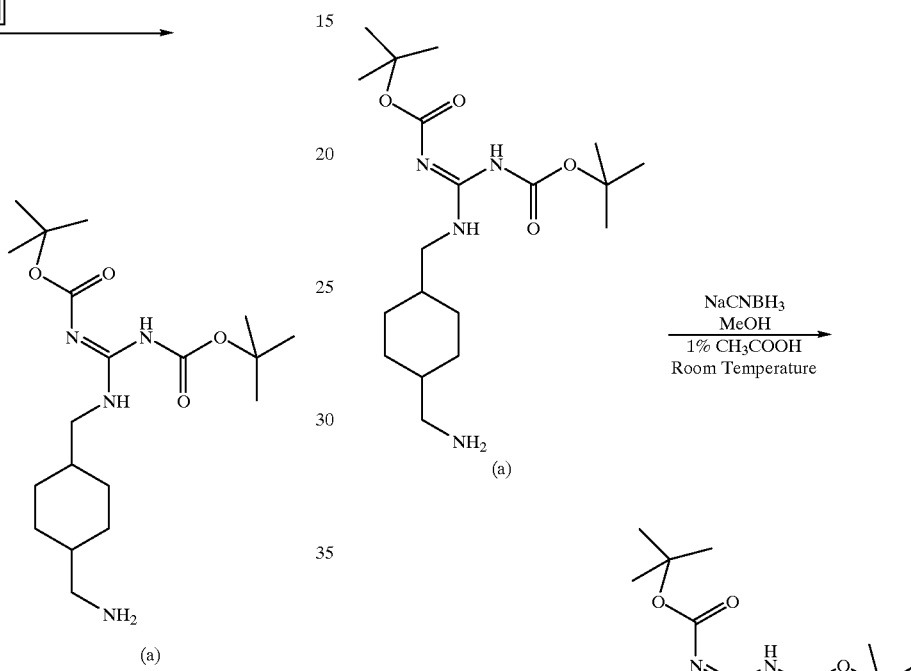

3,5,5,8,8-Pentamethyl-5,6,7,8-tetrahydro-2-naphth-aldehyde (0.2021 g, 0.88 mmol) and 1-(N,N'-diBoc)-guanidinomethyl-4-aminomethylcyclohexane (Compound (a), 0.337 g, 0.88 mmol) are dissolved in methanol (10 mL). Then, 1% glacial acetic acid in methanol (100 μL) solution is added followed by NaCNBH$_3$ (55.4 mg, 0.88 mmol, 1.0 equiv.), and the reaction contents are stirred overnight. The reaction is assayed by TLC to reveal three components (aldehyde, desired product, and starting guanidine derivative). The reaction is terminated by the addition of water (~5 mL), extracted with dichloromethane (~100 mL), and washed with saturated sodium bicarbonate. The organic layer is dried over magnesium sulfate, filtered, concentrated, and subjected to column chromatography eluting with 3:1 ethyl acetate in hexanes to remove the unreacted aldehyde, followed by eluting with 1:1 ethyl acetate in hexanes, yielding the desired product (Compound (b), cyclohexyl, cis/trans mixture). The solvents are removed in vacuo (typical general yields range from 50 to 80%).

Preparation of the Acylated Derivative Followed by Deprotection of Guanidine:

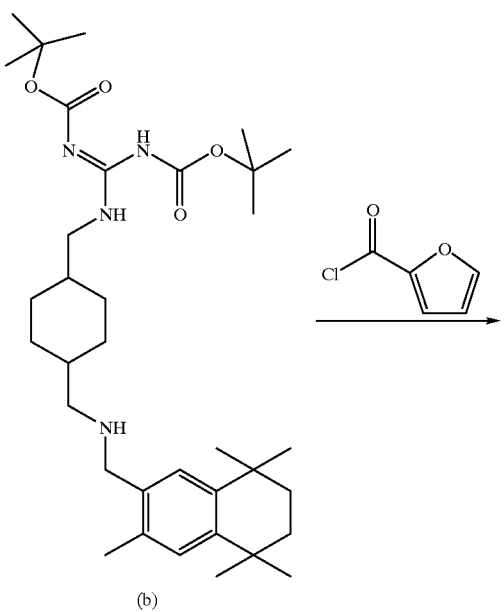

(b)

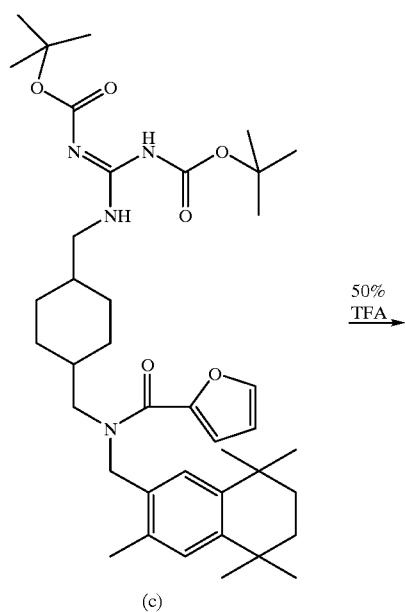

(c)

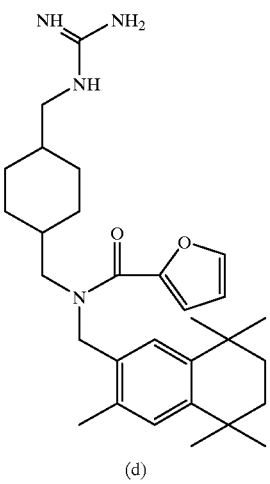

(d)

The product from the reductive amination (320 mg, 0.54 mmol, 1.0 equiv.) is dissolved in dichloromethane (10–15 mL), followed by the addition of triethylamine (129 mg, 1.08 mmol, 2 equiv.), and 2-furoyl chloride (0.53 mmol, 52 μL, 1.0 equiv.). The reaction contents are stirred overnight at room temperature. The reaction is diluted with dichloromethane (50 mL) and washed with saturated sodium bicarbonate. The organic layer is dried over magnesium sulfate, filtered, and purified by column chromatography and eluted using 3:1 hexanes in ethyl acetate. The solvents are removed in vacuo (typical general reaction yields range from 50 to 80%) to give Compound (c).

The product from the acylation reaction (Compound (c), 220 mg, 0.318 mmol, 1.0 equiv.) is dissolved in a solution of 50% TFA in dichloromethane (20–25 mL), and the reaction contents are stirred at room temperature (15–20 minutes; solution becomes slight reddish-orange). The reaction contents are stirred for an additional 1 hour and 20 minutes until the deprotection is complete. The reaction is terminated by concentration in vacuo, followed by the addition of water/acetonitrile (~50 mL) and lyophilization overnight. The final compound is purified by HPLC methods. The solvents are removed in vacuo (yields range from 30 to 50%) to give Compound (d).

The above discussion relates to the preparation of Compounds (a)–(d). The following discussion relates to the preparation of exemplary Compounds (e)–(k). Compounds (e)–(k) may be used as described above to produce the corresponding deprotected (free guanidinyl) compounds, through hydrolysis under acid conditions.

Preparation of 1-(N,N'-diBoc)-guanidinomethyl-3-aminomethylcyclohexane:

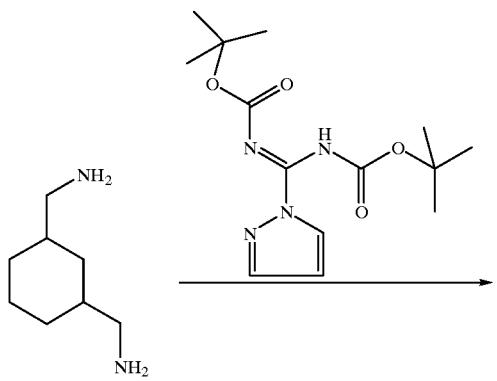

(e)

To a solution of cis/trans-1,3-bis-aminomethylcyclohexane (7.5 g, 52.8 mmol) in THF (30 mL) is added a solution of 1,3-bis(tert-butoxycarbonyl)-2-methyl-2-thiopseudourea (7.65 g, 26.3 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 2.2 g (22% yield) of 1-(N,N'-diBoc)-guanidinomethyl-3-aminomethylcyclohexane (Compound (e)). $^1$H NMR (CDCl$_3$) δ 11.53 (br s, 1H), 8.40 (br s, 1H), 3.28–3.30 (m, 2H), 2.54–2.61 (m, 2H), 1.81 (br s, 2H), 1.27–1.58 (m, 26H), 0.89 (m, 1H), 0.65 (m, 1H).

Alternatively, Compound (e) may be prepared as follows. To a solution of cis/trans 1,3-bis-aminomethylcyclohexane (10.0 g, 70.3 mmol) in THF (1000 mL, 0.07M) is added portionwise as a solid (over a 10-minute period) 1-H-Pyrazole-1-(N,N-bis(tert-butoxycarbonyl)carboxamidine) (21.8 g, 70.3 mmol). The solution is stirred at room temperature for 0.5 hour. The solvent is removed under reduced pressure to give a syrupy residue, which is taken up in ethyl acetate (500 mL) and washed twice with water. The layers are separated, and the product is purified by column chromatography on silica gel and eluted with 100% ethyl acetate to remove any non-polar impurities, followed by elution with 100% isopropyl alcohol to give the pure product. The solvents are removed in vacuo to afford 11.4 g (41% yield) of 1-(N,N'-diBoc)-guanidinomethyl-3-aminomethylcyclohexane. $^1$H NMR (CDCl$_3$) δ 11.53 (br s, 1H), 8.40 (br s, 1H), 3.28–3.30 (m, 2H), 2.54–2.61 (m, 2H), 1.81 (br s, 2H), 1.27–1.58 (m, 26H), 0.89 (m, 1H), 0.65 (m, 1H).

Preparation of 1-(N,N'-diBoc)-guanidinomethyl-4-aminomethylbenzene:

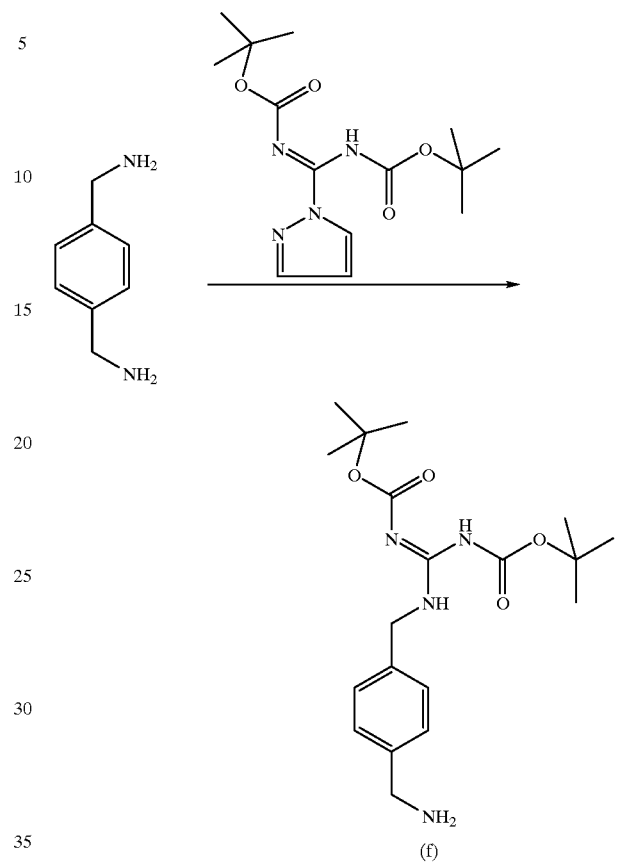

(f)

To a solution of p-xylylenediamine (6.44 g, 47.4 mmol) in THF (30 mL) is added a solution of 1,3-bis(tert-butoxycarbonyl)-2-methyl-2-thiopseudourea (6.63 g, 22.9 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 8.0 g (92% yield) of 1-(N,N'-diBoc)-guanidinomethyl-4-aminomethyl benzene (Compound (f)). $^1$H NMR (CDCl$_3$) δ 11.54 (br s, 1H), 8.56 (br s, 1H), 7.29 (s, 4H), 4.60 (d, 2H), 3.86 (s, 2H), 1.64 (br s, 2H), 1.52 (s, 9H), 1.48 (s, 9H).

Preparation of 1-(N,N'-diBoc)-guanidinomethyl-3-aminomethylbenzene:

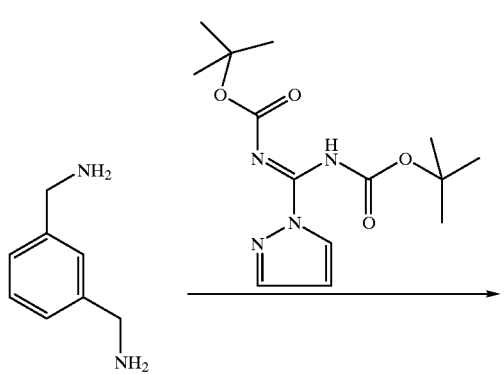

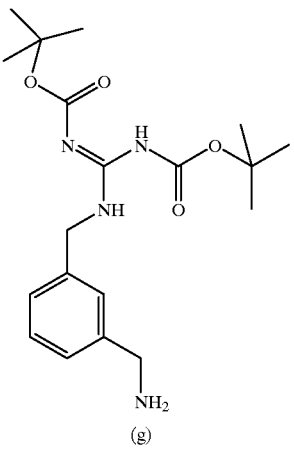

(g)

To a solution of m-xylylenediamine (7.14 g, 52.5 mmol) in THF (30 mL) is added a solution of 1,3-bis(tert-butoxycarbonyl)-2-methyl-2-thiopseudourea (7.57 g, 26.1 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 7.9 g (80% yield) of 1-(N,N'-diBoc)-guanidinomethyl-3-aminomethylbenzene (Compound (g)). 1H NMR (CDCl$_3$) δ 11.54 (br s, 1H), 8.58 (br s, 1H), 7.19–7.34 (m, 4H), 4.62 (d, 2H), 3.86 (s, 2H), 1.83 (br s, 2H), 1.52 (s, 9H), 1.48 (s, 9H).

Preparation of 1-(N,N'-diBoc)-guanidine-4-aminobutane:

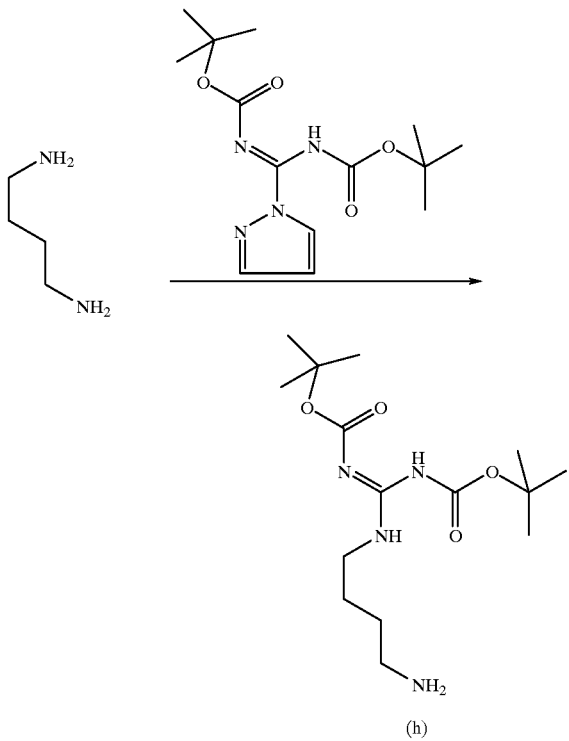

(h)

To a solution of 1,4-diaminobutane (4.15 g, 47.1 mmol) in THF (30 mL) is added a solution of 1,3-bis(tert-butoxycarbonyl)-2-methyl-2-thiopseudourea (6.83 g, 23.6 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 3.0 g (40% yield) of 1(N,N'-diBoc)-guanidino-4-aminobutane (Compound (h)). $^1$H NMR (CDCl$_3$) δ 11.49 (br s, 1H), 8.35 (br s, 1H), 3.42–3.47 (m, 2H), 2.72–2.76 (t, 2H), 0.86–1.65 (m, 24H).

An alternate procedure for preparing Compound (h) is as follows. To a solution of 1,4-diaminobutane (6.0 g, 68.1 mmol) in THF (972 mL, 0.07M) is added portionwise as a solid (over a 10-minute period) 1-H-pyrazole-1-(N,N-bis(tert-butoxycarbonyl)carboxamidine) (21.5 g, 68.1 mmol). The solution is stirred at room temperature for 0.5 hour. The solvent is removed under reduced pressure to give a syrupy residue, which is taken up in ethyl acetate (500 mL) and washed twice with water. The layers are separated and the product is purified by column chromatography on silica gel and eluted with 100% ethyl acetate to remove any non-polar impurities and then with 100% isopropyl alcohol to give the pure product. The solvents are removed in vacuo to afford 10.0 g (44% yield) of 1-(N,N'-diBoc)-guanidino-4-aminobutane. $^1$H NMR (CDCl$_3$) δ 11.49 (br s, 1H), 8.35 (br s, 1H), 3.42–3.47 (m, 2H), 2.72–2.76 (t, 2H), 0.86–1.65 (m, 24H).

Preparation of 1-N,N-dimethylaminomethyl-4-aminomethylbenzene:

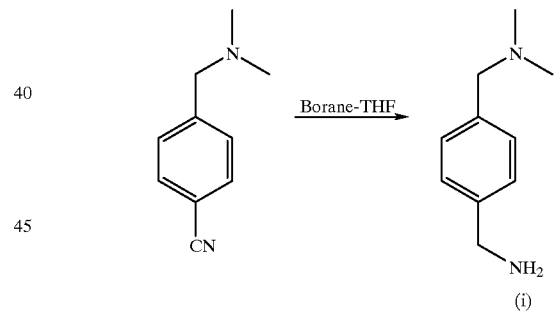

(i)

To a solution of 1-N,N-dimethyl aminomethyl-4-carbonitrile benzene (4.8 g, 30 mmol) in THF is added a solution of 1 M borane tetrahydrofuran complex (90 mL). The mixture is heated at reflux temperature for 16 hours under nitrogen. After cooling to room temperature, a 1M solution of HCl in methanol (100 mL) is added. The reaction mixture is heated at reflux for 3 hours. The product, which precipitates, is collected by filtration, washed with diethyl ether, and dried in vacuo to give 5.9 g (83% yield) of the product as the hydrochloride salt (Compound (i)): $^1$H NMR (DMSO-d$_6$) δ 8.65 (br s, 3H), 7.55 (dd, 4H), 4.25 (s, 2H), 3.98 (s, 2H), 2.62 (s, 6H).

Preparation of 1-(N,N'-diBoc)-guanidinomethyl-2-aminomethylbenzene:

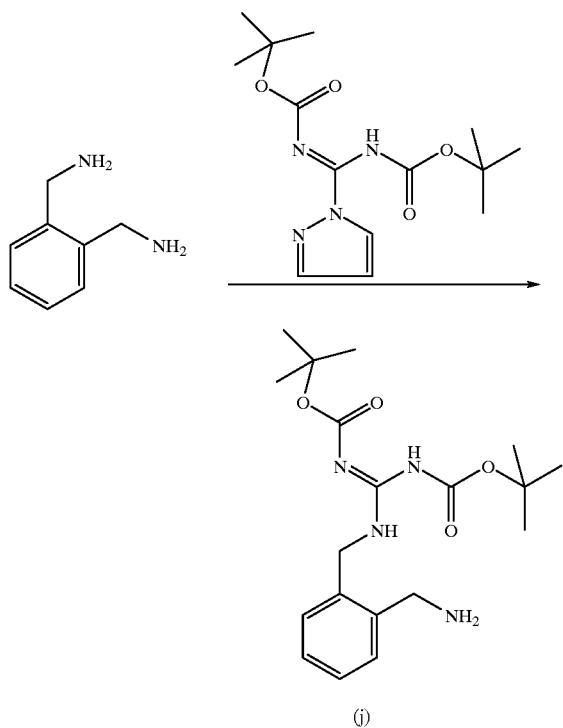

(j)

To a solution of o-xylylenediamine (7.14 g, 52.5 mmol) in THF (30 mL) is added a solution of 1,3-bis(tert-butoxycarbonyl)-2-methyl-2-thiopseudourea (7.57 g, 26.1 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 1-(N,N'-diBoc)-guanidinomethyl-3-aminomethyl benzene (Compound (j)).

Alternatively, Compound (j) may be prepared in a manner analogous to the alternative preparation described above for Compound (e).

Preparation of -(N,N'-diBoc)-guanidinomethyl-2-aminomethylcyclohexane:

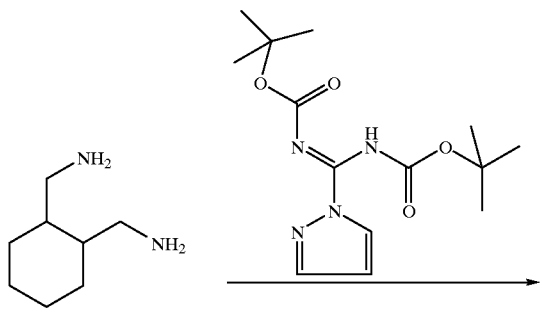

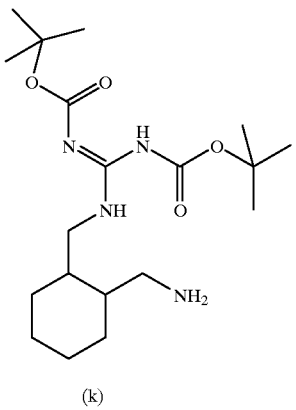

(k)

To a solution of cis/trans-1,2-bis-aminomethylcyclohexane (7.5 g, 52.8 mmol) in THF (30 mL) is added a solution of 1,3-bis(tert-butoxycarbonyl)-2-methyl-2-thiopseudourea (7.65 g, 26.3 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 1-(N,N'-di Boc)-guanidinomethyl-2-aminomethylcyclohexane (Compound (k)).

Alternatively, Compound (k) may be prepared in a manner analogous to the alternative preparation described above for Compound (e).

Preparation of Benzylamines:

The following general reaction procedure provides a method for the preparation of benzylamines for use with aldehydes containing protected guanidines as an alternative to diamines. The reductive aminations proceed under the same reaction conditions as for the protected guanidine amines described earlier.

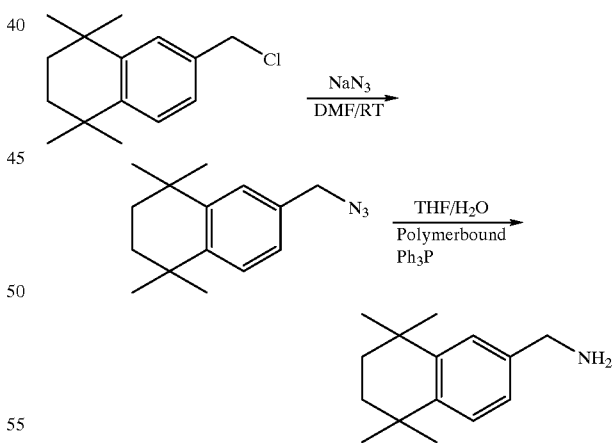

To a solution of 6-chloromethyl-1,2,3,4-tetrahydro-1,1,4,4-tetramethylnaphthalene (10 g, 42.2 mmol, 1.00 mmol equiv.) in DMF (84 mL) is added sodium azide (13.7 g, 211.2 mmol, 5.00 mmol equiv.) at room temperature and the reaction contents are stirred overnight. The reaction is checked by TLC (5% ethyl acetate in hexanes). The reaction is terminated by pouring the reaction contents into water and extracting with ethyl acetate. The organic solvents are removed in vacuo and the crude product filtered through a plug of silica gel (ratio of 10:1) and eluted with hexanes. The solvent is removed in vacuo and stored under vacuo to afford 10 grams of the desired product 6-azidomethyl-1,2,3,4-tetrahydro-1,1,4,4-tetramethylnaphthalene (97% yield).

To a solution of 6-azidomethyl-1,2,3,4-tetrahydro-1,1,4,4-tetramethylnaphthalene (9.0 g, 37 mmol, 1.00 mmol equiv.) in water/THF (1:5 ratio, 0.16M, 231 mL) is added polymer-bound triphenylphosphine (14.8 g, 44.38 mmol, 1.20 mmol equiv., ~3 mmol/g resin) at room temperature, and the reaction contents are stirred for 18–24 hours. The reaction is checked by TLC (5% ethyl acetate in hexanes). The reaction is terminated by filtering through a filter paper and washing the resin with methanol, and the product is checked by $^1$H NMR. The organic solvents are removed in vacuo, and the product filtered through a plug of silica gel (ratio of 10:1) and eluted with 25% isopropyl alcohol in chloroform to remove a higher-running minor impurity. The organic solvents are removed in vacuo, yielding a thick oil that solidifies upon standing (7.5 g, 93% yield).

The chemical reactions described above have general applicability to the preparation of the GnRH agents of the invention. Thus, other GnRH agents may be similarly prepared by suitable modification as will be readily appreciated by those skilled in the art, e.g., by protection of interfering groups, by adapting for use with other conventional reagents, and/or by routine modifications of reaction conditions.

Biological Testing

Compounds are assayed for activity according to the following protocol.

Stable Transfection of Human GnRH Receptors.

The cDNA for the human GnRH receptor is cloned into the plasmid expression vector, pcDNA 3 (In Vitrogen), and stably transfected in HEK 293 cells (a cell line developed by Dr. Stuart Sealfon, Mount Sinai Medical School, New York, N.Y.).

The human GnRH receptor (hGnRH) is cloned into pcDNA 3 (In Vitrogen), which provides high-level expression and a neomycin resistance marker. Lipofectamine (GIBCO BRL) is used to transfect HEK 293 cells with plasmid DNA. This method involves mixing the plasmid and reagent in serum-free medium, allowing DNA-liposome complexes to form, and overlaying cells with this solution. The HEK 293 cells are plated (seeded) on a 10-cm tissue culture dish at a density of $3 \times 10^6$ cells/dish the day before transfection. For each plate, 8 µg DNA plus 0.8 mL serum-free medium is mixed with 48 µL lipofectamine plus 0.8 mL serum-free medium, followed by incubation for 30 minutes at room temperature to allow DNA-liposome complexes to form. Serum-free medium is added to give a final volume of 6 mL/plate. The cells are rinsed twice with serum-free medium and overlayed with the DNA-liposome mixture. Five hours after transfection, an equal volume (6 mL) of medium containing 20% FBS (fetal bovine serum) is added. The cells are fed with fresh complete medium 18–24 hours after transfection. The cells are split 72 hours following transfection, at densities of 1:10 and 1:20. Stable tranformants are selected for by growth of the cells in antibiotic containing medium (G418, Sigma Chemical Company (also known as Geneticin)). Colonies are isolated and tested for receptor expression by radioligand binding and by measuring phosphoinositol turnover.

Cell Culture and Cell Membrane Preparation.

HEK 293 cells stably transfected with human GnRH receptors as described above are grown in MEM (minimal essential medium, available from Sigma Chemical Company) supplemented with 0.1% G418 (Sigma Chemical Company). Cells are homogenized in buffer A containing 50 mM Tris (pH 74.), 0.32M sucrose, 2 mM ethyleneglycolbis(β-aminoethyl)-N,N,N',N'-tetraacetic acid (EGTA), 1 mM phenylmethylsulfonyl fluoride (PMSF), 5 µg/mL aprotinen, 5 µg/mL Pepstatin A, and 1 µg/mL leupeptin. The homogenized cells are centrifuged at 4° C. at 20,000×g for 25 minutes, resuspended in buffer A, and recentrifuged at 4° C. at 20,000×g for an additional 25 minutes. Total membrane protein is determined with a BCA kit (Pierce, Rockford, Ill.). Membranes are stored at –70° C. at a final membrane protein concentration of 5 mg/mL.

$^{125}$I-GnRH-A Preparation.

The radioiodinated agonist analog of GnRH, [des-Gly$^{10}$, D-Ala$^8$]GnRH ethylamide (GnRH-A), is used as the labeled ligand. One µg of GnRH-A diluted in 0.1M acetic acid is added to an Iodogen®-coated borosilicate glass tube (Pierce) containing 35 µL of 0.05M phosphate buffer (pH 7.4–7.6) and 1 mCi of Na[$^{125}$I]. The reaction mixture is vortexed and incubated for 1 minute at room temperature. After one minute, the mixture is vortexed again and allowed to incubate for an additional minute. Two mL of 0.5M acetic acid/1% BSA is added to the reaction tube, and the mixture is added to a C18 Sep-Pak cartridge. The cartridge is washed with subsequent washes of 5 mL $H_2O$ and 5 mL 0.5M acetic acid, and then eluted with 5×1 mL of 60% $CH_3CN$/40% 0.5M acetic acid. The eluant is diluted with 3×volume of HPLC buffer A (0.1% TFA in $H_2O$) and loaded onto a C18 column. The iodinated product is eluted over 20–25 minutes with a gradient of 25–100% $CH_3CN$ containing 0.1% TFA. The radioactive fractions (750 µL/fraction) are collected into clean polypropylene tubes containing 10µL of 10% BSA. Fractions are assessed for biological activity by radioligand binding. Active fractions are utilized to screen the compounds for competitive binding assays.

Competition Radioligand Binding Assays.

HEK 293 cell membranes stably expressing hGnRH (human GnRH receptors) are diluted to 0.5–1.0 mg/mL with assay buffer containing 50 mM HEPES (pH 7.4), 1 mM ethylenediaminetetraacetic acid (EDTA), 2.5 mM $MgCl_2$, and 0.1% BSA. The membranes are incubated with 50,000 CPM (approximately 0.05–0.1 mM) of $^{125}$I-GnRH-A in a final volume of 200 µL in the presence or absence of competing agents for 1 hour at room temperature. Assays are stopped by rapid filtration onto 96-well GF/C filters soaked in 0.1% polyethylenimine. Filters are washed three times with ice-cold PBS (50 mM $NaPO_4$, 0.9% NaCl, 2 mM $MgCl_2$, and 0.02% $NaN_3$, pH 7.4) using a Packard 96-well cell harvester. Subsequently, 35 µL of scintillation cocktail is added to each filter well, and filters are counted on a Packard Top count. Nonspecific binding is determined in the presence of 100 nM GnRH. Control dose-response curves are generated to GnRH (0.1 nM–100 nM) in each experiment. A dose-response curve is shown in FIG. 1, which depicts the amount of radiolabeled GnRH bound by the cell membranes (CPM) versus concentration of unlabeled GnRH.

EXAMPLES

As skilled artisans will appreciate, a variety of compounds according to the invention may be prepared. For example, compounds of the Formula I having the combination of $X_1$-$X_2$Y, and Z moieties shown in Table A below may be prepared, where the $X_1$-$X_2$, Y, and Z moieties are identified in Tables 1, 2, and 3.

TABLE A

Exemplary Compounds

| $X_1X_2$ | Y | Z |
|---|---|---|
| $X_1X_2$-7 | Y-1 | Z-1 |
| $X_1X_2$-7 | Y-10 | Z-1 |
| $X_1X_2$-7 | Y-1 | Z-2 |
| $X_1X_2$-7 | Y-6 | Z-2 |
| $X_1X_2$-7 | Y-8 | Z-2 |
| $X_1X_2$-7 | Y-1 | Z-3 |
| $X_1X_2$-7 | Y-8 | Z-3 |
| $X_1X_2$-7 | Y-10 | Z-3 |
| $X_1X_2$-7 | Y-1 | Z-4 |
| $X_1X_2$-7 | Y-9 | Z-4 |
| $X_1X_2$-7 | Y-1 | Z-5 |
| $X_1X_2$-7 | Y-1 | Z-6 |
| $X_1X_2$-7 | Y-7 | Z-6 |
| $X_1X_2$-7 | Y-9 | Z-6 |
| $X_1X_2$-7 | Y-10 | Z-6 |
| $X_1X_2$-7 | Y-1 | Z-7 |
| $X_1X_2$-7 | Y-4 | Z-7 |
| $X_1X_2$-7 | Y-5 | Z-7 |
| $X_1X_2$-7 | Y-11 | Z-7 |
| $X_1X_2$-7 | Y-1 | Z-8 |
| $X_1X_2$-7 | Y-3 | Z-8 |
| $X_1X_2$-5 | Y-10 | Z-3 |
| $X_1X_2$-5 | Y-1 | Z-4 |
| $X_1X_2$-5 | Y-9 | Z-4 |
| $X_1X_2$-5 | Y-10 | Z-4 |
| $X_1X_2$-5 | Y-11 | Z-4 |
| $X_1X_2$-5 | Y-1 | Z-5 |
| $X_1X_2$-5 | Y-9 | Z-5 |
| $X_1X_2$-5 | Y-11 | Z-5 |
| $X_1X_2$-5 | Y-1 | Z-6 |
| $X_1X_2$-5 | Y-10 | Z-6 |
| $X_1X_2$-5 | Y-1 | Z-7 |
| $X_1X_2$-5 | Y-1 | Z-8 |
| $X_1X_2$-5 | Y-10 | Z-8 |
| $X_1X_2$-9 | Y-1 | Z-1 |
| $X_1X_2$-9 | Y-10 | Z-1 |
| $X_1X_2$-9 | Y-1 | Z-2 |
| $X_1X_2$-9 | Y-1 | Z-3 |
| $X_1X_2$-9 | Y-10 | Z-3 |
| $X_1X_2$-9 | Y-1 | Z-4 |
| $X_1X_2$-9 | Y-5 | Z-4 |
| $X_1X_2$-9 | Y-1 | Z-5 |
| $X_1X_2$-9 | Y-9 | Z-5 |
| $X_1X_2$-9 | Y-1 | Z-6 |
| $X_1X_2$-9 | Y-10 | Z-6 |
| $X_1X_2$-9 | Y-8 | Z-8 |
| $X_1X_2$-3 | Y-1 | Z-1 |
| $X_1X_2$-3 | Y-3 | Z-1 |
| $X_1X_2$-3 | Y-4 | Z-1 |
| $X_1X_2$-3 | Y-10 | Z-1 |
| $X_1X_2$-3 | Y-3 | Z-2 |
| $X_1X_2$-3 | Y-4 | Z-2 |
| $X_1X_2$-3 | Y-8 | Z-2 |
| $X_1X_2$-3 | Y-1 | Z-3 |
| $X_1X_2$-3 | Y-8 | Z-3 |
| $X_1X_2$-3 | Y-10 | Z-3 |
| $X_1X_2$-3 | Y-1 | Z-4 |
| $X_1X_2$-3 | Y-8 | Z-4 |
| $X_1X_2$-3 | Y-9 | Z-4 |
| $X_1X_2$-3 | Y-10 | Z-4 |
| $X_1X_2$-3 | Y-11 | Z-4 |
| $X_1X_2$-3 | Y-1 | Z-5 |
| $X_1X_2$-3 | Y-8 | Z-5 |
| $X_1X_2$-3 | Y-9 | Z-5 |
| $X_1X_2$-3 | Y-11 | Z-5 |
| $X_1X_2$-3 | Y-1 | Z-6 |
| $X_1X_2$-3 | Y-10 | Z-6 |
| $X_1X_2$-3 | Y-1 | Z-7 |
| $X_1X_2$-3 | Y-9 | Z-7 |
| $X_1X_2$-3 | Y-10 | Z-7 |
| $X_1X_2$-3 | Y-11 | Z-7 |
| $X_1X_2$-3 | Y-1 | Z-8 |
| $X_1X_2$-3 | Y-6 | Z-8 |
| $X_1X_2$-3 | Y-10 | Z-8 |
| $X_1X_2$-11 | Y-1 | Z-1 |
| $X_1X_2$-11 | Y-1 | Z-2 |
| $X_1X_2$-11 | Y-1 | Z-3 |
| $X_1X_2$-11 | Y-1 | Z-4 |
| $X_1X_2$-11 | Y-1 | Z-5 |
| $X_1X_2$-11 | Y-1 | Z-6 |
| $X_1X_2$-11 | Y-1 | Z-7 |
| $X_1X_2$-11 | Y-1 | Z-8 |
| $X_1X_2$-1 | Y-3 | Z-9 |
| $X_1X_2$-1 | Y-15 | Z-9 |
| $X_1X_2$-1 | Y-9 | Z-9 |
| $X_1X_2$-1 | Y-16 | Z-9 |
| $X_1X_2$-1 | Y-10 | Z-9 |
| $X_1X_2$-1 | Y-9 | Z-5 |
| $X_1X_2$-1 | Y-15 | Z-10 |
| $X_1X_2$-1 | Y-10 | Z-10 |
| $X_1X_2$-1 | Y-13 | Z-11 |
| $X_1X_2$-1 | Y-9 | Z-11 |
| $X_1X_2$-1 | Y-10 | Z-11 |
| $X_1X_2$-1 | Y-3 | Z-12 |
| $X_1X_2$-1 | Y-7 | Z-12 |
| $X_1X_2$-1 | Y-9 | Z-12 |
| $X_1X_2$-1 | Y-16 | Z-12 |
| $X_1X_2$-1 | Y-10 | Z-12 |
| $X_1X_2$-1 | Y-13 | Z-7 |
| $X_1X_2$-1 | Y-10 | Z-7 |
| $X_1X_2$-1 | Y-10 | Z-8 |
| $X_1X_2$-1 | Y-10 | Z-13 |
| $X_1X_2$-1 | Y-7 | Z-14 |
| $X_1X_2$-1 | Y-7 | Z-15 |
| $X_1X_2$-1 | Y-7 | Z-17 |
| $X_1X_2$-1 | Y-7 | Z-20 |
| $X_1X_2$-1 | Y-7 | Z-22 |
| $X_1X_2$-1 | Y-7 | Z-23 |
| $X_1X_2$-1 | Y-7 | Z-24 |
| $X_1X_2$-1 | Y-7 | Z-25 |
| $X_1X_2$-1 | Y-7 | Z-26 |
| $X_1X_2$-1 | Y-7 | Z-27 |
| $X_1X_2$-1 | Y-7 | Z-28 |
| $X_1X_2$-1 | Y-7 | Z-30 |
| $X_1X_2$-1 | Y-7 | Z-31 |
| $X_1X_2$-1 | Y-7 | Z-32 |
| $X_1X_2$-1 | Y-7 | Z-33 |
| $X_1X_2$-1 | Y-7 | Z-34 |
| $X_1X_2$-1 | Y-7 | Z-36 |
| $X_1X_2$-1 | Y-7 | Z-37 |
| $X_1X_2$-1 | Y-7 | Z-39 |
| $X_1X_2$-1 | Y-7 | Z-40 |
| $X_1X_2$-1 | Y-7 | Z-41 |
| $X_1X_2$-1 | Y-7 | Z-42 |
| $X_1X_2$-1 | Y-7 | Z-43 |
| $X_1X_2$-1 | Y-7 | Z-44 |
| $X_1X_2$-1 | Y-7 | Z-47 |
| $X_1X_2$-1 | Y-7 | Z-52 |
| $X_1X_2$-1 | Y-7 | Z-53 |
| $X_1X_2$-1 | Y-7 | Z-54 |
| $X_1X_2$-1 | Y-7 | Z-55 |
| $X_1X_2$-1 | Y-7 | Z-56 |
| $X_1X_2$-1 | Y-7 | Z-58 |
| $X_1X_2$-1 | Y-7 | Z-60 |
| $X_1X_2$-1 | Y-7 | Z-61 |
| $X_1X_2$-1 | Y-7 | Z-62 |
| $X_1X_2$-1 | Y-7 | Z-63 |
| $X_1X_2$-1 | Y-7 | Z-64 |
| $X_1X_2$-1 | Y-7 | Z-65 |
| $X_1X_2$-1 | Y-7 | Z-66 |
| $X_1X_2$-1 | Y-7 | Z-67 |
| $X_1X_2$-1 | Y-7 | Z-68 |
| $X_1X_2$-1 | Y-7 | Z-70 |
| $X_1X_2$-1 | Y-7 | Z-71 |
| $X_1X_2$-1 | Y-7 | Z-73 |
| $X_1X_2$-1 | Y-7 | Z-74 |
| $X_1X_2$-1 | Y-7 | Z-75 |
| $X_1X_2$-1 | Y-7 | Z-76 |
| $X_1X_2$-1 | Y-7 | Z-77 |
| $X_1X_2$-1 | Y-7 | Z-78 |

TABLE A-continued

Exemplary Compounds

| $X_1X_2$ | Y | Z |
|---|---|---|
| $X_1X_2$-1 | Y-7 | Z-80 |
| $X_1X_2$-1 | Y-7 | Z-81 |
| $X_1X_2$-1 | Y-7 | Z-83 |
| $X_1X_2$-1 | Y-7 | Z-84 |
| $X_1X_2$-1 | Y-7 | Z-85 |
| $X_1X_2$-1 | Y-7 | Z-86 |
| $X_1X_2$-1 | Y-7 | Z-87 |
| $X_1X_2$-1 | Y-7 | Z-88 |
| $X_1X_2$-1 | Y-7 | Z-89 |
| $X_1X_2$-1 | Y-7 | Z-91 |
| $X_1X_2$-1 | Y-7 | Z-92 |
| $X_1X_2$-1 | Y-7 | Z-93 |
| $X_1X_2$-1 | Y-7 | Z-94 |
| $X_1X_2$-1 | Y-7 | Z-95 |
| $X_1X_2$-1 | Y-7 | Z-98 |
| $X_1X_2$-1 | Y-7 | Z-99 |
| $X_1X_2$-1 | Y-17 | Z-5 |
| $X_1X_2$-1 | Y-20 | Z-5 |
| $X_1X_2$-1 | Y-23 | Z-5 |
| $X_1X_2$-1 | Y-24 | Z-5 |
| $X_1X_2$-1 | Y-25 | Z-5 |
| $X_1X_2$-1 | Y-26 | Z-5 |
| $X_1X_2$-1 | Y-27 | Z-5 |
| $X_1X_2$-1 | Y-29 | Z-5 |
| $X_1X_2$-1 | Y-30 | Z-5 |
| $X_1X_2$-1 | Y-31 | Z-5 |
| $X_1X_2$-1 | Y-32 | Z-5 |
| $X_1X_2$-1 | Y-33 | Z-5 |
| $X_1X_2$-1 | Y-34 | Z-5 |
| $X_1X_2$-1 | Y-35 | Z-5 |
| $X_1X_2$-1 | Y-38 | Z-5 |
| $X_1X_2$-1 | Y-39 | Z-5 |
| $X_1X_2$-1 | Y-41 | Z-5 |
| $X_1X_2$-1 | Y-42 | Z-5 |
| $X_1X_2$-1 | Y-44 | Z-5 |
| $X_1X_2$-1 | Y-46 | Z-5 |
| $X_1X_2$-1 | Y-47 | Z-5 |
| $X_1X_2$-1 | Y-48 | Z-5 |
| $X_1X_2$-1 | Y-49 | Z-5 |
| $X_1X_2$-1 | Y-50 | Z-5 |
| $X_1X_2$-1 | Y-51 | Z-5 |
| $X_1X_2$-1 | Y-54 | Z-5 |
| $X_1X_2$-1 | Y-56 | Z-5 |
| $X_1X_2$-1 | Y-58 | Z-5 |
| $X_1X_2$-1 | Y-59 | Z-5 |
| $X_1X_2$-1 | Y-61 | Z-5 |
| $X_1X_2$-1 | Y-63 | Z-5 |
| $X_1X_2$-1 | Y-65 | Z-5 |
| $X_1X_2$-1 | Y-66 | Z-5 |
| $X_1X_2$-1 | Y-67 | Z-5 |
| $X_1X_2$-1 | Y-69 | Z-5 |
| $X_1X_2$-1 | Y-70 | Z-5 |
| $X_1X_2$-1 | Y-71 | Z-5 |
| $X_1X_2$-1 | Y-72 | Z-5 |
| $X_1X_2$-1 | Y-78 | Z-5 |
| $X_1X_2$-1 | Y-85 | Z-5 |
| $X_1X_2$-1 | Y-86 | Z-5 |
| $X_1X_2$-1 | Y-87 | Z-5 |
| $X_1X_2$-1 | Y-88 | Z-5 |
| $X_1X_2$-1 | Y-90 | Z-5 |
| $X_1X_2$-1 | Y-91 | Z-5 |
| $X_1X_2$-1 | Y-92 | Z-5 |
| $X_1X_2$-1 | Y-94 | Z-5 |
| $X_1X_2$-1 | Y-95 | Z-5 |
| $X_1X_2$-1 | Y-96 | Z-5 |
| $X_1X_2$-1 | Y-97 | Z-5 |
| $X_1X_2$-1 | Y-99 | Z-5 |
| $X_1X_2$-1 | Y-100 | Z-5 |
| $X_1X_2$-1 | Y-101 | Z-5 |
| $X_1X_2$-1 | Y-102 | Z-5 |
| $X_1X_2$-1 | Y-103 | Z-5 |
| $X_1X_2$-1 | Y-104 | Z-5 |

Other exemplary compounds of the Formula I identified in Tables 4 and 5 below were synthesized according to the reaction scheme generally described above. Crude compounds were tested using the competitive radioligand binding assay described above. Results of the GnRH competitive binding assay are shown in Tables 4 and 5. The $X_1$-$X_2$, Y, and Z moieties for the compounds listed in Table 4 are shown in Tables 1, 2, and 3, respectively. Results for the compounds identified in Table 4 were obtained at a single concentration of 10 $\mu$M. Specific binding of diluent (vehicle) controls was determined as the total amount of radioligand bound minus the amount bound in the presence of 100 nM GnRH. The percent of specific binding remaining ("%" in Table 4) in the presence of each compound was calculated according to the following equation: {Specific binding in presence of compound/Specific binding in presence of diluent (vehicle)}×100%. In Table 4, a compound yielding 50% remaining would yield a $K_i$ of approximately 10 $\mu$M. Note that the lower the value for % bound, the higher is the percentage inhibition.

TABLE 1

$X_1X_2$ Moieties

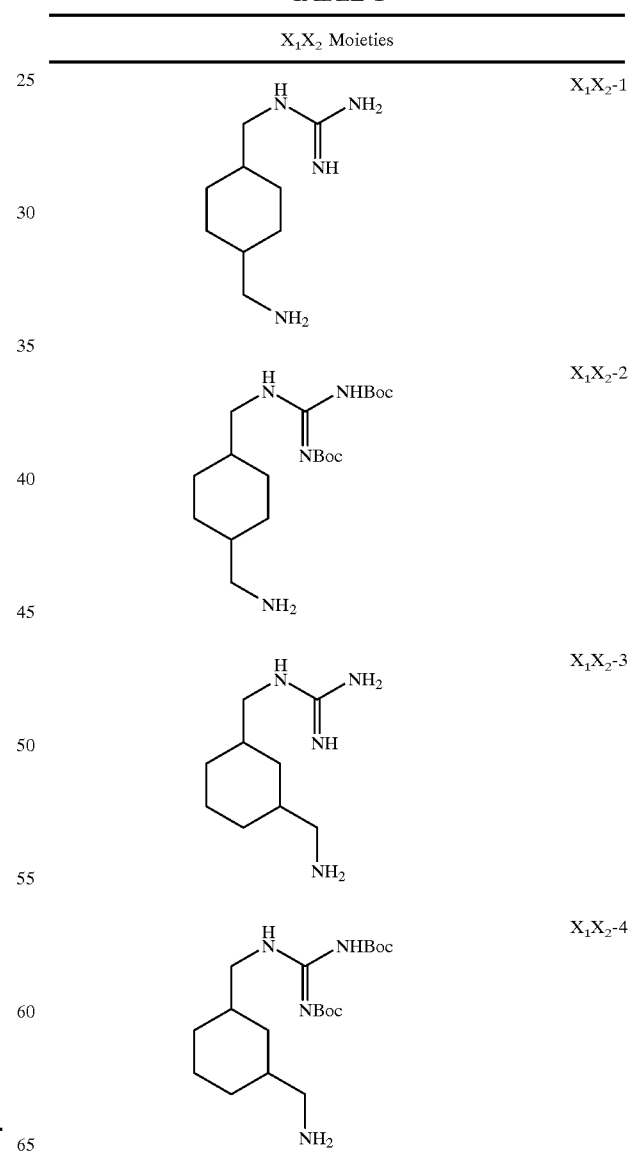

TABLE 1-continued
X₁X₂ Moieties
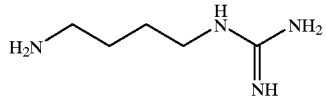 X₁X₂-5
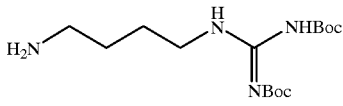 X₁X₂-6
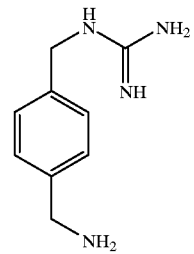 X₁X₂-7
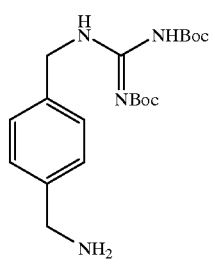 X₁X₂-8
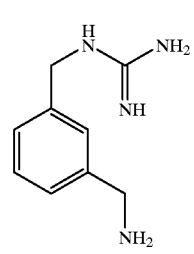 X₁X₂-9
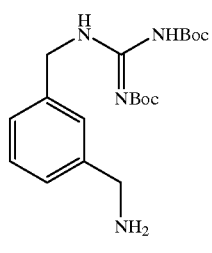 X₁X₂-10
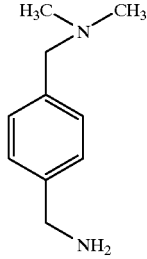 X₁X₂-11
TABLE 2
Y Moieties
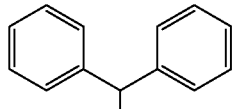 Y-1
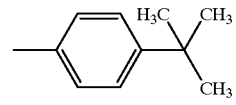 Y-2
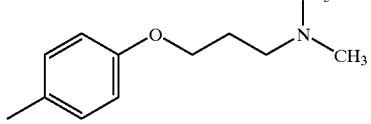 Y-3
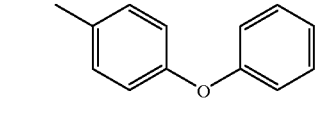 Y-4
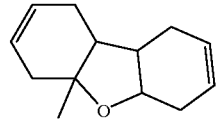 Y-5
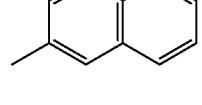 Y-6
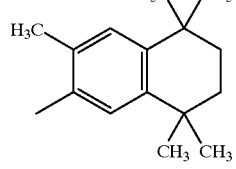 Y-7
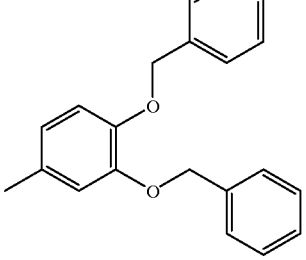 Y-8
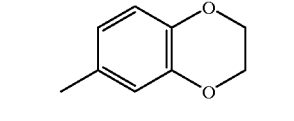 Y-9

US 6,218,426 B1
TABLE 2-continued
Y Moieties
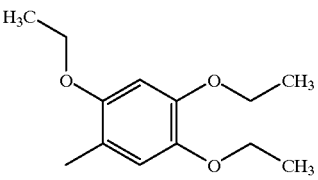 Y-10
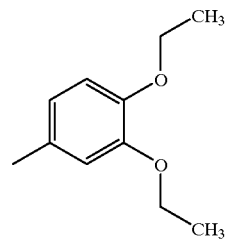 Y-11
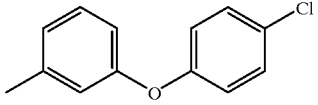 Y-12
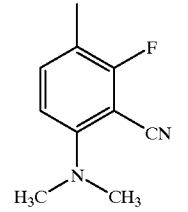 Y-13
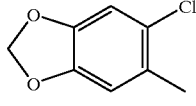 Y-14
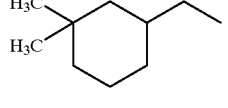 Y-15
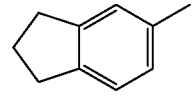 Y-16
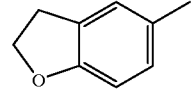 Y-17
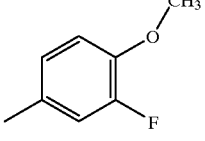 Y-18
TABLE 2-continued
Y Moieties
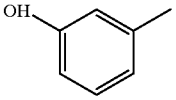 Y-19
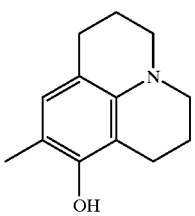 Y-20
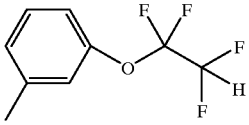 Y-21
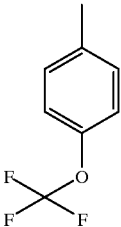 Y-22
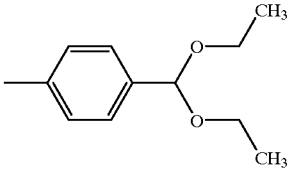 Y-23
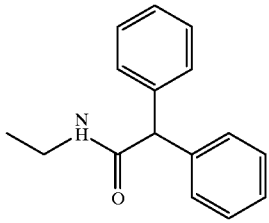 Y-24
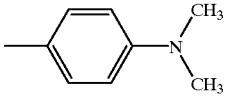 Y-25
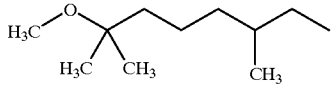 Y-26
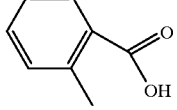 Y-27

TABLE 2-continued
Y Moieties
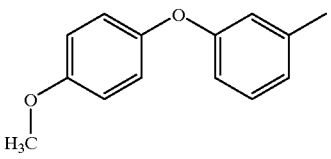 Y-28
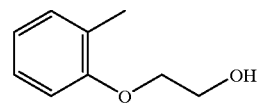 Y-29
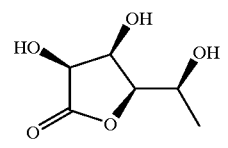 Y-30
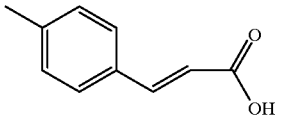 Y-31
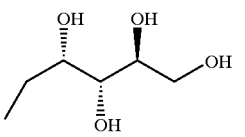 Y-32
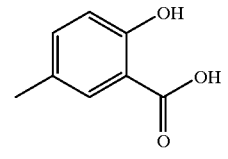 Y-33
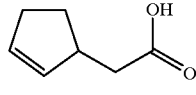 Y-34
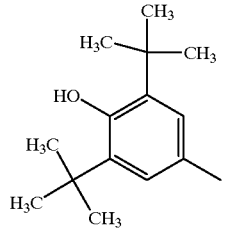 Y-35
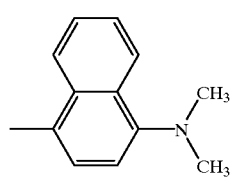 Y-36
TABLE 2-continued
Y Moieties
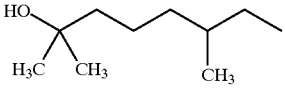 Y-37
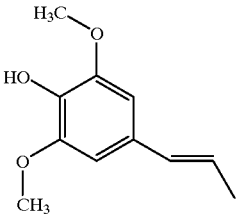 Y-38
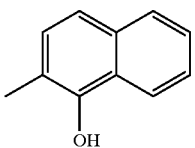 Y-39
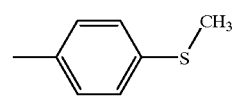 Y-40
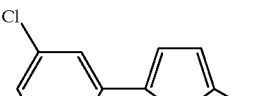 Y-41
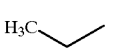 Y-42
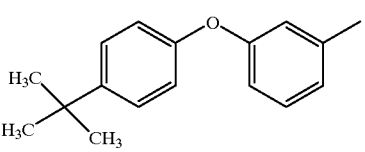 Y-43
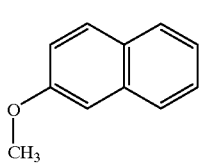 Y-44
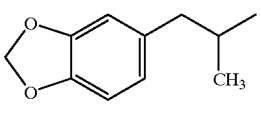 Y-45
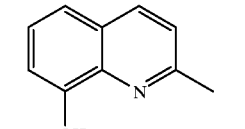 Y-46
 Y-47

TABLE 2-continued

Y Moieties

| | |
|---|---|
| (structure) | Y-48 |
| (structure) | Y-49 |
| (structure) | Y-50 |
| (structure) | Y-51 |
| (structure) | Y-52 |
| (structure) | Y-53 |
| (structure) | Y-54 |
| (structure) | Y-55 |
| (structure) | Y-56 |
| (structure) | Y-57 |
| (structure) | Y-58 |
| (structure) | Y-59 |
| (structure) | Y-60 |
| (structure) | Y-61 |
| (structure) | Y-62 |
| (structure) | Y-63 |
| (structure) | Y-64 |
| (structure) | Y-65 |
| (structure) | Y-66 |

TABLE 2-continued
Y Moieties
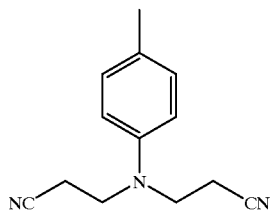 Y-67
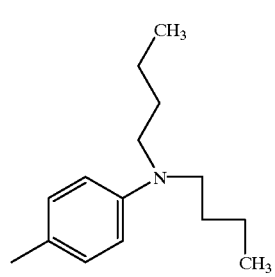 Y-68
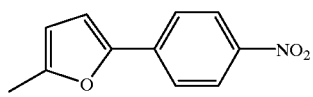 Y-69
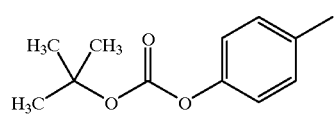 Y-70
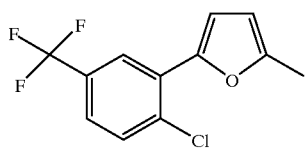 Y-71
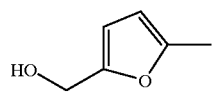 Y-72
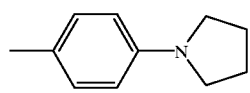 Y-73
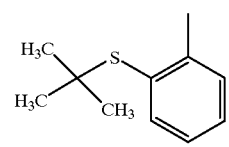 Y-74
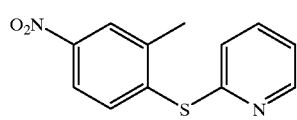 Y-75
TABLE 2-continued
Y Moieties
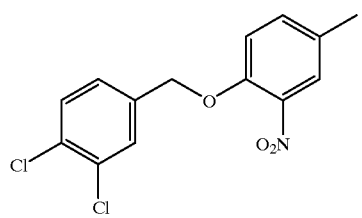 Y-76
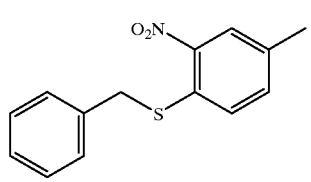 Y-77
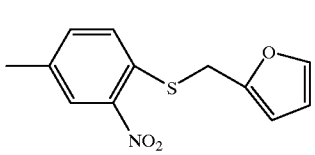 Y-78
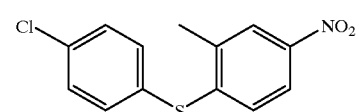 Y-79
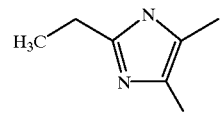 Y-80
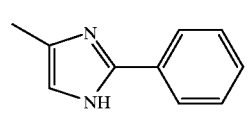 Y-81
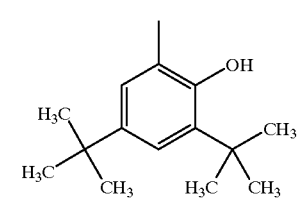 Y-82
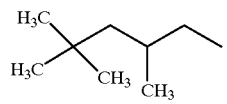 Y-83
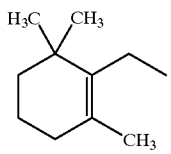 Y-84

TABLE 2-continued
Y Moieties
| | |
|---|---|
| 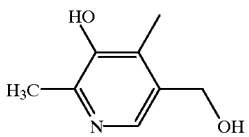 | Y-85 |
| 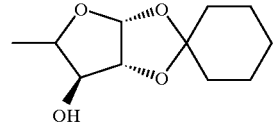 | Y-86 |
| 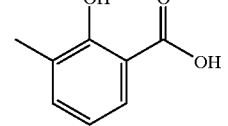 | Y-87 |
| 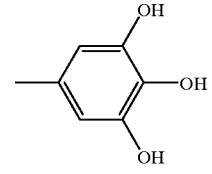 | Y-88 |
| 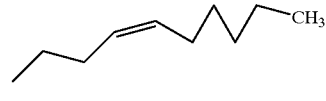 | Y-89 |
| 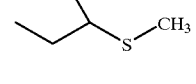 | Y-90 |
| 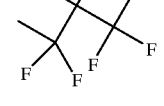 | Y-91 |
| 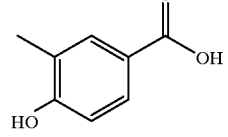 | Y-92 |
| 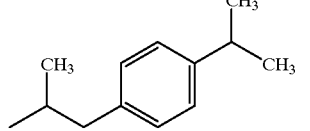 | Y-93 |
| 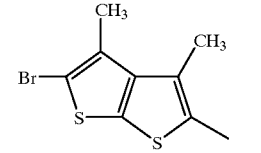 | Y-94 |
TABLE 2-continued
Y Moieties
| | |
|---|---|
| 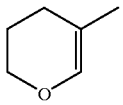 | Y-95 |
| 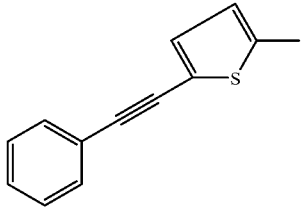 | Y-96 |
| 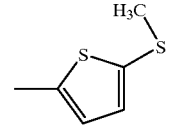 | Y-97 |
| 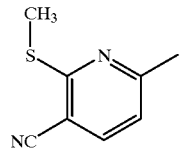 | Y-98 |
| 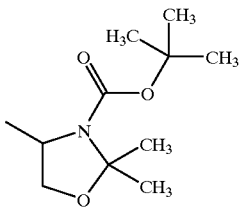 | Y-99 |
| 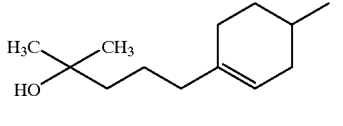 | Y-100 |
| 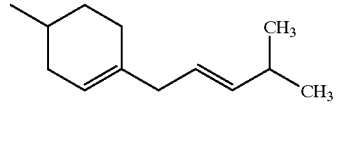 | Y-101 |
| 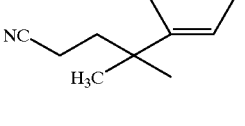 | Y-102 |
| 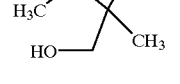 | Y-103 |

TABLE 2-continued
Y Moieties
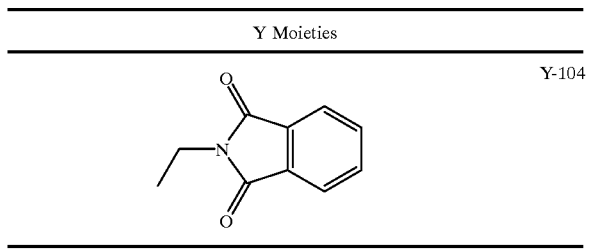
Y-104
TABLE 3
Z Moieties
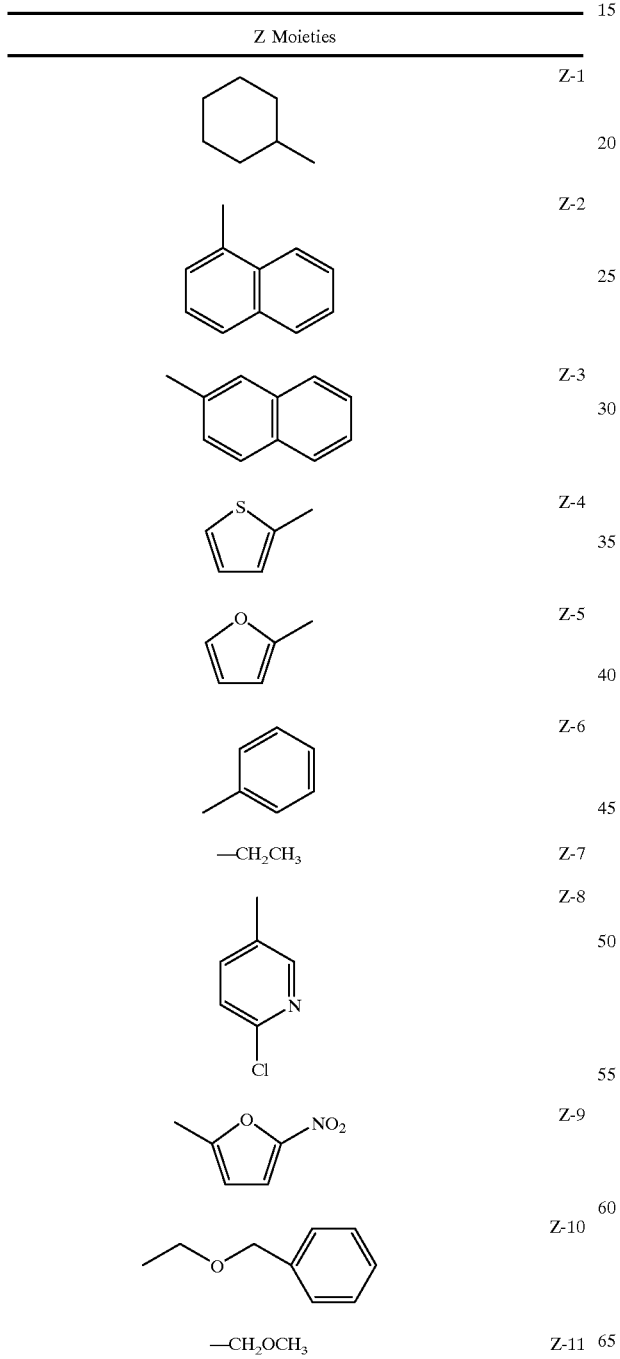
TABLE 3-continued
Z Moieties
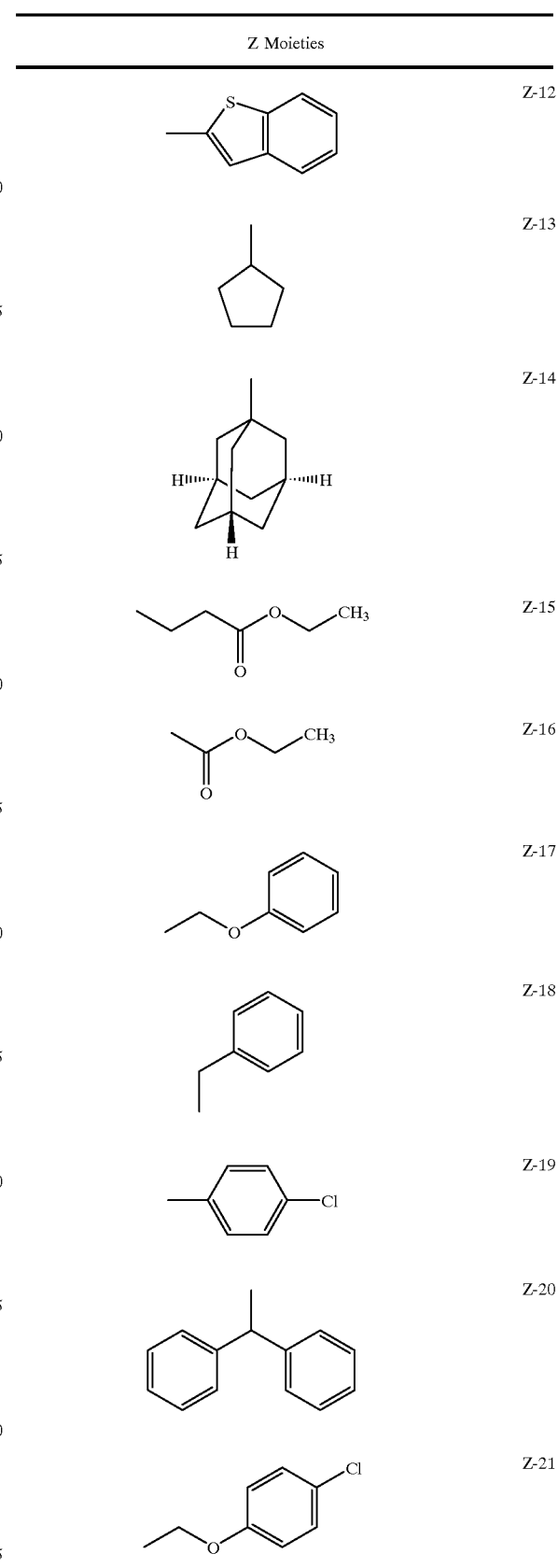

TABLE 3-continued
Z Moieties
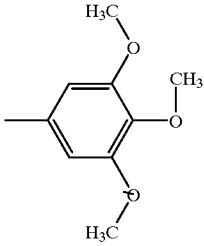 Z-22
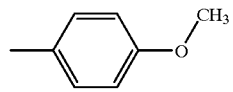 Z-23
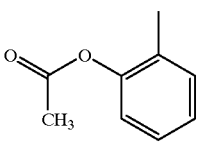 Z-24
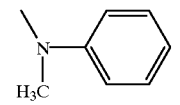 Z-25
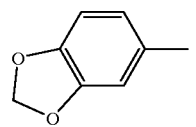 Z-26
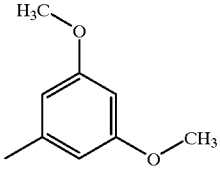 Z-27
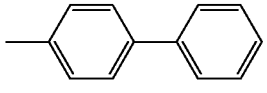 Z-28
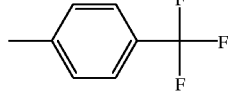 Z-29
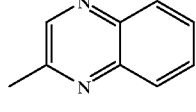 Z-30
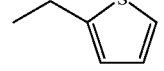 Z-31
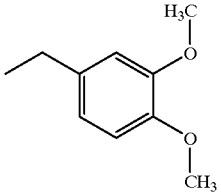 Z-32
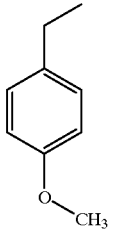 Z-33
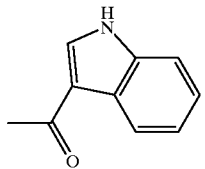 Z-34
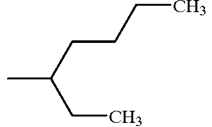 Z-35
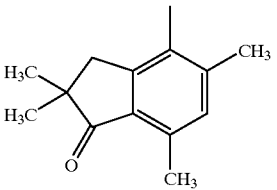 Z-36
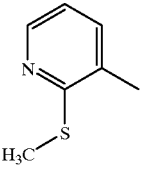 Z-37
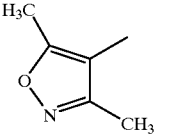 Z-38
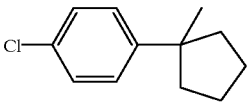 Z-39

US 6,218,426 B1
TABLE 3-continued
Z Moieties
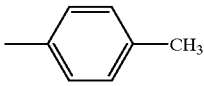 Z-40
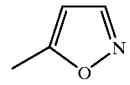 Z-41
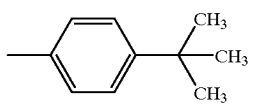 Z-42
 Z-43
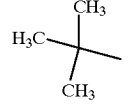 Z-44
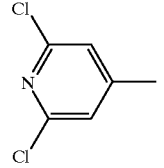 Z-45
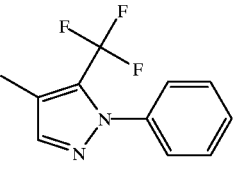 Z-46
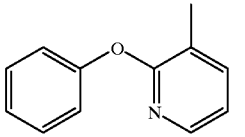 Z-47
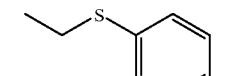 Z-48
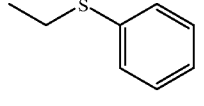 Z-49
TABLE 3-continued
Z Moieties
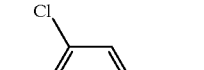 Z-50
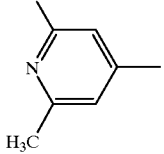 Z-51
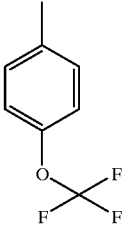 Z-52
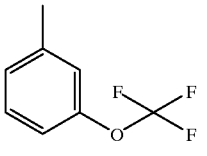 Z-53
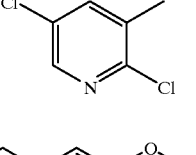 Z-54
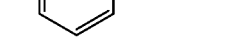 Z-55
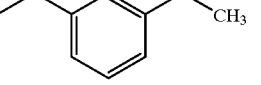 Z-56
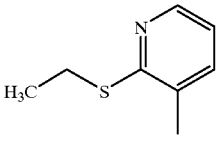 Z-57

TABLE 3-continued

Z Moieties

| ID | Structure |
|---|---|
| Z-58 | camphor-like bicyclic lactone (1,7,7-trimethyl-2-oxabicyclo structure with ketone) |
| Z-59 | 4-chloro-ethylbenzene (ethyl–C$_6$H$_4$–Cl) |
| Z-60 | sec-butylbenzene (CH$_3$CH$_2$CH(CH$_3$)–phenyl) |
| Z-61 | 4-pentyltoluene |
| Z-62 | menthyl ethyl ether (cyclohexane with CH$_3$, isopropyl, and OEt substituents) |
| Z-63 | 2-methylpentyl |
| Z-64 | 1-methyl-2-(2-ethoxyethyl)naphthalene, H$_3$C(H$_2$C)O– |
| Z-65 | 4-methylphenyl butyl ether |
| Z-66 | methylcyclobutane |
| Z-67 | ethyl pentanoate |
| Z-68 | 1-phenylethyl acetate |
| Z-69 | 2-methyl-1-(trifluoromethoxy)benzene |
| Z-70 | 3-methyl-2-(4-chlorophenoxy)pyridine |
| Z-71 | 2-methyl-3-(trifluoromethyl)-4-fluorobenzene (methyl, CF$_3$, F on benzene) |
| Z-72 | methyl hexanoate |
| Z-73 | 2-ethyl-1,4-dimethoxybenzene |
| Z-74 | 2,4,6-trichlorotoluene |
| Z-75 | 2,2-dimethylbutyl (H$_3$C, H$_3$C, CH$_3$, CH$_2$CH$_3$) |

TABLE 3-continued
Z Moieties
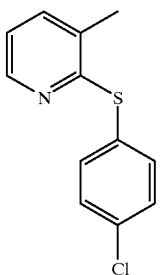 Z-76
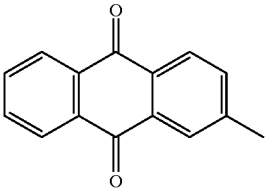 Z-77
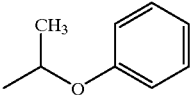 Z-78
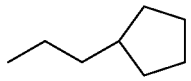 Z-79
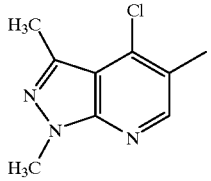 Z-80
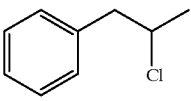 Z-81
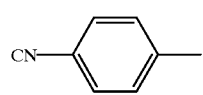 Z-82
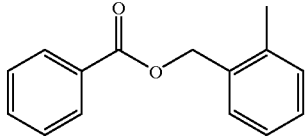 Z-83
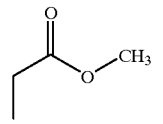 Z-84
TABLE 3-continued
Z Moieties
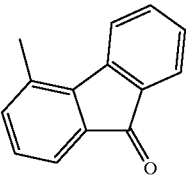 Z-85
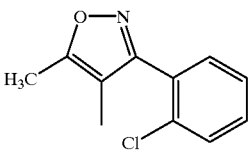 Z-86
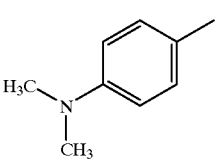 Z-87
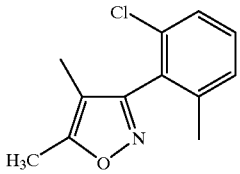 Z-88
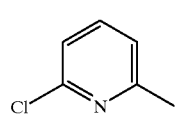 Z-89
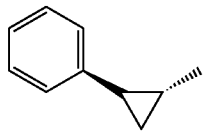 Z-90
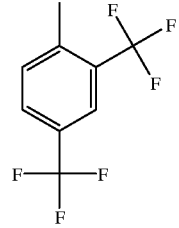 Z-91
—CH(CH$_2$CH$_3$)$_2$  Z-92
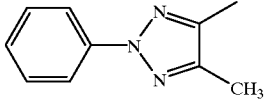 Z-93
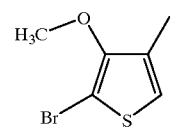 Z-94

TABLE 3-continued

Z Moieties

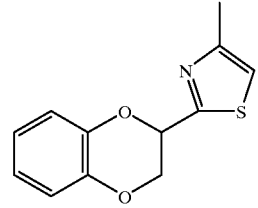
Z-95

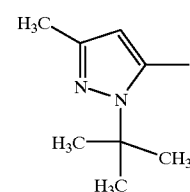
Z-96

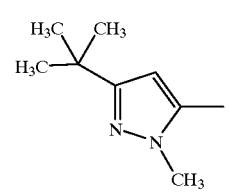
Z-97

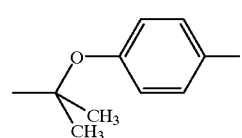
Z-98

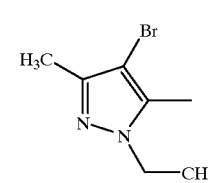
Z-99

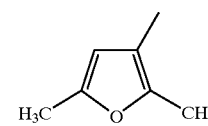
Z-100

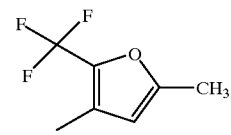
Z-101

TABLE 4

GnRH Receptor Competitive Binding Assay Results
For Compounds of Formula I

| $X_1X_2$ | Y | Z | % |
|---|---|---|---|
| $X_1X_2$-7 | Y-2 | Z-1 | 66 |
| $X_1X_2$-7 | Y-3 | Z-1 | 75 |
| $X_1X_2$-7 | Y-4 | Z-1 | 79 |
| $X_1X_2$-7 | Y-5 | Z-1 | 55 |
| $X_1X_2$-7 | Y-6 | Z-1 | 73 |
| $X_1X_2$-7 | Y-7 | Z-1 | 51 |
| $X_1X_2$-7 | Y-8 | Z-1 | 65 |
| $X_1X_2$-7 | Y-9 | Z-1 | 75 |
| $X_1X_2$-7 | Y-11 | Z-1 | 80 |
| $X_1X_2$-7 | Y-2 | Z-2 | 57 |
| $X_1X_2$-7 | Y-3 | Z-2 | 60 |
| $X_1X_2$-7 | Y-4 | Z-2 | 64 |
| $X_1X_2$-7 | Y-5 | Z-2 | 40 |
| $X_1X_2$-7 | Y-7 | Z-2 | 55 |
| $X_1X_2$-7 | Y-9 | Z-2 | 60 |
| $X_1X_2$-7 | Y-10 | Z-2 | 78 |
| $X_1X_2$-7 | Y-11 | Z-2 | 69 |
| $X_1X_2$-7 | Y-2 | Z-3 | 55 |
| $X_1X_2$-7 | Y-3 | Z-3 | 53 |
| $X_1X_2$-7 | Y-4 | Z-3 | 65 |
| $X_1X_2$-7 | Y-5 | Z-3 | 41 |
| $X_1X_2$-7 | Y-6 | Z-3 | 65 |
| $X_1X_2$-7 | Y-7 | Z-3 | 57 |
| $X_1X_2$-7 | Y-9 | Z-3 | 66 |
| $X_1X_2$-7 | Y-11 | Z-3 | 74 |
| $X_1X_2$-7 | Y-2 | Z-4 | 61 |
| $X_1X_2$-7 | Y-3 | Z-4 | 75 |
| $X_1X_2$-7 | Y-4 | Z-4 | 73 |
| $X_1X_2$-7 | Y-5 | Z-4 | 47 |
| $X_1X_2$-7 | Y-6 | Z-4 | 82 |
| $X_1X_2$-7 | Y-7 | Z-4 | 74 |
| $X_1X_2$-7 | Y-8 | Z-4 | 73 |
| $X_1X_2$-7 | Y-10 | Z-4 | 88 |
| $X_1X_2$-7 | Y-11 | Z-4 | 89 |
| $X_1X_2$-7 | Y-2 | Z-5 | 56 |
| $X_1X_2$-7 | Y-3 | Z-5 | 77 |
| $X_1X_2$-7 | Y-4 | Z-5 | 78 |
| $X_1X_2$-7 | Y-5 | Z-5 | 51 |
| $X_1X_2$-7 | Y-6 | Z-5 | 87 |
| $X_1X_2$-7 | Y-7 | Z-5 | 14 |
| $X_1X_2$-7 | Y-8 | Z-5 | 59 |
| $X_1X_2$-7 | Y-9 | Z-5 | 91 |
| $X_1X_2$-7 | Y-10 | Z-5 | 52 |
| $X_1X_2$-7 | Y-11 | Z-5 | 91 |
| $X_1X_2$-7 | Y-2 | Z-6 | 59 |
| $X_1X_2$-7 | Y-3 | Z-6 | 65 |
| $X_1X_2$-7 | Y-4 | Z-6 | 71 |
| $X_1X_2$-7 | Y-5 | Z-6 | 42 |
| $X_1X_2$-7 | Y-6 | Z-6 | 81 |
| $X_1X_2$-7 | Y-8 | Z-6 | 47 |
| $X_1X_2$-7 | Y-11 | Z-6 | 78 |
| $X_1X_2$-7 | Y-2 | Z-7 | 71 |
| $X_1X_2$-7 | Y-3 | Z-7 | 84 |
| $X_1X_2$-7 | Y-6 | Z-7 | 81 |
| $X_1X_2$-7 | Y-7 | Z-7 | 58 |
| $X_1X_2$-7 | Y-8 | Z-7 | 60 |
| $X_1X_2$-7 | Y-9 | Z-7 | 91 |
| $X_1X_2$-7 | Y-10 | Z-7 | 94 |
| $X_1X_2$-7 | Y-2 | Z-8 | 58 |
| $X_1X_2$-7 | Y-4 | Z-8 | 71 |
| $X_1X_2$-7 | Y-5 | Z-8 | 51 |
| $X_1X_2$-7 | Y-6 | Z-8 | 79 |
| $X_1X_2$-7 | Y-7 | Z-8 | 50 |
| $X_1X_2$-7 | Y-8 | Z-8 | 46 |
| $X_1X_2$-7 | Y-9 | Z-8 | 85 |
| $X_1X_2$-7 | Y-10 | Z-8 | 81 |
| $X_1X_2$-7 | Y-11 | Z-8 | 80 |
| $X_1X_2$-5 | Y-1 | Z-1 | 78 |
| $X_1X_2$-5 | Y-2 | Z-1 | 53 |
| $X_1X_2$-5 | Y-3 | Z-1 | 73 |
| $X_1X_2$-5 | Y-4 | Z-1 | 67 |
| $X_1X_2$-5 | Y-5 | Z-1 | 64 |
| $X_1X_2$-5 | Y-6 | Z-1 | 71 |
| $X_1X_2$-5 | Y-7 | Z-1 | 56 |
| $X_1X_2$-5 | Y-8 | Z-1 | 52 |
| $X_1X_2$-5 | Y-9 | Z-1 | 74 |
| $X_1X_2$-5 | Y-10 | Z-1 | 70 |
| $X_1X_2$-5 | Y-11 | Z-1 | 72 |
| $X_1X_2$-5 | Y-1 | Z-2 | 73 |
| $X_1X_2$-5 | Y-2 | Z-2 | 48 |

TABLE 4-continued

GnRH Receptor Competitive Binding Assay Results
For Compounds of Formula I

| | | | |
|---|---|---|---|
| $X_1X_2$-5 | Y-3 | Z-2 | 63 |
| $X_1X_2$-5 | Y-4 | Z-2 | 61 |
| $X_1X_2$-5 | Y-5 | Z-2 | 41 |
| $X_1X_2$-5 | Y-6 | Z-2 | 59 |
| $X_1X_2$-5 | Y-7 | Z-2 | 46 |
| $X_1X_2$-5 | Y-8 | Z-2 | 45 |
| $X_1X_2$-5 | Y-9 | Z-2 | 69 |
| $X_1X_2$-5 | Y-10 | Z-2 | 64 |
| $X_1X_2$-5 | Y-11 | Z-2 | 74 |
| $X_1X_2$-5 | Y-1 | Z-3 | 74 |
| $X_1X_2$-5 | Y-2 | Z-3 | 53 |
| $X_1X_2$-5 | Y-3 | Z-3 | 59 |
| $X_1X_2$-5 | Y-4 | Z-3 | 66 |
| $X_1X_2$-5 | Y-5 | Z-3 | 35 |
| $X_1X_2$-5 | Y-6 | Z-3 | 63 |
| $X_1X_2$-5 | Y-7 | Z-3 | 53 |
| $X_1X_2$-5 | Y-8 | Z-3 | 59 |
| $X_1X_2$-5 | Y-9 | Z-3 | 65 |
| $X_1X_2$-5 | Y-11 | Z-3 | 76 |
| $X_1X_2$-5 | Y-2 | Z-4 | 56 |
| $X_1X_2$-5 | Y-3 | Z-4 | 75 |
| $X_1X_2$-5 | Y-4 | Z-4 | 74 |
| $X_1X_2$-5 | Y-5 | Z-4 | 63 |
| $X_1X_2$-5 | Y-6 | Z-4 | 74 |
| $X_1X_2$-5 | Y-7 | Z-4 | 70 |
| $X_1X_2$-5 | Y-8 | Z-4 | 68 |
| $X_1X_2$-5 | Y-2 | Z-5 | 61 |
| $X_1X_2$-5 | Y-3 | Z-5 | 67 |
| $X_1X_2$-5 | Y-4 | Z-5 | 68 |
| $X_1X_2$-5 | Y-5 | Z-5 | 66 |
| $X_1X_2$-5 | Y-6 | Z-5 | 78 |
| $X_1X_2$-5 | Y-7 | Z-5 | 29 |
| $X_1X_2$-5 | Y-8 | Z-5 | 71 |
| $X_1X_2$-5 | Y-10 | Z-5 | 74 |
| $X_1X_2$-5 | Y-2 | Z-6 | 63 |
| $X_1X_2$-5 | Y-3 | Z-6 | 72 |
| $X_1X_2$-5 | Y-4 | Z-6 | 70 |
| $X_1X_2$-5 | Y-5 | Z-6 | 66 |
| $X_1X_2$-5 | Y-6 | Z-6 | 72 |
| $X_1X_2$-5 | Y-7 | Z-6 | 44 |
| $X_1X_2$-5 | Y-8 | Z-6 | 50 |
| $X_1X_2$-5 | Y-9 | Z-6 | 78 |
| $X_1X_2$-5 | Y-11 | Z-6 | 79 |
| $X_1X_2$-5 | Y-2 | Z-7 | 80 |
| $X_1X_2$-5 | Y-3 | Z-7 | 82 |
| $X_1X_2$-5 | Y-4 | Z-7 | 70 |
| $X_1X_2$-5 | Y-5 | Z-7 | 75 |
| $X_1X_2$-5 | Y-6 | Z-7 | 78 |
| $X_1X_2$-5 | Y-7 | Z-7 | 59 |
| $X_1X_2$-5 | Y-8 | Z-7 | 50 |
| $X_1X_2$-5 | Y-9 | Z-7 | 84 |
| $X_1X_2$-5 | Y-10 | Z-7 | 78 |
| $X_1X_2$-5 | Y-11 | Z-7 | 80 |
| $X_1X_2$-5 | Y-2 | Z-8 | 61 |
| $X_1X_2$-5 | Y-3 | Z-8 | 83 |
| $X_1X_2$-5 | Y-4 | Z-8 | 74 |
| $X_1X_2$-5 | Y-5 | Z-8 | 62 |
| $X_1X_2$-5 | Y-6 | Z-8 | 88 |
| $X_1X_2$-5 | Y-7 | Z-8 | 52 |
| $X_1X_2$-5 | Y-8 | Z-8 | 64 |
| $X_1X_2$-5 | Y-9 | Z-8 | 79 |
| $X_1X_2$-5 | Y-11 | Z-8 | 85 |
| $X_1X_2$-9 | Y-2 | Z-1 | 69 |
| $X_1X_2$-9 | Y-3 | Z-1 | 91 |
| $X_1X_2$-9 | Y-4 | Z-1 | 95 |
| $X_1X_2$-9 | Y-5 | Z-1 | 59 |
| $X_1X_2$-9 | Y-6 | Z-1 | 71 |
| $X_1X_2$-9 | Y-7 | Z-1 | 57 |
| $X_1X_2$-9 | Y-8 | Z-1 | 64 |
| $X_1X_2$-9 | Y-9 | Z-1 | 77 |
| $X_1X_2$-9 | Y-11 | Z-1 | 82 |
| $X_1X_2$-9 | Y-2 | Z-2 | 74 |
| $X_1X_2$-9 | Y-3 | Z-2 | 71 |
| $X_1X_2$-9 | Y-4 | Z-2 | 81 |
| $X_1X_2$-9 | Y-5 | Z-2 | 59 |
| $X_1X_2$-9 | Y-6 | Z-2 | 70 |
| $X_1X_2$-9 | Y-7 | Z-2 | 65 |
| $X_1X_2$-9 | Y-8 | Z-2 | 71 |
| $X_1X_2$-9 | Y-9 | Z-2 | 67 |
| $X_1X_2$-9 | Y-10 | Z-2 | 91 |
| $X_1X_2$-9 | Y-11 | Z-2 | 77 |
| $X_1X_2$-9 | Y-2 | Z-3 | 68 |
| $X_1X_2$-9 | Y-3 | Z-3 | 56 |
| $X_1X_2$-9 | Y-4 | Z-3 | 68 |
| $X_1X_2$-9 | Y-5 | Z-3 | 46 |
| $X_1X_2$-9 | Y-6 | Z-3 | 63 |
| $X_1X_2$-9 | Y-7 | Z-3 | 60 |
| $X_1X_2$-9 | Y-8 | Z-3 | 69 |
| $X_1X_2$-9 | Y-9 | Z-3 | 75 |
| $X_1X_2$-9 | Y-11 | Z-3 | 74 |
| $X_1X_2$-9 | Y-2 | Z-4 | 67 |
| $X_1X_2$-9 | Y-3 | Z-4 | 86 |
| $X_1X_2$-9 | Y-4 | Z-4 | 85 |
| $X_1X_2$-9 | Y-6 | Z-4 | 92 |
| $X_1X_2$-9 | Y-7 | Z-4 | 81 |
| $X_1X_2$-9 | Y-8 | Z-4 | 78 |
| $X_1X_2$-9 | Y-9 | Z-4 | 98 |
| $X_1X_2$-9 | Y-10 | Z-4 | 82 |
| $X_1X_2$-9 | Y-11 | Z-4 | 98 |
| $X_1X_2$-9 | Y-2 | Z-5 | 63 |
| $X_1X_2$-9 | Y-3 | Z-5 | 83 |
| $X_1X_2$-9 | Y-4 | Z-5 | 88 |
| $X_1X_2$-9 | Y-5 | Z-5 | 75 |
| $X_1X_2$-9 | Y-6 | Z-5 | 94 |
| $X_1X_2$-9 | Y-7 | Z-5 | 12 |
| $X_1X_2$-9 | Y-8 | Z-5 | 76 |
| $X_1X_2$-9 | Y-10 | Z-5 | 82 |
| $X_1X_2$-9 | Y-11 | Z-5 | 94 |
| $X_1X_2$-9 | Y-2 | Z-6 | 76 |
| $X_1X_2$-9 | Y-3 | Z-6 | 89 |
| $X_1X_2$-9 | Y-4 | Z-6 | 83 |
| $X_1X_2$-9 | Y-5 | Z-6 | 67 |
| $X_1X_2$-9 | Y-6 | Z-6 | 81 |
| $X_1X_2$-9 | Y-7 | Z-6 | 69 |
| $X_1X_2$-9 | Y-8 | Z-6 | 74 |
| $X_1X_2$-9 | Y-9 | Z-6 | 87 |
| $X_1X_2$-9 | Y-11 | Z-6 | 93 |
| $X_1X_2$-9 | Y-1 | Z-7 | 84 |
| $X_1X_2$-9 | Y-2 | Z-7 | 84 |
| $X_1X_2$-9 | Y-3 | Z-7 | 83 |
| $X_1X_2$-9 | Y-4 | Z-7 | 88 |
| $X_1X_2$-9 | Y-5 | Z-7 | 81 |
| $X_1X_2$-9 | Y-6 | Z-7 | 86 |
| $X_1X_2$-9 | Y-7 | Z-7 | 69 |
| $X_1X_2$-9 | Y-8 | Z-7 | 67 |
| $X_1X_2$-9 | Y-9 | Z-7 | 96 |
| $X_1X_2$-9 | Y-10 | Z-7 | 88 |
| $X_1X_2$-9 | Y-11 | Z-7 | 96 |
| $X_1X_2$-9 | Y-1 | Z-8 | 94 |
| $X_1X_2$-9 | Y-2 | Z-8 | 78 |
| $X_1X_2$-9 | Y-3 | Z-8 | 89 |
| $X_1X_2$-9 | Y-4 | Z-8 | 82 |
| $X_1X_2$-9 | Y-5 | Z-8 | 69 |
| $X_1X_2$-9 | Y-6 | Z-8 | 89 |
| $X_1X_2$-9 | Y-7 | Z-8 | 66 |
| $X_1X_2$-9 | Y-9 | Z-8 | 87 |
| $X_1X_2$-9 | Y-10 | Z-8 | 90 |
| $X_1X_2$-9 | Y-11 | Z-8 | 84 |
| $X_1X_2$-3 | Y-2 | Z-1 | 60 |
| $X_1X_2$-3 | Y-5 | Z-1 | 54 |
| $X_1X_2$-3 | Y-6 | Z-1 | 66 |
| $X_1X_2$-3 | Y-7 | Z-1 | 57 |
| $X_1X_2$-3 | Y-8 | Z-1 | 57 |
| $X_1X_2$-3 | Y-9 | Z-1 | 72 |
| $X_1X_2$-3 | Y-11 | Z-1 | 67 |
| $X_1X_2$-3 | Y-1 | Z-2 | 73 |
| $X_1X_2$-3 | Y-2 | Z-2 | 46 |
| $X_1X_2$-3 | Y-5 | Z-2 | 39 |
| $X_1X_2$-3 | Y-6 | Z-2 | 47 |
| $X_1X_2$-3 | Y-7 | Z-2 | 46 |
| $X_1X_2$-3 | Y-9 | Z-2 | 50 |
| $X_1X_2$-3 | Y-10 | Z-2 | 61 |

TABLE 4-continued

GnRH Receptor Competitive Binding Assay Results
For Compounds of Formula I

| $X_1X_2$ | Y | Z | % | % | Av % |
|---|---|---|---|---|---|
| $X_1X_2$-3 | Y-11 | Z-2 | | | 59 |
| $X_1X_2$-3 | Y-2 | Z-3 | | | 54 |
| $X_1X_2$-3 | Y-3 | Z-3 | | | 45 |
| $X_1X_2$-3 | Y-4 | Z-3 | | | 51 |
| $X_1X_2$-3 | Y-5 | Z-3 | | | 48 |
| $X_1X_2$-3 | Y-6 | Z-3 | | | 48 |
| $X_1X_2$-3 | Y-7 | Z-3 | | | 49 |
| $X_1X_2$-3 | Y-9 | Z-3 | | | 50 |
| $X_1X_2$-3 | Y-11 | Z-3 | | | 65 |
| $X_1X_2$-3 | Y-2 | Z-4 | | | 47 |
| $X_1X_2$-3 | Y-3 | Z-4 | | | 64 |
| $X_1X_2$-3 | Y-4 | Z-4 | | | 76 |
| $X_1X_2$-3 | Y-5 | Z-4 | | | 62 |
| $X_1X_2$-3 | Y-6 | Z-4 | | | 68 |
| $X_1X_2$-3 | Y-7 | Z-4 | | | 70 |
| $X_1X_2$-3 | Y-2 | Z-5 | | | 65 |
| $X_1X_2$-3 | Y-3 | Z-5 | | | 77 |
| $X_1X_2$-3 | Y-4 | Z-5 | | | 77 |
| $X_1X_2$-3 | Y-5 | Z-5 | | | 64 |
| $X_1X_2$-3 | Y-6 | Z-5 | | | 81 |
| $X_1X_2$-3 | Y-7 | Z-5 | | | −2 |
| $X_1X_2$-3 | Y-10 | Z-5 | | | 50 |
| $X_1X_2$-3 | Y-2 | Z-6 | | | 58 |
| $X_1X_2$-3 | Y-3 | Z-6 | | | 70 |
| $X_1X_2$-3 | Y-4 | Z-6 | | | 68 |
| $X_1X_2$-3 | Y-5 | Z-6 | | | 61 |
| $X_1X_2$-3 | Y-6 | Z-6 | | | 70 |
| $X_1X_2$-3 | Y-7 | Z-6 | | | 56 |
| $X_1X_2$-3 | Y-8 | Z-6 | | | 49 |
| $X_1X_2$-3 | Y-9 | Z-6 | | | 72 |
| $X_1X_2$-3 | Y-11 | Z-6 | | | 76 |
| $X_1X_2$-3 | Y-2 | Z-7 | | | 65 |
| $X_1X_2$-3 | Y-3 | Z-7 | | | 81 |
| $X_1X_2$-3 | Y-4 | Z-7 | | | 70 |
| $X_1X_2$-3 | Y-5 | Z-7 | | | 77 |
| $X_1X_2$-3 | Y-6 | Z-7 | | | 68 |
| $X_1X_2$-3 | Y-7 | Z-7 | | | 47 |
| $X_1X_2$-3 | Y-8 | Z-7 | | | 49 |
| $X_1X_2$-3 | Y-2 | Z-8 | | | 63 |
| $X_1X_2$-3 | Y-3 | Z-8 | | | 74 |
| $X_1X_2$-3 | Y-4 | Z-8 | | | 64 |
| $X_1X_2$-3 | Y-5 | Z-8 | | | 53 |
| $X_1X_2$-3 | Y-7 | Z-8 | | | 57 |
| $X_1X_2$-3 | Y-8 | Z-8 | | | 46 |
| $X_1X_2$-3 | Y-9 | Z-8 | | | 70 |
| $X_1X_2$-3 | Y-11 | Z-8 | | | 80 |

| $X_1X_2$ | Y | Z | % | % | Av % |
|---|---|---|---|---|---|
| $X_1X_2$-11 | Y-2 | Z-1 | 88 | 82 | 85 |
| $X_1X_2$-11 | Y-3 | Z-1 | 107 | 101 | 104 |
| $X_1X_2$-11 | Y-4 | Z-1 | 88 | 88 | 88 |
| $X_1X_2$-11 | Y-5 | Z-1 | 86 | 78 | 82 |
| $X_1X_2$-11 | Y-6 | Z-1 | 97 | 90 | 93.5 |
| $X_1X_2$-11 | Y-7 | Z-1 | 75 | 79 | 77 |
| $X_1X_2$-11 | Y-8 | Z-1 | 84 | 69 | 76.5 |
| $X_1X_2$-11 | Y-9 | Z-1 | 106 | 93 | 99.5 |
| $X_1X_2$-11 | Y-10 | Z-1 | 94 | 81 | 87.5 |
| $X_1X_2$-11 | Y-11 | Z-1 | 96 | 95 | 95.5 |
| $X_1X_2$-11 | Y-2 | Z-2 | 80 | 76 | 78 |
| $X_1X_2$-11 | Y-3 | Z-2 | 99 | 94 | 96.5 |
| $X_1X_2$-11 | Y-4 | Z-2 | 93 | 83 | 88 |
| $X_1X_2$-11 | Y-5 | Z-2 | 69 | 58 | 63.5 |
| $X_1X_2$-11 | Y-6 | Z-2 | 88 | 80 | 84 |
| $X_1X_2$-11 | Y-7 | Z-2 | 73 | 63 | 68 |
| $X_1X_2$-11 | Y-8 | Z-2 | 74 | 69 | 71.5 |
| $X_1X_2$-11 | Y-9 | Z-2 | 95 | 88 | 91.5 |
| $X_1X_2$-11 | Y-10 | Z-2 | 92 | 78 | 85 |
| $X_1X_2$-11 | Y-11 | Z-2 | 98 | 87 | 92.5 |
| $X_1X_2$-11 | Y-2 | Z-3 | 79 | 77 | 78 |
| $X_1X_2$-11 | Y-3 | Z-3 | 98 | 81 | 89.5 |
| $X_1X_2$-11 | Y-4 | Z-3 | 93 | 85 | 89 |
| $X_1X_2$-11 | Y-5 | Z-3 | 51 | 44 | 47.5 |
| $X_1X_2$-11 | Y-6 | Z-3 | 81 | 81 | 81 |
| $X_1X_2$-11 | Y-7 | Z-3 | 74 | 68 | 71 |
| $X_1X_2$-11 | Y-8 | Z-3 | 70 | 64 | 67 |
| $X_1X_2$-11 | Y-9 | Z-3 | 83 | 78 | 80.5 |
| $X_1X_2$-11 | Y-10 | Z-3 | 80 | 72 | 76 |
| $X_1X_2$-11 | Y-11 | Z-3 | 90 | 81 | 85.5 |
| $X_1X_2$-11 | Y-2 | Z-4 | 85 | 70 | 77.5 |
| $X_1X_2$-11 | Y-3 | Z-4 | 103 | 98 | 100.5 |
| $X_1X_2$-11 | Y-4 | Z-4 | 92 | 83 | 87.5 |
| $X_1X_2$-11 | Y-5 | Z-4 | 90 | 79 | 84.5 |
| $X_1X_2$-11 | Y-6 | Z-4 | 102 | 94 | 98 |
| $X_1X_2$-11 | Y-7 | Z-4 | 73 | 61 | 67 |
| $X_1X_2$-11 | Y-8 | Z-4 | 59 | 54 | 56.5 |
| $X_1X_2$-11 | Y-9 | Z-4 | 107 | 97 | 102 |
| $X_1X_2$-11 | Y-10 | Z-4 | 98 | 97 | 97.5 |
| $X_1X_2$-11 | Y-11 | Z-4 | 105 | 100 | 102.5 |
| $X_1X_2$-11 | Y-2 | Z-5 | 92 | 75 | 83.5 |
| $X_1X_2$-11 | Y-3 | Z-5 | 102 | 98 | 100 |
| $X_1X_2$-11 | Y-4 | Z-5 | 90 | 87 | 88.5 |
| $X_1X_2$-11 | Y-5 | Z-5 | 101 | 82 | 91.5 |
| $X_1X_2$-11 | Y-6 | Z-5 | 111 | 92 | 101.5 |
| $X_1X_2$-11 | Y-7 | Z-5 | 80 | 74 | 77 |
| $X_1X_2$-11 | Y-8 | Z-5 | 47 | 43 | 45 |
| $X_1X_2$-11 | Y-9 | Z-5 | 101 | 90 | 95.5 |
| $X_1X_2$-11 | Y-10 | Z-5 | 95 | 94 | 94.5 |
| $X_1X_2$-11 | Y-11 | Z-5 | 108 | 94 | 101 |
| $X_1X_2$-11 | Y-2 | Z-6 | 86 | 80 | 83 |
| $X_1X_2$-11 | Y-3 | Z-6 | 114 | 97 | 105.5 |
| $X_1X_2$-11 | Y-4 | Z-6 | 85 | 102 | 93.5 |
| $X_1X_2$-11 | Y-5 | Z-6 | 88 | 82 | 85 |
| $X_1X_2$-11 | Y-6 | Z-6 | 100 | 97 | 98.5 |
| $X_1X_2$-11 | Y-7 | Z-6 | 74 | 72 | 73 |
| $X_1X_2$-11 | Y-8 | Z-6 | 73 | 68 | 70.5 |
| $X_1X_2$-11 | Y-9 | Z-6 | 103 | 95 | 99 |
| $X_1X_2$-11 | Y-10 | Z-6 | 101 | 90 | 95.5 |
| $X_1X_2$-11 | Y-11 | Z-6 | 103 | 95 | 99 |
| $X_1X_2$-11 | Y-2 | Z-7 | 105 | 90 | 97.5 |
| $X_1X_2$-11 | Y-3 | Z-7 | 107 | 104 | 105.5 |
| $X_1X_2$-11 | Y-4 | Z-7 | 104 | 96 | 100 |
| $X_1X_2$-11 | Y-5 | Z-7 | 108 | 94 | 101 |
| $X_1X_2$-11 | Y-6 | Z-7 | 104 | 92 | 98 |
| $X_1X_2$-11 | Y-7 | Z-7 | 87 | 75 | 81 |
| $X_1X_2$-11 | Y-8 | Z-7 | 76 | 73 | 74.5 |
| $X_1X_2$-11 | Y-9 | Z-7 | 108 | 100 | 104 |
| $X_1X_2$-11 | Y-10 | Z-7 | 106 | 97 | 101.5 |
| $X_1X_2$-11 | Y-11 | Z-7 | 106 | 98 | 102 |
| $X_1X_2$-11 | Y-2 | Z-8 | 90 | 84 | 87 |
| $X_1X_2$-11 | Y-3 | Z-8 | 112 | 97 | 104.5 |
| $X_1X_2$-11 | Y-4 | Z-8 | 96 | 89 | 92.5 |
| $X_1X_2$-11 | Y-5 | Z-8 | 85 | 76 | 80.5 |
| $X_1X_2$-11 | Y-6 | Z-8 | 98 | 101 | 99.5 |
| $X_1X_2$-11 | Y-7 | Z-8 | 79 | 79 | 79 |
| $X_1X_2$-11 | Y-8 | Z-8 | 78 | 71 | 74.5 |
| $X_1X_2$-11 | Y-9 | Z-8 | 110 | 95 | 102.5 |
| $X_1X_2$-11 | Y-10 | Z-8 | 97 | 96 | 96.5 |
| $X_1X_2$-11 | Y-11 | Z-8 | 101 | 101 | 101 |
| $X_1X_2$-1 | Y-2 | Z-9 | 76 | 79 | 77.5 |
| $X_1X_2$-1 | Y-12 | Z-9 | 65 | 62 | 63.5 |
| $X_1X_2$-1 | Y-13 | Z-9 | 91 | 95 | 93 |
| $X_1X_2$-1 | Y-5 | Z-9 | 95 | 88 | 91.5 |
| $X_1X_2$-1 | Y-7 | Z-9 | 50 | 48 | 49 |
| $X_1X_2$-1 | Y-14 | Z-9 | 92 | 92 | 92 |
| $X_1X_2$-1 | Y-2 | Z-5 | 54 | 65 | 59.5 |
| $X_1X_2$-1 | Y-3 | Z-5 | 89 | 88 | 88.5 |
| $X_1X_2$-1 | Y-12 | Z-5 | 70 | 66 | 68 |
| $X_1X_2$-1 | Y-13 | Z-5 | 79 | 79 | 79 |
| $X_1X_2$-1 | Y-5 | Z-5 | 73 | 66 | 69.5 |
| $X_1X_2$-1 | Y-7 | Z-5 | −4 | −4 | −4 |
| $X_1X_2$-1 | Y-14 | Z-5 | 56 | 45 | 50.5 |
| $X_1X_2$-1 | Y-15 | Z-5 | 64 | 66 | 65 |
| $X_1X_2$-1 | Y-16 | Z-5 | 91 | 82 | 86.5 |
| $X_1X_2$-1 | Y-10 | Z-5 | 57 | 47 | 52 |
| $X_1X_2$-1 | Y-2 | Z-10 | 64 | 72 | 68 |
| $X_1X_2$-1 | Y-3 | Z-10 | 97 | 98 | 97.5 |
| $X_1X_2$-1 | Y-12 | Z-10 | 68 | 59 | 63.5 |
| $X_1X_2$-1 | Y-13 | Z-10 | 82 | 77 | 79.5 |
| $X_1X_2$-1 | Y-5 | Z-10 | 71 | 54 | 62.5 |
| $X_1X_2$-1 | Y-7 | Z-10 | 28 | 25 | 26.5 |
| $X_1X_2$-1 | Y-14 | Z-10 | 81 | 71 | 76 |

TABLE 4-continued

GnRH Receptor Competitive Binding Assay Results
For Compounds of Formula I

| $X_1X_2$ | Y | Z | | | |
|---|---|---|---|---|---|
| $X_1X_2$-1 | Y-9 | Z-10 | 85 | 79 | 82 |
| $X_1X_2$-1 | Y-16 | Z-10 | 93 | 76 | 84.5 |
| $X_1X_2$-1 | Y-2 | Z-11 | 71 | 81 | 76 |
| $X_1X_2$-1 | Y-3 | Z-11 | 96 | 92 | 94 |
| $X_1X_2$-1 | Y-12 | Z-11 | 64 | 60 | 62 |
| $X_1X_2$-1 | Y-5 | Z-11 | 79 | 82 | 80.5 |
| $X_1X_2$-1 | Y-7 | Z-11 | 46 | 35 | 40.5 |
| $X_1X_2$-1 | Y-14 | Z-11 | 73 | 79 | 76 |
| $X_1X_2$-1 | Y-15 | Z-11 | 88 | 76 | 82 |
| $X_1X_2$-1 | Y-16 | Z-11 | 93 | 84 | 88.5 |
| $X_1X_2$-1 | Y-2 | Z-12 | 49 | 54 | 51.5 |
| $X_1X_2$-1 | Y-12 | Z-12 | 66 | 57 | 61.5 |
| $X_1X_2$-1 | Y-13 | Z-12 | 73 | 79 | 76 |
| $X_1X_2$-1 | Y-5 | Z-12 | 59 | 58 | 58.5 |
| $X_1X_2$-1 | Y-14 | Z-12 | 73 | 79 | 76 |
| $X_1X_2$-1 | Y-15 | Z-12 | 66 | 69 | 67.5 |
| $X_1X_2$-1 | Y-2 | Z-7 | 71 | 81 | 76 |
| $X_1X_2$-1 | Y-3 | Z-7 | 101 | 98 | 99.5 |
| $X_1X_2$-1 | Y-12 | Z-7 | 59 | 58 | 58.5 |
| $X_1X_2$-1 | Y-5 | Z-7 | 86 | 82 | 84 |
| $X_1X_2$-1 | Y-7 | Z-7 | 53 | 57 | 55 |
| $X_1X_2$-1 | Y-14 | Z-7 | 85 | 85 | 85 |
| $X_1X_2$-1 | Y-15 | Z-7 | 77 | 76 | 76.5 |
| $X_1X_2$-1 | Y-9 | Z-7 | 96 | 86 | 91 |
| $X_1X_2$-1 | Y-16 | Z-7 | 89 | 77 | 83 |
| $X_1X_2$-1 | Y-2 | Z-8 | 67 | 67 | 67 |
| $X_1X_2$-1 | Y-3 | Z-8 | 95 | 89 | 92 |
| $X_1X_2$-1 | Y-12 | Z-8 | 60 | 60 | 60 |
| $X_1X_2$-1 | Y-13 | Z-8 | 80 | 82 | 81 |
| $X_1X_2$-1 | Y-5 | Z-8 | 66 | 62 | 64 |
| $X_1X_2$-1 | Y-7 | Z-8 | 52 | 44 | 48 |
| $X_1X_2$-1 | Y-14 | Z-8 | 82 | 73 | 77.5 |
| $X_1X_2$-1 | Y-15 | Z-8 | 69 | 64 | 66.5 |
| $X_1X_2$-1 | Y-9 | Z-8 | 80 | 87 | 83.5 |
| $X_1X_2$-1 | Y-16 | Z-8 | 70 | 69 | 69.5 |
| $X_1X_2$-1 | Y-2 | Z-13 | 59 | 57 | 58 |
| $X_1X_2$-1 | Y-3 | Z-13 | 83 | 92 | 87.5 |
| $X_1X_2$-1 | Y-12 | Z-13 | 48 | 56 | 52 |
| $X_1X_2$-1 | Y-13 | Z-13 | 81 | 85 | 83 |
| $X_1X_2$-1 | Y-5 | Z-13 | 76 | 63 | 69.5 |
| $X_1X_2$-1 | Y-7 | Z-13 | 52 | 50 | 51 |
| $X_1X_2$-1 | Y-14 | Z-13 | 81 | 72 | 76.5 |
| $X_1X_2$-1 | Y-15 | Z-13 | 64 | 62 | 63 |
| $X_1X_2$-1 | Y-9 | Z-13 | 87 | 80 | 83.5 |
| $X_1X_2$-1 | Y-16 | Z-13 | 77 | 63 | 70 |

| $X_1X_2$ | Y | Z | % |
|---|---|---|---|
| $X_1X_2$-1 | Y-7 | Z-16 | 82 |
| $X_1X_2$-1 | Y-7 | Z-18 | 58 |
| $X_1X_2$-1 | Y-7 | Z-19 | 66 |
| $X_1X_2$-1 | Y-7 | Z-21 | 66 |
| $X_1X_2$-1 | Y-7 | Z-29 | 75 |
| $X_1X_2$-1 | Y-7 | Z-35 | 64 |
| $X_1X_2$-1 | Y-7 | Z-38 | 60 |
| $X_1X_2$-1 | Y-7 | Z-45 | 64 |
| $X_1X_2$-1 | Y-7 | Z-46 | 55 |
| $X_1X_2$-1 | Y-7 | Z-48 | 63 |
| $X_1X_2$-1 | Y-7 | Z-49 | 62 |
| $X_1X_2$-1 | Y-7 | Z-50 | 69 |
| $X_1X_2$-1 | Y-7 | Z-51 | 71 |
| $X_1X_2$-1 | Y-7 | Z-57 | 57 |
| $X_1X_2$-1 | Y-7 | Z-59 | 62 |
| $X_1X_2$-1 | Y-7 | Z-69 | 62 |
| $X_1X_2$-1 | Y-7 | Z-72 | 53 |
| $X_1X_2$-1 | Y-7 | Z-79 | 62 |
| $X_1X_2$-1 | Y-7 | Z-82 | 53 |
| $X_1X_2$-1 | Y-7 | Z-90 | 65 |
| $X_1X_2$-1 | Y-7 | Z-96 | 56 |
| $X_1X_2$-1 | Y-7 | Z-97 | 70 |
| $X_1X_2$-1 | Y-7 | Z-100 | 68 |
| $X_1X_2$-1 | Y-7 | Z-101 | 77 |
| $X_1X_2$-1 | Y-18 | Z-5 | 91 |
| $X_1X_2$-1 | Y-19 | Z-5 | 130 |
| $X_1X_2$-1 | Y-21 | Z-5 | 94 |
| $X_1X_2$-1 | Y-22 | Z-5 | 78 |
| $X_1X_2$-1 | Y-28 | Z-5 | 76 |
| $X_1X_2$-1 | Y-36 | Z-5 | 88 |
| $X_1X_2$-1 | Y-37 | Z-5 | 83 |
| $X_1X_2$-1 | Y-40 | Z-5 | 91 |
| $X_1X_2$-1 | Y-43 | Z-5 | 61 |
| $X_1X_2$-1 | Y-45 | Z-5 | 80 |
| $X_1X_2$-1 | Y-52 | Z-5 | 87 |
| $X_1X_2$-1 | Y-53 | Z-5 | 97 |
| $X_1X_2$-1 | Y-55 | Z-5 | 95 |
| $X_1X_2$-1 | Y-57 | Z-5 | 83 |
| $X_1X_2$-1 | Y-60 | Z-5 | 83 |
| $X_1X_2$-1 | Y-62 | Z-5 | 83 |
| $X_1X_2$-1 | Y-64 | Z-5 | 79 |
| $X_1X_2$-1 | Y-68 | Z-5 | 56 |
| $X_1X_2$-1 | Y-73 | Z-5 | 95 |
| $X_1X_2$-1 | Y-74 | Z-5 | 74 |
| $X_1X_2$-1 | Y-75 | Z-5 | 86 |
| $X_1X_2$-1 | Y-76 | Z-5 | 82 |
| $X_1X_2$-1 | Y-77 | Z-5 | 83 |
| $X_1X$-1 | Y-79 | Z-5 | 62 |
| $X_1X_2$-1 | Y-80 | Z-5 | 100 |
| $X_1X_2$-1 | Y-81 | Z-5 | 86 |
| $X_1X_2$-1 | Y-82 | Z-5 | 95 |
| $X_1X_2$-1 | Y-83 | Z-5 | 99 |
| $X_1X_2$-1 | Y-84 | Z-5 | 63 |
| $X_1X_2$-1 | Y-89 | Z-5 | 68 |
| $X_1X_2$-1 | Y-93 | Z-5 | 67 |
| $X_1X_2$-1 | Y-98 | Z-5 | 89 |

TABLE 5

GnRH Receptor Competitive Binding Assay Results For Compounds
(Each Tested at 10 µM)

| Compound No. | % Remaining 1st Test | % Remaining 2nd Test | Average % Remaining |
|---|---|---|---|
| 1 | 57 | 57 | 57 |
| 2 | 59 | 54 | 57 |
| 3 | 58 | 57 | 55 |
| 4 | 40 | 40 | 40 |
| 5 | 31 | 33 | 37 |
| 6 | 47 | 45 | 46 |
| 7 | 51 | 55 | 53 |
| 8 | 42 | 48 | 45 |
| 9 | 51 | 53 | 52 |
| 10 | 51 | 54 | 53 |
| 11 | 55 | 50 | 53 |
| 12 | 57 | 58 | 58 |
| 13 | 14 | 11 | 13 |
| 14 | 56 | 54 | 55 |
| 15 | 58 | 60 | 59 |
| 16 | 50 | 47 | 49 |
| 19 | 47 | 42 | 45 |
| 20 | 60 | 54 | 57 |
| 21 | 46 | 51 | 49 |
| 22 | 52 | 57 | 55 |
| 23 | 48 | 50 | 49 |
| 24 | 58 | 58 | 56 |
| 25 | 41 | 51 | 46 |
| 26 | 35 | 37 | 36 |
| 27 | 56 | 62 | 59 |
| 28 | 46 | 57 | 52 |
| 29 | 53 | 61 | 57 |
| 30 | 29 | 37 | 33 |
| 31 | 44 | 45 | 45 |
| 32 | 52 | 61 | 57 |
| 33 | 52 | 65 | 59 |
| 34 | 45 | 57 | 51 |
| 35 | 50 | 54 | 52 |
| 36 | 56 | 59 | 58 |
| 37 | 59 | 61 | 60 |
| 38 | 59 | 55 | 57 |

TABLE 5-continued

GnRH Receptor Competitive Binding Assay Results For Compounds
(Each Tested at 10 μM)

| Compound No. | % Remaining 1st Test | % Remaining 2nd Test | Average % Remaining |
|---|---|---|---|
| 39 | 46 | 45 | 46 |
| 40 | 12 | 11 | 12 |
| 41 | 46 | 43 | 45 |
| 42 | 54 | 62 | 58 |
| 43 | 47 | 53 | 50 |
| 44 | 58 | 62 | 60 |
| 46 | 45 | 52 | 49 |
| 47 | 39 | 44 | 42 |
| 48 | 48 | 40 | 44 |
| 49 | 53 | 62 | 58 |
| 50 | 47 | 62 | 55 |
| 51 | 48 | 63 | 56 |
| 52 | 57 | 59 | 58 |
| 53 | 46 | 55 | 51 |
| 54 | 49 | 59 | 54 |
| 55 | -2 | -1 | -2 |
| 56 | 56 | 60 | 58 |
| 57 | 47 | 63 | 55 |
| 58 | 57 | 60 | 59 |
| 59 | 57 | 60 | 59 |
| 62 | 49 | 55 | 52 |
| 63 | 49 | 47 | 48 |
| 64 | 46 | 51 | 49 |
| 65 | 50 | 59 | 55 |
| 66 | 50 | 57 | 54 |
| 68 | 61 | 44 | 48 |
| 69 | 59 | 54 | 57 |
| 70 | 47 | 48 | 45 |
| 71 | 54 | 65 | 60 |
| 72 | 49 | 54 | 52 |
| 73 | 59 | 57 | 58 |
| 74 | 51 | 48 | 50 |
| 75 | 59 | 58 | 59 |
| 76 | 60 | 60 | 60 |
| 77 | 48 | 56 | 52 |
| 78 | 59 | 58 | 59 |
| 79 | 50 | 48 | 49 |
| 80 | -4 | -4 | -4 |
| 81 | 28 | 25 | 27 |
| 82 | 46 | 35 | 41 |
| 83 | 53 | 57 | 55 |
| 84 | 52 | 44 | 48 |
| 85 | 52 | 50 | 51 |
| 86 | 56 | 45 | 51 |
| 87 | 57 | 47 | 52 |
| 88 | 58 | 56 | 57 |
| 94 | 61 | 52 | 57 |
| 96 | 44 | 60 | 52 |
| 98 | 58 | 58 | 58 |
| 100 | 52 | 58 | 55 |
| 102 | 66 | 54 | 60 |
| 105 | 56 | 56 | 56 |
| 117 | 59 | 54 | 57 |
| 118 | 62 | 58 | 60 |
| 119 | 57 | 57 | 57 |

The invention has been illustrated by reference to preferred embodiments and exemplary aspects of the invention. Various modifications and adaptations will become apparent to the artisan through routine practice of the invention in light of knowledge and developments in the art. Thus, the invention should be understood as not being limited by the foregoing detailed description, but as being defined by the appended claims and their equivalents.

What is claimed is:

1. A pharmaceutical composition comprising:
   (a) a therapeutically effective amount of a GnRH agent selected from the group consisting of compounds of the Formula I:

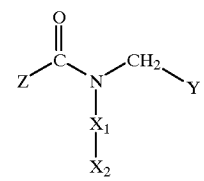

(I)

wherein:
   Z is a group selected from substituted and unsubstituted alkyl, alkenyl, alkynyl, cycloalkyl, heterocycle, aryl, heteroaryl, $CH_2OR$ and $C(O)OR$, where R is substituted or unsubstituted alkyl, alkenyl, alkynyl, cycloalkyl, aryl or heteroaryl, and where the number of carbon atoms present in Z ranges from 1 to 12;
   Y is a lipophilic group selected from substituted and unsubstituted alkyl, alkenyl, alkynyl, cycloalkyl, aryl, and heteroaryl, where the number of carbons atoms present in Y ranges from 6 to 20;
   $X_1$ is a structural unit connecting $CH_2NC(O)$, $X_2$, Y, and Z in three-dimensional space that is selected from substituted and unsubstituted alkyl, alkenyl, alkynyl, cycloalkyl, aryl, and heteroaryl such that the atom count in the chain portion of the unit linking the central nitrogen to $X_2$ ranges from 3 to 8; and
   $X_2$ is a basic group having a $pK_a$ greater than about 8 and is guanidinyl, amidinyl, or amino, unsubstituted or substituted with one or more lower alkyls; and pharmaceutically acceptable salts, multimers, prodrugs, and active metabolites thereof; and
   (b) a pharmaceutically acceptable carrier or diluent.

2. A pharmaceutical composition according to claim 1, wherein Z is a substituted or unsubstituted furyl, pyrrolyl, naphthyl, thienyl, pyridyl, $C_3$–$C_8$ cycloalkyl, $C_1$–$C_8$ alkyl, $CH_2CF_3$, or $CF_3$.

3. A pharmaceutical composition according to claim 1, wherein Z is furyl, pyrrolyl, thienyl, or $CF_3$.

4. A pharmaceutical composition according to claim 1, wherein Y is substituted or unsubstituted phenyl, naphthyl, saturated or partially saturated naphthyl derivative, dibenzylfuryl, saturated or partially saturated dibenzylfuryl derivative, quinolinyl, isoquinolinyl, quinoxalinyl, saturated or partially saturated cycloalkyl, or fused polycyclic alkyl.

5. A pharmaceutical composition according to claim 1, wherein Y is 4-isopropylphenyl, 4-N,N-dimethylaminopropyloxyphenyl, 2,4,5-triethoxyphenyl, 2,3-dibenzyloxyphenyl, 2-(4'-chlorophenyloxy)phenyl or a partially or fully saturated thereof, or 1,2,3,4-tetrahydro-1,1,4,4,6-pentamethylnaphthalen-7-yl.

6. A pharmaceutical composition according to claim 1, wherein Y is

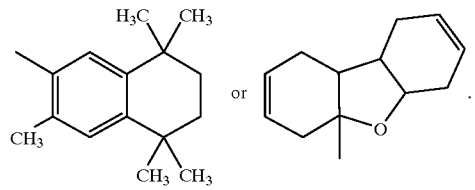

7. A pharmaceutical composition according to claim 1, wherein $X_1$ is alkylene, alkylene-($C_{5-6}$-cycloalkyl)-alkylene, or alkylene-($C_{5-6}$-aryl)-alkylene.

8. A pharmaceutical composition according to claim 7, wherein $X_1$ is selected from the group consisting of:

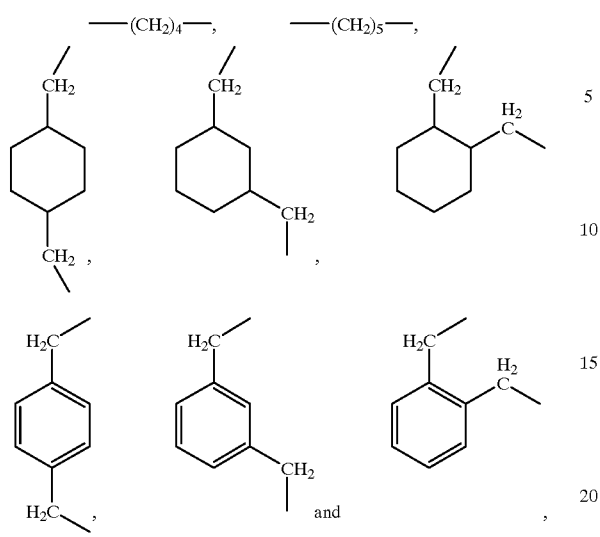
9. A pharmaceutical composition according to claim 1 wherein the $X_2$ group has a $pK_a$ greater than about 9.
10. A pharmaceutical composition according to claim 1, where $X_2$ is guanidinyl.
11. A pharmaceutical composition according to claim 1, wherein the GnRH agent is selected from the group consisting of:
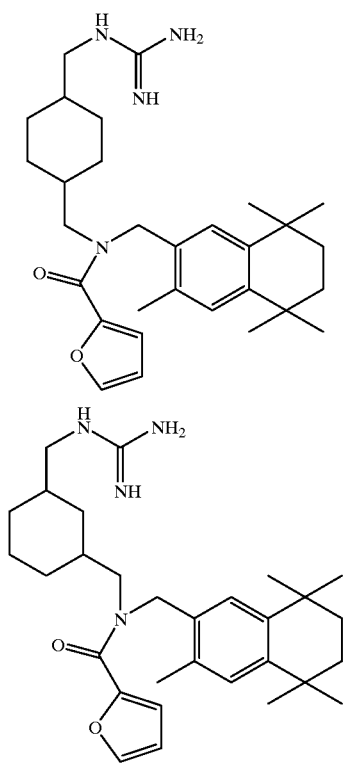
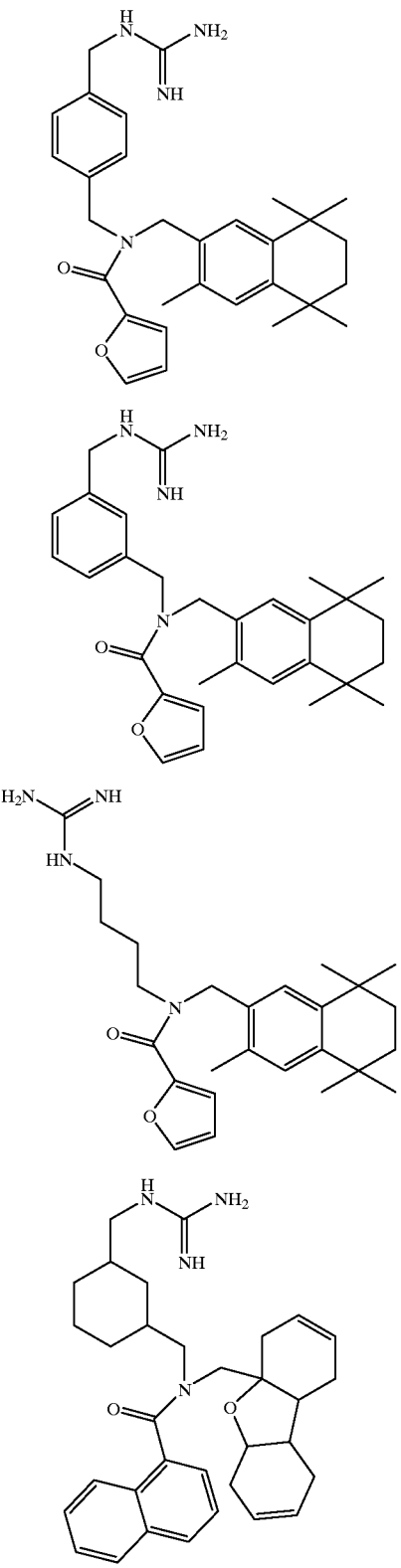

-continued

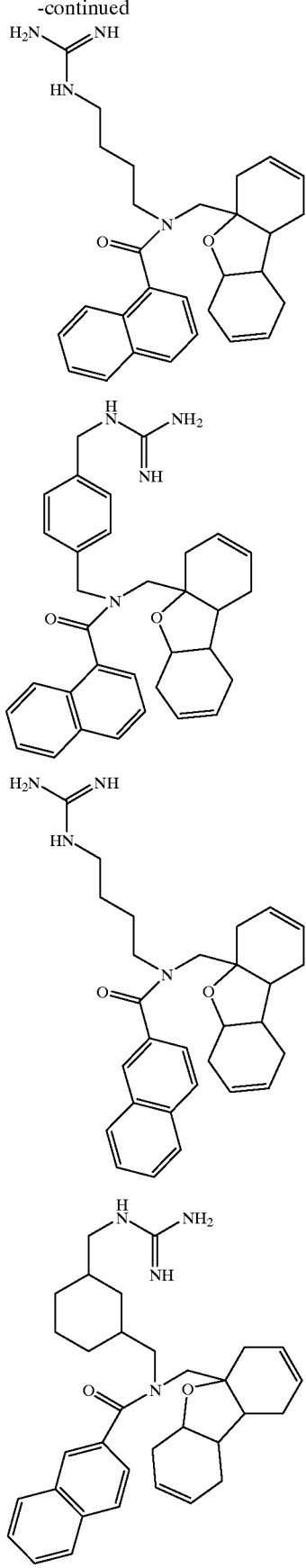

-continued

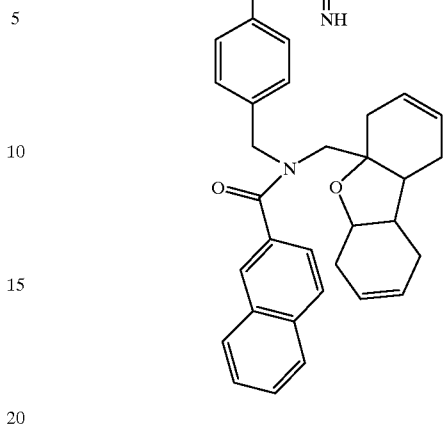

or a pharmaceutically acceptable salt, multimer, prodrug, or active metabolite thereof.

12. A pharmaceutical composition according to claim 1, wherein the compounds of the Formula I are selected from compounds of the formula:

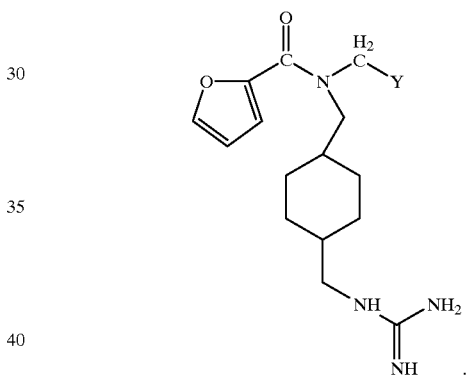

13. A pharmaceutical composition according to claim 1, wherein the compounds of the Formula I are selected from compounds of the formula:

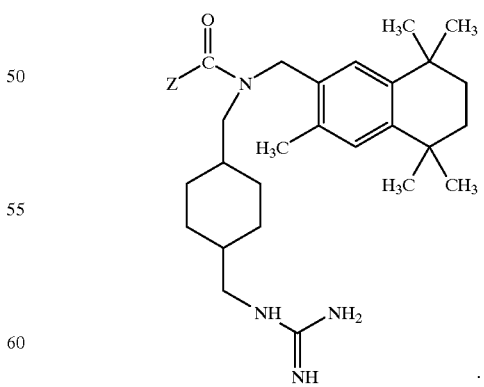

14. A method for regulating the secretion of gonadotropins in mammals, comprising administering a therapeutically effective amount of a GnRH agent selected from the group consisting of compounds of the Formula I:

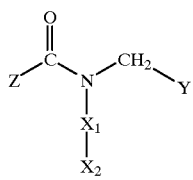
(I)

wherein:

Z is a group selected from substituted and unsubstituted alkyl, alkenyl, alkynyl, cycloalkyl, heterocycle, aryl, heteroraryl, $CH_2OR$, and $C(O)OR$, where R is substituted or unsubstituted alkyl, alkenyl, alkynyl, cycloalkyl, aryl, or heteroaryl, and where the number of carbon atoms present in Z ranges from 1 to 12;

Y is a lipophilic group selected from substituted and unsubstituted alkyl, alkenyl, alkynyl, cycloalkyl, aryl, and heteroaryl, where the number of carbon atoms present in Y ranges from 6 to 20;

$X_1$ is a structural unit connecting $CH_2NC(O)$, $X_2$, Y, and Z in three-dimensional space that is selected from substituted and unsubstituted alkyl, alkenyl, alkynyl, cycloalkyl, aryl, and heteroaryl such that the atom count in the chain portion of the unit linking the central nitrogen to $X_2$ ranges form 3 to 8; and $X_2$ is a basic group having $pK_a$ greater than about 8, and is guanidinyl, amidinyl, or amino, unsubstituted or substituted with one or more lower alkyls, and pharmaceutically acceptable salts multimers, prodrugs, and active metabolites thereof.

15. A method according to claim 14, wherein the compounds of the Formula I are selected from compounds of the formula:

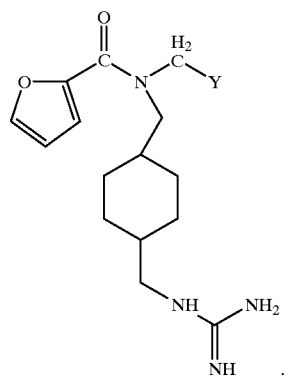

16. A method according to claim 14, wherein the compounds of the Formula I are selected from compounds of the formula:

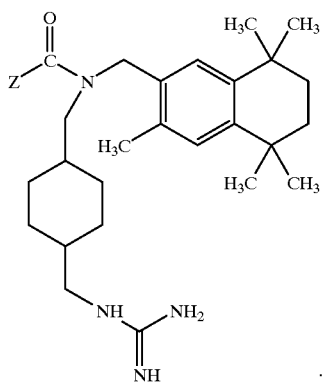

* * * * *

UNITED STATES PATENT AND TRADEMARK OFFICE
CERTIFICATE OF CORRECTION

PATENT NO.    : 6,218,426 B1
DATED         : April 17, 2001
INVENTOR(S)   : Anderson et al.

It is certified that error appears in the above-identified patent and that said Letters Patent is hereby corrected as shown below:

<u>Title page,</u>
Item [60], after "filed on", "May" should read -- March --

<u>Column 1,</u>
Line 6, after "filed on", "May 3" should read -- March 5 --

Signed and Sealed this

Twenty-fifth Day of March, 2003

JAMES E. ROGAN
*Director of the United States Patent and Trademark Office*